(12) United States Patent
Kubo et al.

(10) Patent No.: US 7,745,623 B2
(45) Date of Patent: Jun. 29, 2010

(54) CYCLIC AMIDE DERIVATIVE, AND ITS PRODUCTION AND USE

(75) Inventors: Keiji Kubo, Osaka (JP); Yasuhiro Imaeda, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 227 days.

(21) Appl. No.: 11/596,089

(22) PCT Filed: May 20, 2005

(86) PCT No.: PCT/JP2005/009711

§ 371 (c)(1),
(2), (4) Date: Nov. 9, 2006

(87) PCT Pub. No.: WO2005/113504

PCT Pub. Date: Dec. 1, 2005

(65) Prior Publication Data

US 2007/0244118 A1    Oct. 18, 2007

(30) Foreign Application Priority Data

May 21, 2004  (JP)  ............................... 2004-152000

(51) Int. Cl.
C07D 401/04  (2006.01)
(52) U.S. Cl. .................................... 544/315; 514/274
(58) Field of Classification Search ................. 544/315; 514/274
See application file for complete search history.

(56) References Cited

U.S. PATENT DOCUMENTS

| | | | |
|---|---|---|---|
| 4,147,786 A | 4/1979 | Huebner | 544/316 |
| 4,329,348 A | 5/1982 | Huebner | 544/316 |
| 4,695,575 A | 9/1987 | Janssens et al. | 514/322 |
| 5,559,232 A | 9/1996 | Ackermann et al. | |
| 5,889,024 A | 3/1999 | Miller et al. | 514/326 |
| 5,965,559 A | 10/1999 | Faull et al. | |
| 6,105,581 A | 8/2000 | Eggers et al. | |
| 6,204,265 B1 | 3/2001 | Reichard et al. | 514/235.8 |
| 6,359,134 B1 | 3/2002 | Tawada et al. | |
| 6,403,595 B1 | 6/2002 | Tawada et al. | |
| 6,423,519 B1 | 7/2002 | Bergnes et al. | |
| 6,518,538 B2 | 2/2003 | Barnabei | |
| 6,541,488 B1 | 4/2003 | Bernat et al. | |
| 6,562,828 B1 | 5/2003 | Katoh et al. | |
| 6,596,754 B1 | 7/2003 | Hara et al. | |
| 6,629,974 B2 | 10/2003 | Penny et al. | |
| 6,723,091 B2 | 4/2004 | Goble et al. | |
| 2002/0045616 A1 | 4/2002 | Stein et al. | |
| 2003/0187023 A1* | 10/2003 | Kubo et al. | 514/318 |
| 2004/0006062 A1 | 1/2004 | Smallheer et al. | |
| 2004/0077635 A1 | 4/2004 | Qiao et al. | |
| 2004/0254175 A1 | 12/2004 | Dorsch et al. | |
| 2005/0101595 A1 | 5/2005 | Chu et al. | 514/217.09 |
| 2005/0203127 A1 | 9/2005 | Cezanne et al. | |
| 2005/0282808 A1 | 12/2005 | Kawaguchi et al. | |
| 2007/0004736 A1 | 1/2007 | Kubo et al. | 514/249 |

FOREIGN PATENT DOCUMENTS

| | | |
|---|---|---|
| EP | 0 798 295 | 10/1997 |
| EP | 1 043 311 | 10/2000 |
| EP | 1 048 652 | 11/2000 |
| EP | 1 054 005 | 11/2000 |
| EP | 1 104 754 | 6/2001 |
| EP | 1 188 755 | 3/2002 |
| EP | 1 191 028 | 3/2002 |
| EP | 1 188 755 | 3/2003 |
| EP | 1 564 213 | 8/2005 |
| JP | 50-11391 | 4/1975 |
| JP | 5-208946 | 8/1993 |
| JP | 7-112970 | 5/1995 |
| JP | JO2002-201178 | * 7/2002 |
| WO | WO 95/00507 | 1/1995 |
| WO | WO 96/10022 | 4/1996 |

(Continued)

OTHER PUBLICATIONS

Kubo et al. CA:136:134784 (2002).*

(Continued)

*Primary Examiner*—Celia Chang
(74) *Attorney, Agent, or Firm*—Hamre, Schumann, Mueller & Larson, P.C.

(57) ABSTRACT

The present invention provides a cyclic amide derivative useful as a drug for treating thrombosis, which is represented by the formula (I):

$$R^1-W-S(O)_a-X^1-Y^1-A-X^2-N\underset{Z^3-X^3}{\overset{Y^2-Z^1}{\diagdown}}Z^2 \quad (I)$$

wherein $R^1$ represents an optionally substituted cyclic hydrocarbon group or an optionally substituted heterocyclic group, W represents a bond or an optionally substituted divalent chain hydrocarbon group, a represents 0, 1, or 2, $X^1$ represents an optionally substituted lower alkylene or an optionally substituted lower alkenylene, $Y^1$ represents —C(O)—, —S(O)— or —S(O)$_2$—, A represents a piperazine ring which may be further substituted or a piperidine ring which may be further substituted, $X^2$ represents a bond or an optionally substituted lower alkylene, $Y^2$ represents —C(O)—, —S(O)—, —S(O)$_2$— or —C(=NR$^7$)—, $X^3$ represents an optionally substituted $C_{1-4}$ alkylene or an optionally substituted $C_{2-4}$ alkenylene, $Z^3$ represents —N(R$^4$)—, —O— or a bond, $Z^1$ represents —C(R$^2$)(R$^2$)—, —N(R$^2$)—, etc., and $Z^2$ represents —C(R$^3$)(R$^3$)—, —N(R$^3$)—, etc., or a salt thereof.

2 Claims, No Drawings

FOREIGN PATENT DOCUMENTS

| | | |
|---|---|---|
| WO | WO 96/13262 | 5/1996 |
| WO | WO 96/16940 | 6/1996 |
| WO | WO 99/26919 | 6/1996 |
| WO | WO 96/40679 | 12/1996 |
| WO | WO 97/21437 | 6/1997 |
| WO | WO 97/29104 | 8/1997 |
| WO | WO 98/23279 | 6/1998 |
| WO | WO 98/54164 | 12/1998 |
| WO | WO 98/56365 | 12/1998 |
| WO | WO 99/09027 | 2/1999 |
| WO | WO 99/26924 | 6/1999 |
| WO | WO 99/33805 | 7/1999 |
| WO | WO 00/09480 | 2/2000 |
| WO | WO 00/13707 | 3/2000 |
| WO | WO 00/18398 | 4/2000 |
| WO | WO 00/39114 | 7/2000 |
| WO | WO 00/78747 | 12/2000 |
| WO | WO 01/02397 | 1/2001 |
| WO | WO 01/07436 | 2/2001 |
| WO | WO 01/17992 | 3/2001 |
| WO | WO 01/44172 | 6/2001 |
| WO | WO 01/77101 | 10/2001 |
| WO | WO 02/06234 | 1/2002 |
| WO | WO 02/26720 | 4/2002 |
| WO | WO 02/057223 | 7/2002 |
| WO | WO 02/068407 | 9/2002 |
| WO | WO 03/010160 | 2/2003 |
| WO | WO 03/022214 | 3/2003 |
| WO | WO 03/026652 | 4/2003 |
| WO | WO 03/039543 | 5/2003 |
| WO | WO 03/082847 | 10/2003 |
| WO | WO 2004/002477 | 1/2004 |
| WO | WO 2004/035579 | 4/2004 |
| WO | WO 2004/35579 | 4/2004 |
| WO | WO 2004/048363 | 6/2004 |
| WO | WO 2005/087266 | 9/2005 |
| WO | WO 2005/113504 | 12/2005 |

OTHER PUBLICATIONS

Kubo et al. "Preparation of heterocyclic amides . . . " Ca 144:22941 (2005).*

Kubo et al. "preparation of hydrocarbyl . . . " CA136:134784 (2002).*

Zablocki et al. "Potent in vitro . . . ". *Journal Med. Chem.*, vol. 38, pp. 2378-2394 (1995).

Maduskuie et al. "Rational design and synthesis of novel, potent bis-phenylamidine carboxxylate factor Xa inhibitors". *Journal of Medicinal Chemistry*, vol. 41, pp. 53-62 (1998).

Al-Obeidi et al. "Factor Xa Inhibitors". *Exp. Opin, Ther. Patents*, vol. 9, No. 7, pp. 321-353 (1999).

Wyngaarden et al. "Cecil Textbook of Medicine", pp. 247 (1983).

Patani et al. "Bioisosterism: A Ration al Approach in Drug Design". *Chem. Rev.*, vol. 96, pp. 3147-3176 (1996).

Rubini et al. "Synthesis of Isoteric Methylene-oxy Pseudodipeptide Analogues as Novel Amide Bond Surrogate Units". *Tetrahedron*, vol. 42, No. 21, pp. 6039-6045 (1986).

Mitsubishi Chemical Industries Co., Ltd. "Alkylenedioxybenzene derivatives". CA 100:103390 (1984).

Szporny et al. "Process for production of phenylsulfonylpropionic acid derivatives useful for inhigition of somach acid secretion and pharmaceutical compositions comprising them". CA 123:284907 (1995).

Toldy et al. "Preparation of pyrimidinylpiperazines as lipid peroxidation inhibitors". CA 126:343579 (2004).

Faull et al. "Preparation of aminoheterocyclic derivatives as antithrombotic or anticoagulant agents". CA 125:114690 (1996).

Kubo et al. "Preparation of hydrocarbyl sulfone derivatives as inhibitors of activated blood coagulation factor X and process for their production". CA 136:134784 (2002).

Kubo et al. "Preparation of imidazopyridine derivatives as activated blood coagulation factor X inhibitors for treatment of thrombosis". CA 140:375175 (2004).

Kubo et al. "Preparation and imidazoles and their use as coagulation factor Xa inhibitors". CA 144:128976 (2006).

Kubo et al. "Preparation of heterocyclic amides as activated blood coagulation factor X inhibitors for use as antithrombotic agents". CA 144:22941 (2005).

Faull et al. Preparation of aminoheterocyclic derivatives as antithrombotic or anticoagulant agents. CA 125:114690 (1996).

Patani et al. Bioisosterism: A Rational Approach in Drug Design, 1996, Chemical Review, 96, 3147-3176.

Wolff, Manfred E. "Burger's Medicinal Chemistry, 5ed, Part I". John Wiley & Sons, 1995, pp. 975-977.

Banker (Modern Pharmaceuticals) Banker, G.S. et al. "Modern Pharmaceuticals 3ed.", Marcel Dekker, New York, 1996, pp. 451 and 596.

* cited by examiner

US 7,745,623 B2

CYCLIC AMIDE DERIVATIVE, AND ITS PRODUCTION AND USE

TECHNICAL FIELD

The present invention relates to a novel cyclic amide derivative which inhibits activated blood coagulation factor X (FXa) to exhibit anticoagulant activity and antithrombotic activity, and therefore is useful for preventing and treating arterial and venous thrombotic obstructive diseases, inflammation, cancer and the like; and its production process and use.

BACKGROUND ART

It is important to suppress the formation of thrombi for preventing and treating myocardial infarction, cerebral thrombosis and the like, and various antithrombin agents, platelet aggregation inhibitors and the like have been studied and developed as thrombosis inhibitors. However, since not only platelet aggregation inhibitors, but also anti-thrombin agents suppress the aggregation of platelets in addition to their anticoagulant activity, these medicaments tend to cause bleeding and the like as adverse side-effects. Therefore, there is a problem in their safety. On the other hand, it is considered that the FXa inhibitor is a safe anticoagulant agent for specifically inhibiting only coagulating factor. Hitherto, compounds having the FXa inhibiting activity have been disclosed, for example, in the following publications.

JP 7-112970 A, JP 5-208946 A, WO 96/16940, WO 96/40679, WO 96/10022, WO 97/21437, WO 99/26919, WO 99/33805, WO 00/09480, WO 01/44172, WO 02/06234, US 2002/0045616 A, WO 2003/010160, WO 2003/039543, WO 2003/026652, WO 2004/002477, US 2004/0006062, US 2004/0077635 A and Journal of Medicinal Chemistry, 1998, Vol. 41, page 53-62.

DISCLOSURE OF THE INVENTION

It has been desired to develop a novel compound useful for treating thrombosis, which has improved drug efficacy, oral absorbability and duration of action and has fewer side effects in comparison with previous FXa inhibitors.

The present inventors have intensively studied considering that a cyclic amide derivative having high selectivity for and potent inhibitory activity on FXa can exert lasting and sufficient effect by oral administration and therefore it may be useful for preventing and treating arterial and venous thrombotic obstructive disease, inflammation, cancer and the like.

As a result, the present inventors have found that a novel cyclic amide derivative represented by the formula (I) hereinafter or a salt thereof (hereinafter referred to as the compound (I) in some cases) has selective and potent FXa inhibiting activity and high safety and exerts lasting and sufficient effect by oral administration. Thus, the present invention has been completed.

That is, the present invention relates to:

(1) A compound represented by the formula (I):

$$R^1-W-S(O)_a-X^1-Y^1-A-X^2-N \begin{array}{c} Y^2-Z^1 \\ \diagdown \\ Z^2 \\ \diagup \\ Z^3-X^3 \end{array} \quad (I)$$

wherein $R^1$ represents a cyclic hydrocarbon group which may be optionally substituted or a heterocyclic group which may be optionally substituted, W represents a bond or a divalent chain hydrocarbon group which may be optionally substituted, a represents 0, 1, or 2, $X^1$ represents a lower alkylene which may be optionally substituted or a lower alkenylene which may be optionally substituted, $Y^1$ represents $—C(O)—$, $—S(O)—$ or $—S(O)_2—$, A represents a piperazine ring which may be further substituted or a piperidine ring which may be further substituted, $X^2$ represents a bond or a lower alkylene which may be optionally substituted, $Y^2$ represents $—C(O)—$, $—S(O)—$, $—S(O)_2—$ or $—C(=NR^7)—$ (wherein $R^7$ represents a hydrogen atom, a hydroxy group which may be optionally substituted, a lower alkoxycarbonyl group or an acyl group), $X^3$ represents a $C_{1-4}$ alkylene which may be optionally substituted or a $C_{2-4}$ alkenylene which may be optionally substituted, in which two alkyl groups may be bound to each other to form an aryl ring together with carbon atoms which they attach to when $X^3$ represents a $C_{2-4}$ alkenylene substituted with two alkyl groups, $Z^3$ represents $—N(R^4)—$, $—O—$ or a bond (wherein $R^4$ represents a hydrogen atom, a hydrocarbon group which may be optionally substituted or an acyl group), ===== represents a single bond or a double bond, when ===== represents a single bond, $Z^1$ represents $—C(R^2)(R^{2'})—$, $—N(R^2)—$ or $—O—$, and $Z^2$ represents $—C(R^3)(R^{3'})—$, $—N(R^3)—$, $—O—$ or a bond (provided that, when $Z^1$ is $—O—$, $Z^2$ is other than $—O—$), and when ===== is a double bond, $Z^1$ represents $—C(R^2)=$ or a nitrogen atom, and $Z^2$ represents $=C(R^3)—$ or a nitrogen atom, each of $R^2$, $R^{2'}$, $R^3$ and $R^{3'}$ represents a hydrogen atom, a hydrocarbon group which may be optionally substituted or a heterocyclic group which may be optionally substituted, respectively, or each pair of $R^2$ and $R^3$, and $R^{2'}$ and $R^{3'}$ may be bound to each other respectively to form a ring which may be optionally substituted, or a salt thereof;

(2) The compound according to the above (1), wherein $X^3$ represents a $C_{1-4}$ alkylene which may be optionally substituted or a $C_{2-4}$ alkenylene which may be optionally substituted;

(3) A prodrug of the compound according to the above (1) or (2);

(4) The compound according to the above (2), wherein $R^1$ is an aryl which may be optionally substituted;

(5) The compound according to the above (2), wherein $R^1$ is a naphthyl which may be substituted with a halogen atom;

(6) The compound according to the above (2), wherein W is a bond;

(7) The compound according to the above (2), wherein $Y^1$ is $—C(O)—$;

(8) The compound according to the above (2), wherein $—X^1—Y^1—$ is represented by the formula:

$$—CH_2—CH_2—\overset{O}{\overset{\|}{C}}— \quad \text{or} \quad —CH_2—\underset{OH}{\overset{}{\underset{|}{CH}}}—\overset{O}{\overset{\|}{C}}—;$$

(9) The compound according to the above (2), wherein A is a group represented by the formula:

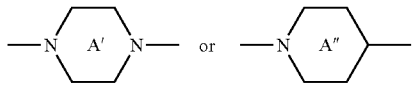

wherein a ring A' represents a piperazine ring which may be further substituted and a ring A" represents a piperidine ring which may be further substituted;

(10) The compound according to the above (2), wherein $X^2$ is a bond;

(11) The compound according to the above (2), wherein $Y^2$ is —C(O)— or —C(=NR$^7$)—;

(12) The compound according to the above (2), wherein

------ is a single bond;

(13) The compound according to the above (2), wherein $Z^3$ is a bond;

(14) The compound according to the above (2), wherein the group:

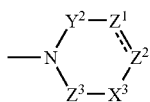

is represented by the formula:

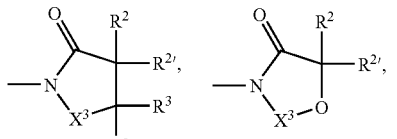

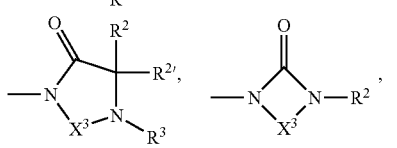

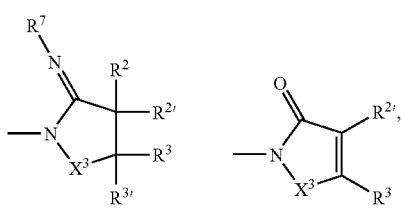

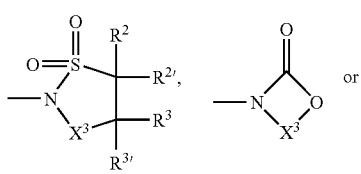

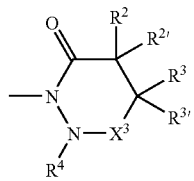

wherein each symbol in the formula is as defined in the above (1);

(15) The compound according to the above (2), wherein the group:

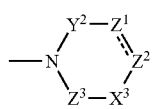

is represented by the formula:

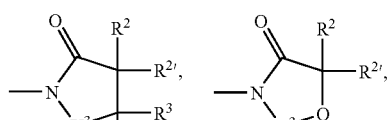

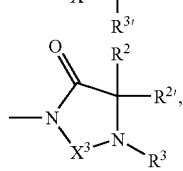

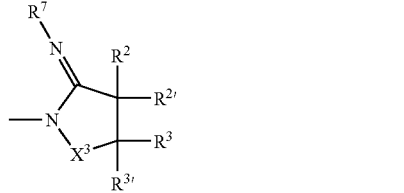

wherein each symbol in the formula is as defined in the above (1);

(16) The compound according to the above (2), wherein a is 2;

(17) The compound according to the above (1) or (2), wherein W is a bond, a is 2, —X$^1$—Y$^1$— is represented by the formula:

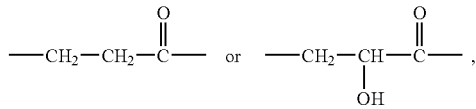

and $X^2$ is a bond;

(18) The compound according to the above (17), wherein $R^1$ is an aryl which may be optionally substituted, and A is a group represented by the formula:

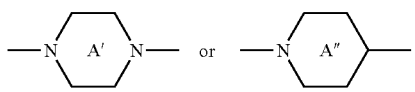

wherein a ring A' represents a piperazine ring which may be further substituted and a ring A" represents a piperidine ring which may be further substituted;

(19) The compound according to the above (18), wherein R¹ is an aryl (preferably, $C_{6-14}$ aryl, more preferably, naphthyl) which may be substituted with 1 to 3 halogen atom(s), $Y^2$ is —C(O)— or —C(=NR⁷)—, ⋯⋯ is a single bond, and $Z^3$ is a bond;

(20) The compound according to the above (19), wherein the group:

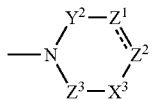

is represented by the formula:

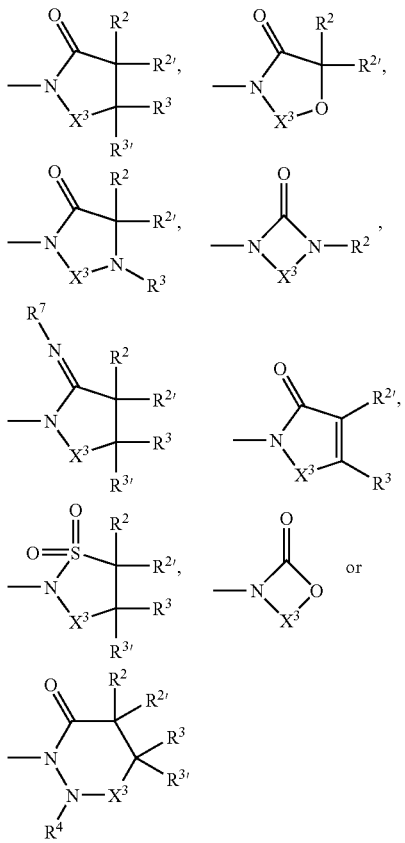

wherein each symbol in the formula is as defined in the above (1);

(21) The compound according to the above (19), wherein the group:

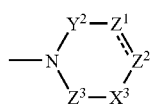

is represented by the formula:

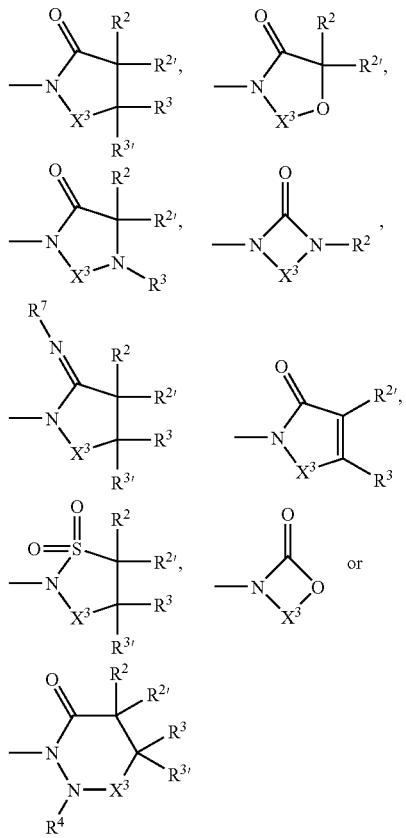

wherein $R^2$, $R^{2'}$, $R^3$ and $R^{3'}$ represents respectively a hydrogen atom, $C_{1-6}$ alkyl which may be optionally substituted with a halogen atom, hydroxy, carbamoyl, N—$C_{1-6}$ alkylcarbamoyl, N,N-di-$C_{1-6}$ alkylcarbamoyl, carboxyl, $C_{1-4}$ alkoxycarbonyl, $C_{1-6}$ alkoxy, amino, mono- or di-$C_{1-6}$ alkylamino, or $C_{1-6}$ alkanoylamino, $R^4$ represents a hydrogen atom, $R^7$ represents a hydrogen atom, $X^3$ represents $C_{1-4}$ alkylene or $C_{2-4}$ alkenylene;

(22) The compound according to the above (21), wherein the group:

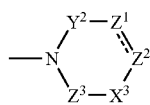

is represented by the formula:

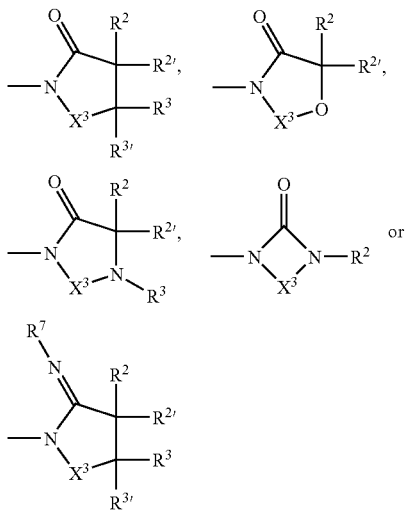

wherein each symbol in the formula is as defined in the above (21);

(22-a) The compound according to the above (21), wherein $R^1$ is a naphthyl which may be substituted with a halogen atom, and the group:

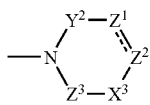

is represented by the formula:

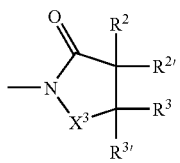

wherein each symbol in the formula is as defined in the above (21);

(22-b) The compound according to the above (21), wherein $R^1$ is a naphthyl which may be substituted with a halogen atom, and the group:

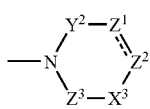

is represented by the formula:

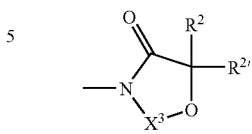

wherein each symbol in the formula is as defined in the above (21);

(22-c) The compound according to the above (21), wherein $R^1$ is a naphthyl which may be substituted with a halogen atom, and the group:

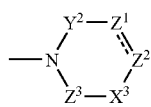

is represented by the formula:

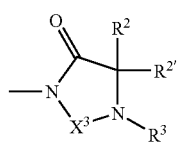

wherein each symbol in the formula is as defined in the above (21);

(22-d) The compound according to the above (21), wherein $R^1$ is a naphthyl which may be substituted with a halogen atom, and the group:

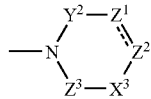

is represented by the formula:

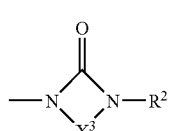

wherein each symbol in the formula is as defined in the above (21);

(22-e) The compound according to the above (21), wherein $R^1$ is a naphthyl which may be substituted with a halogen atom, and the group:

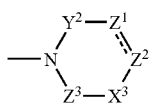

is represented by the formula:

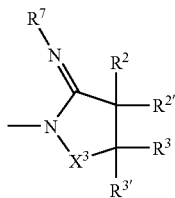

wherein each symbol in the formula is as defined in the above (21);

(23) A compound selected from a group consisting of
4-(1-{(2S)-3-[(6-chloronaphthalen-2-yl)sulfonyl]-2-hydroxypropanoyl}piperidin-4-yl)morpholin-3-one,
1-(4-{(2S)-3-[(6-chloronaphthalen-2-yl)sulfonyl]-2-hydroxypropanoyl}piperazin-1-yl)piperidin-2-one,
1-(1-{(2S)-3-[(6-chloronaphthalen-2-yl)sulfonyl]-2-hydroxypropanoyl}piperidin-4-yl)tetrahydropyrimidin-2(1H)-one,
1-(4-{(2S)-3-[(6-chloronaphthalen-2-yl)sulfonyl]-2-hydroxypropanoyl}piperazin-1-yl)tetrahydropyrimidin-2(1H)-one,
1-(1-{3-[(6-chloronaphthalen-2-yl)sulfonyl]-propanoyl}piperazin-4-yl)tetrahydropyrimidin-2(1H)-one and
(2S)-3-[(6-chloronaphthalen-2-yl)sulfonyl]-1-(2-imino-1,4'-bipiperidin-1'-yl)-1-oxopropan-2-ol, or a salt thereof;

(24) A compound selected from a group consisting of
1'-{(2S)-3-[(6-Chloronaphthalen-2-yl)sulfonyl]-2-hydroxypropanoyl}-1,4'-bipiperidin-2-one, and
2-(1-{(2S)-3-[(6-Chloronaphthalen-2-yl)sulfonyl]-2-hydroxypropanoyl}piperidin-4-yl)isoindolin-1-one.

(25) A pharmaceutical composition comprising the compound according to the above (1), (2) or (3);

(26) The pharmaceutical composition according to the above (25), which is an anticoagulant;

(27) The pharmaceutical composition according to the above (25), which is an activated blood coagulation factor X inhibitor;

(28) The pharmaceutical composition according to the above (25), which is a medicament for preventing or treating myocardial infarction, cerebral infarction, deep vein thrombosis, pulmonary thromboembolism or atherosclerotic obliterans;

(29) The pharmaceutical composition according to the above (25), which is a medicament for preventing or treating economy-class syndrome, thromboembolism during and post operation, or the secondary onset of deep vein thrombosis;

(30) Use of the compound according to the above (1), (2) or (3) for manufacturing an activated blood coagulation factor X inhibitor;

(31) A method for preventing or treating myocardial infarction, cerebral infarction, deep vein thrombosis, pulmonary thromboembolism or atherosclerotic obliterans, which comprises administering the compound according to the above (1), (2) or (3) to a human being or an animal;

(32) A method for preventing or treating economy-class syndrome, thromboembolism during and post operation, or the secondary onset of deep vein thrombosis which comprises administering the compound according to the above (1), (2) or (3) to a human being or an animal; and

(33) A process for preparing the compound according to the above (1), which comprises reacting a compound represented by the formula (II):

wherein L represents a leaving group and the other symbols are as defined in the above (1), or a salt thereof with a compound represented by the formula (III):

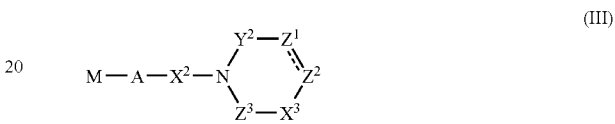

wherein M represents a hydrogen atom, an alkali metal, an alkali earth metal or a leaving group and the other symbols are as defined in the above (1), or a salt thereof, and if necessary, subjecting the resulting compound to hydrolysis, esterification, amidation, alkylation, acylation, reduction, oxidation and/or deprotection reactions.

In the above-mentioned formula, $R^1$ represents a cyclic hydrocarbon group which may be optionally substituted or a heterocyclic group which may be optionally substituted (preferably, an aryl group which may be optionally substituted or an aromatic heterocyclic group which may be optionally substituted).

Examples of the "cyclic hydrocarbon group" in the term of "cyclic hydrocarbon group which may be substituted" include an alicyclic hydrocarbon group, an aryl group and the like, and an aryl group and the like are preferable in particular.

Examples of the "alicyclic hydrocarbon group" of the example of the cyclic hydrocarbon group include saturated or unsaturated alicyclic hydrocarbon groups such as a cycloalkyl group, a cycloalkenyl group and a cycloalkadienyl group.

Herein, examples of the "cycloalkyl group" include $C_{3-9}$ cycloalkyls and the like such as cyclopropyl, cyclobutyl, cyclopentyl, cyclohexyl, cycloheptyl, cyclooctyl and cyclononyl.

Examples of the "cycloalkenyl group" include $C_{3-9}$ cycloalkenyls and the like such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, 1-cyclohexen-1-yl and 1-cyclohepten-1-yl.

Examples of the "cycloalkadienyl group" include $C_{4-6}$ cycloalkadienyl groups and the like such as 2,4-cyclopentadien-1-yl, 2,4-cyclohexadien-1-yl and 2,5-cyclohexadien-1-yl.

Examples of the "aryl group" as the example of the cyclic hydrocarbon group include a monocyclic or condensed polycyclic aromatic hydrocarbon group. Example includes $C_{6-14}$ aryl groups and the like such as phenyl, naphthyl, anthryl, phenanthryl and acenaphthylenyl, and among these, phenyl, 1-naphthyl, 2-naphthyl and the like are preferable in particular.

Further, examples of the cyclic hydrocarbon group include a bicyclic or tricyclic hydrocarbon group which is derived from the condensation of the same or different 2 to 3 rings (preferably, 2 kinds or more of rings) selected from the rings which constitute the above-mentioned alicyclic hydrocarbon group and aromatic hydrocarbon group such as 1,2-dihydronaphthyl, 1,2,3,4-tetrahydronaphthyl, indenyl, dihydrobenzocycloheptenyl, fluorenyl, etc.

Examples of the "heterocyclic group" of the "optionally substituted heterocyclic group" represented by $R^1$ include an aromatic heterocyclic group, a saturated or unsaturated non-aromatic heterocyclic group (aliphatic heterocyclic group) which contains at least one (preferably 1 to 4, and more preferably 1 to 2) of 1 to 3 kinds (preferably 1 to 2 kinds) of hetero atoms which are selected from an oxygen atom, a sulfur atom and a nitrogen atom as a ring system constituting atom (ring atom), and the like.

Examples of the "aromatic heterocyclic group" include 5- to 6-membered mono-cyclic aromatic heterocyclic groups such as furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and 8- to 16-membered (preferably 8- to 12-membered) aromatic condensed heterocyclic groups
such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, benzopyranyl (for example, 2H-chromen-3-yl), 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo-[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl, and the like, preferably, a heterocyclic ring in which 1 to 2 (preferably 1) of the above-mentioned 5- to 6-membered mono-cyclic aromatic heterocyclic group(s) are condensed with 1 to 2 (preferably 1) of benzene ring(s), or a heterocyclic ring in which 2 to 3 (preferably 2) of the same or different above-mentioned 5- to 6-membered mono-cyclic aromatic heterocyclic groups are condensed,
more preferably, a heterocyclic ring in which the above-mentioned 5- to 6-membered mono-cyclic aromatic heterocyclic group is condensed with a benzene ring, and preferably in particular indolyl, benzofuranyl, benzo[b]thienyl and benzopyranyl.

Examples of the "non-aromatic heterocyclic group" include 3- to 8-membered (preferably 5- to 6-membered) saturated or unsaturated (preferably saturated) non-aromatic heterocyclic groups (aliphatic mono-cyclic heterocyclic group) such as oxiranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl; a heterocyclic group in which 1 to 2 (preferably 1) of the above-mentioned mono-cyclic non-aromatic heterocyclic group(s) are condensed with 1 to 2 (preferably 1) of benzene ring(s) such as 1,3-dihydroisoindolyl; a heterocyclic group in which 1 to 2 (preferably 1) of the above-mentioned mono-cyclic nonaromatic heterocyclic group(s) are condensed with 1 to 2 (preferably 1) of the above-mentioned 5- to 6-membered mono-cyclic aromatic heterocyclic group(s); or a non-aromatic heterocyclic group in which a part or all of the double bonds of the above-mentioned mono-cyclic aromatic heterocyclic groups or aromatic condensed heterocyclic groups is saturated, such as 1,2,3,4-tetrahydroquinolyl 1,2,3,4-tetrahydroisoquinolyl, or the like.

Examples of the substituent of the "cyclic hydrocarbon group which may be optionally substituted" and the "heterocyclic group which may be optionally substituted" represented by $R^1$ include alkyl which may be optionally substituted, alkenyl which may be optionally substituted, alkynyl which may be optionally substituted, aryl which may be optionally substituted, cycloalkyl which may be optionally substituted, cycloalkenyl which may be optionally substituted, a heterocyclic group which may be optionally substituted, amino which may be optionally substituted, imidoyl which may be optionally substituted (for example, a group represented by the formula —C(U')=N—U (wherein each of U and U' represents a hydrogen atom or a substituent (U represents preferably a hydrogen atom)), and the like), amidino which may be optionally substituted (for example, a group represented by the formula —C(NT'T")=N-T (wherein each of T, T' and T" represents a hydrogen atom or a substituent (T represents preferably a hydrogen atom)), and the like), a hydroxy group which may be optionally substituted, a thiol group which may be optionally substituted, carboxyl which may be optionally esterified, carbamoyl which may be optionally substituted, thiocarbamoyl which may be optionally substituted, a sulfamoyl group which may be optionally substituted, a halogen atom (for example, fluorine, chlorine, bromine and iodine, and preferably chlorine, bromine and the like), a cyano group, a nitro group, acyl and the like. These optional substituents may be at 1 to 5 (preferably 1 to 3) substitutable positions. The "cyclic hydrocarbon group which may be optionally substituted" and the "heterocyclic group which may be optionally substituted" represented by $R^1$ may optionally have an oxo group or a thioxo group, and for example, when R is benzopyranyl, R may form benzo-α-pyronyl, benzo-γ-pyronyl and the like.

Examples of "aryl" in the "aryl which may be optionally substituted" as the substituent in the "cyclic hydrocarbon group which may be optionally substituted" and the "heterocyclic group which may be optionally substituted" represented by $R^1$ include $C_{6-14}$ aryl such as phenyl, naphthyl, anthryl, phenanthryl and acenaphthylenyl. Herein, the substituent of aryl includes a lower alkoxy group (for example, $C_{1-6}$ alkoxy such as methoxy, ethoxy and propoxy), a halogen atom (for example, fluorine, chlorine, bromine and iodine, and the like), lower alkyl (for example, $C_{1-6}$ alkyl such as methyl, ethyl and propyl), lower alkenyl (for example, $C_{2-6}$ alkenyl such as vinyl and allyl), lower alkynyl (for example, $C_{2-6}$ alkynyl such as ethynyl and propargyl), amino which may be optionally substituted, a hydroxy group which may be optionally substituted, a cyano group, amidino which may be optionally substituted, carboxy, a lower alkoxy carbonyl group (for example, $C_{1-6}$ alkoxycarbonyl such as methoxycarbonyl and ethoxycarbonyl), a carbamoyl group which may be optionally substituted [for example, a carbamoyl group which may be optionally substituted with $C_{-1-6}$ alkyl which may be optionally substituted with a 5- to 6-membered mono-cyclic aromatic heterocyclic group (for example, pyridinyl and the like), acyl (for example, formyl, $C_{2-6}$ alkanoyl, benzoyl, $C_{1-6}$ alkylsulfonyl which may be optionally halogenated, benzenesulfonyl and the like), or $C_{1-6}$ alkoxycarbonyl which may be optionally halogenated; 1-azetidinylcarbonyl, 1-pyrrolidinylcarbonyl, piperidinocarbonyl, morpholinocarbonyl, thiomorpholinocarbonyl (a sulfur atom may be optionally oxidized), 1-piperazinylcarbonyl, and the like], and the like. These optional substituents may be at 1 to 3 substitutable positions.

Examples of "amino which may be optionally substituted", "a hydroxy group which may be optionally substituted" and "amidino which may be optionally substituted" as the substituent in the "aryl which may be optionally substituted" as the substituent in the "cyclic hydrocarbon group which may be optionally substituted" and the "heterocyclic group which may be optionally substituted" represented by $R^1$ include the same groups as those exemplified for "amino which may be optionally substituted", "a hydroxy group which may be optionally substituted" and "amidino which may be optionally substituted" as the substituent in the terms of "cyclic hydrocarbon group which may be optionally substituted" and the "heterocyclic group which may be optionally substituted" represented by $R^1$ as described hereinafter.

Examples of the "alkyl" in the term of "alkyl which may be optionally substituted" as the substituent in the terms of "cyclic hydrocarbon group which may be optionally substituted" and "heterocyclic group which may be optionally substituted" represented by $R^1$ include $C_{1-6}$ alkyl such as methyl, ethyl, n-propyl, isopropyl, n-butyl, isobutyl, tert-butyl, n-pentyl, isopentyl, neopentyl, 1-methylpropyl, n-hexyl, iso-hexyl, 1,1-dimethylbutyl, 2,2-dimethylbutyl, 3,3-dimethylbutyl, or the like. Herein, the substituent of alkyl includes the same number of the same groups as those exemplified for the substituent in the term of above-mentioned "aryl which may be optionally substituted", and an oxo group, a thioxo group and the like.

Examples of the "alkenyl" in the term of "alkenyl which may be optionally substituted" as the substituent in the terms of "cyclic hydrocarbon group which may be optionally substituted" and "heterocyclic group which may be optionally substituted" represented by $R^1$ include $C_{2-6}$ alkenyl such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl, and the like. Herein, the substituent of alkenyl includes the same number of the same groups as those exemplified for the substituent in the term of above-mentioned "aryl which may be optionally substituted", and an oxo group, a thioxo group and the like.

Examples of the "alkynyl" in the term of "alkynyl which may be optionally substituted" as the substituent in the terms of "cyclic hydrocarbon group which may be optionally substituted" and the "heterocyclic group which may be optionally substituted" represented by $R^1$ include $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. Herein, the substituent of alkynyl includes the same number of the same groups as those exemplified for the substituent in the term of the above-mentioned "aryl which may be optionally substituted", and an oxo group, a thioxo group and the like.

Examples of the "cycloalkyl" in the term of "cycloalkyl which may be optionally substituted" as the substituent in the terms of "cyclic hydrocarbon group which may be optionally substituted" and the "heterocyclic group which may be optionally substituted" represented by $R^1$ include $C_{3-7}$ cycloalkyl such as cyclopropyl, cyclobutyl, cyclopentyl, cyclohexyl and cycloheptyl, and the like. Herein, the substituent in the term of cycloalkyl includes the same number of the same groups as those exemplified for the substituent in the term of above-mentioned "aryl which may be optionally substituted" and an oxo group, a thioxo group and the like.

Examples of the "cycloalkenyl" in the term of "cycloalkenyl which may be optionally substituted" as the substituent in the terms of "cyclic hydrocarbon group which may be optionally substituted" and the "heterocyclic group which may be optionally substituted" represented by $R^1$ include $C_{3-6}$ cycloalkenyl such as cyclopropenyl, cyclobutenyl, cyclopentenyl and cyclohexenyl, and the like. Herein, the substituent in the term of cycloalkenyl which may be optionally substituted includes the same number of the same groups as those exemplified for the substituent in the term of the above-mentioned "aryl which may be optionally substituted", and an oxo group, a thioxo group and the like.

As the "heterocyclic group" in the term of "heterocyclic group which may be optionally substituted" as the substituent in the terms of "cyclic hydrocarbon group which may be optionally substituted" and the "heterocyclic group which may be optionally substituted" represented by $R^1$, the same groups as those exemplified for the heterocyclic group in the term of "optionally substituted heterocyclic group" represented by $R^1$ is exemplified.

Further, the substituent of the heterocyclic group in the term of "heterocyclic group which may be optionally substituted" includes the same number of the same groups as those exemplified for the substituent in the term of the above-mentioned "aryl which may be optionally substituted", and an oxo group, a thioxo group and the like.

Examples of the "substituent" in the terms of "amino which may be optionally substituted", "imidoyl which may be optionally substituted", "amidino which may be optionally substituted", "a hydroxy group which may be optionally substituted" and "a thiol group which may be optionally substituted" as the substituent in the "cyclic hydrocarbon group which may be optionally substituted" and the "heterocyclic group which may be optionally substituted" represented by $R^1$ include (1) a lower alkyl (for example, $C_{1-6}$ alkyl such as methyl, ethyl, propyl, isopropyl, butyl, isobutyl, tert-butyl, pentyl, and hexyl and the like) which may be optionally substituted with a substituent selected from a halogen atom (for example, fluorine, chlorine, bromine and iodine, and the like) and $C_{1-6}$ alkoxy which may be optionally halogenated (for example, methoxy, ethoxy, trifluoromethoxy, 2,2,2-trifluoroethoxy, trichloromethoxy, 2,2,2-trichloroethoxy and the like), (2) acyl such as $C_{1-6}$ alkanoyl (for example, formyl, acetyl, propionyl, valeroyl and pivaloyl), benzoyl, $C_{1-6}$ alkylsulfonyl (for example, methanesulfonyl and the like), benzenesulfonyl; said acyl may be optionally substituted with 1) amino which may be optionally substituted with a substituent selected from $C_{1-6}$ lower alkyl (for example, methyl, ethyl, butyl, isopropyl, cyclopropyl, cyclohexyl and the like), $C_{1-10}$ acyl (for example, acetyl, propionyl, isopropionyl, benzoyl, p-chlorobenzoyl, 4-methylbenzoyl and the like) and methanesulfonyl, 2) 2-oxo-1-pyrrolidinyl, 3) 2-oxo-1-piperidinyl, 4) 1-acetyl-4-piperidinyl, 5) 1-propionyl-4-piperidinyl and the like (for example, 2-aminopropionyl, 2-benzoylaminopropionyl, 2-(2-oxo-1-pyrrolidinyl)propionyl, 2-(2-oxo-1-piperidinyl)propionyl, 2-(1-acetyl-4-piperidinyl)propionyl, and the like), (3) $C_{1-6}$ alkoxycarbonyl which may be optionally halogenated (for example, methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl and the like), $C_{1-6}$ alkoxycarbonyl which may be optionally substituted with phenyl (for example, benzyloxycarbonyl and the like), (4) a heterocyclic group (the same groups as those exemplified for the "heterocyclic group" in the term of "heterocyclic group which may be optionally substituted" represented by $R^1$, and the like), and the like. The "amino" in the term of "amino which may be optionally substituted" as a substituent may be substituted with imidoyl which may be optionally substituted (for example, $C_{1-6}$ alkanoylimidoyl (for example, formylimidoyl, acetylimidoyl and the like), $C_{1-6}$ alkoxyimidoyl, $C_{1-6}$ alkylthioimidoyl, amidino and the like), amino which may be optionally substituted with 1 to 2 of $C_{1-6}$ alkyl and the like. Further, two substituents may be also combined with a nitrogen atom to occasionally form cyclic amino. Examples of the cyclic amino in this case include 3- to 8-membered (preferably 5- to 6-membered) cyclic amino such as 1-azetidinyl, 1-pyrrolidinyl, piperidino, thiomorpholino, morpholino, 1-piperazinyl and 1-piperazinyl which may optionally have lower alkyl (for example, $C_{1-6}$ alkyl such as methyl, ethyl, propyl, isopropyl, butyl, tert-butyl, pentyl and hexyl, and the like), aralkyl (for example, $C_{7-10}$ aralkyl such as benzyl and phenethyl, and the like), aryl (for example, $C_{6-10}$ aryl such as phenyl, 1-naphthyl and 2-naphthyl, and the like) and the like at its 4-position, 1-pyrrolyl, 1-imidazolyl and the like.

Examples of "carboxyl which may be optionally esterified" as the substituent in the terms of "cyclic hydrocarbon group which may be optionally substituted" and the "heterocyclic group which may be optionally substituted" represented by $R^1$ include lower alkoxycarbonyl, aryloxycarbonyl, aralkylcarbonyl and the like in addition to free carboxyl.

Examples of the "lower alkoxycarbonyl" include $C_{1-6}$ alkoxycarbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl and neopentyloxycarbonyl, and among these, $C_{1-3}$ alkoxycarbonyl such as methoxycarbonyl, ethoxycarbonyl and propoxycarbonyl, and the like are preferable.

As examples of the "aryloxycarbonyl", $C_{7-12}$ aryloxycarbonyl such as phenoxycarbonyl, 1-naphthoxycarbonyl and 2-naphthoxycarbonyl, and the like are preferable.

Further, as examples of the "aralkyloxycarbonyl", $C_{7-10}$ aralkyloxycarbonyl such as benzyloxycarbonyl and phenethyloxycarbonyl, and the like are preferable (preferably, $C_{6-10}$ aryl-$C_{1-4}$ alkoxy-carbonyl and the like).

The "aryloxycarbonyl" and "aralkyloxycarbonyl" may optionally be substituted, and as the substituents, the same number of the same groups as those exemplified for the substituent of aryl and aralkyl exemplified as examples of the substituent of N-mono-substituted carbamoyl described hereinafter can be used.

Examples of "carbamoyl which may be optionally substituted" as the substituent in the terms of "cyclic hydrocarbon group which may be optionally substituted" and the "heterocyclic group which may be optionally substituted" represented by $R^1$ include N-mono-substituted carbamoyl and N,N-di-substituted carbamoyl in addition to unsubstituted carbamoyl.

Examples of the substituent of the "N-mono-substituted carbamoyl" include lower alkyl (for example, $C_{1-6}$ alkyl such as methyl, ethyl, propyl, isopropyl, butyl, isobutyl, tert-butyl, pentyl and hexyl, and the like), lower alkenyl (for example, $C_{2-6}$ alkenyl such as vinyl, allyl, isopropenyl, propenyl, butenyl, pentenyl, and hexenyl, and the like), cycloalkyl (for example, $C_{3-6}$ cycloalkyl such as cyclopropyl, cyclobutyl, cyclopentyl and cyclohexyl, and the like), aryl (for example, $C_{6-10}$ aryl such as phenyl, 1-naphthyl and 2-naphthyl, and the like), aralkyl (for example, $C_{7-10}$ aralkyl such as benzyl and phenethyl, preferably phenyl-$C_{1-4}$ alkyl and the like), arylalkenyl (for example, $C_{8-10}$ arylalkenyl such as cinnamyl, and preferably, phenyl-$C_{2-4}$ alkenyl, and the like), a heterocyclic group (for example, the same groups as those exemplified for the "heterocyclic group" in the term of "optionally substituted heterocyclic group" represented by the above-mentioned $R^1$, and the like), amino which may be optionally substituted with 1 to 2 of $C_{1-6}$ alkyl(s), and the like. The lower alkyl, lower alkenyl, cycloalkyl, aryl, aralkyl, arylalkenyl and heterocyclic group may optionally have a substituent, and examples of the substituent include a hydroxy group, amino which may be optionally substituted (the amino may optionally have, for example, 1 or 2 of lower alkyl(s) (for example, $C_{1-6}$ alkyl such as methyl, ethyl, propyl, isopropyl, butyl, isobutyl, tert-butyl, pentyl and hexyl, and the like), acyl (for example, $C_{1-6}$ alkanoyl such as formyl, acetyl, propionyl and pivaloyl, and benzoyl and the like), carboxyl, $C_{1-6}$ alkoxycarbonyl and the like as a substituent), a halogen atom (for example, fluorine, chlorine, bromine and iodine, and the like), a nitro group, a cyano group, lower alkyl which may be optionally substituted with 1 to 5 of halogen atoms (for example, fluorine, chlorine, bromine, iodine, and the like), lower alkoxy which may be optionally substituted with 1 to 5 of halogen atom(s) (for example, fluorine, chlorine, bromine, iodine, and the like), and the like. Examples of the lower alkyl include $C_{1-6}$ alkyl such as methyl, ethyl, n-propyl, isopropyl, n-butyl, isobutyl, sec-butyl, tert-butyl, pentyl and hexyl, and the like, and in particular, methyl and ethyl are preferable. Examples of the lower alkoxy include $C_{1-6}$ alkoxy such as methoxy, ethoxy, n-propoxy, isopropoxy, n-butoxy, isobutoxy, sec-butoxy and tert-butoxy), and the like, and in particular, methoxy and ethoxy are preferable. Further, there are 1 or 2 to 3 (preferably 1 or 2) of the substituent(s), the same or different, preferably.

The "N,N-di-substituted carbamoyl" means a carbamoyl group which has 2 substituents on the nitrogen atom. Examples of one of the substituents include the same groups as those exemplified for the substituent in the term of above-mentioned "N-mono-substituted carbamoyl", and examples of another of the substituents include lower alkyl (for example, $C_{1-6}$ alkyl such as methyl, ethyl, propyl, isopropyl, butyl, tert-butyl, pentyl and hexyl, and the like), $C_{3-6}$ cycloalkyl (for example, cyclopropyl, cyclobutyl, cyclopentyl, cyclohexyl, and the like), $C_{7-10}$ aralkyl (for example, benzyl, phenethyl and the like, and preferably phenyl-$C_{1-4}$ alkyl), and the like. Further, 2 substituents may be occasionally combined with the nitrogen atom to form cyclic amino, and examples of the cyclic aminocarbamoyl in such a case include 3- to 8-membered (preferably 5- to 6-membered) cyclic aminocarbonyl such as 1-azetidinylcarbonyl, 1-pyrrolidinylcarbonyl, piperidinocarbonyl, morpholinocarbonyl, thiomorpholinocarbonyl (a sulfur atom may be optionally oxidized), 1-piperazinylcarbonyl, and 1-piperazinylcarbonyl which may optionally have lower alkyl (for example, $C_{1-6}$ alkyl such as methyl, ethyl, propyl, isopropyl, butyl, tert-butyl, pentyl and hexyl, and the like), aralkyl (for example, $C_{7-10}$ aralkyl such as benzyl and phenethyl, and the like), aryl (for example, $C_{6-10}$ aryl such as phenyl, 1-naphthyl and 2-naphthyl, and the like), at its 4-position.

As the substituent in the terms of "thiocarbamoyl which may be optionally substituted" and the "sulfamoyl which may be optionally substituted" as the substituent in the terms of "cyclic hydrocarbon group which may be optionally substituted" and the "heterocyclic group which may be optionally substituted" represented by $R^1$, the same groups as those exemplified for the substituent in the term of the above-mentioned "carbamoyl which may be optionally substituted" are exemplified.

Examples of "acyl" as the substituent in the terms of "cyclic hydrocarbon group which may be optionally substituted" and the "heterocyclic group which may be optionally substituted" represented by $R^1$ include acyl derived from carboxylic acid, acyl derived from sulfinic acid, acyl derived from sulfonic acid and acyl derived from phosphonic acid, and the like.

As the "acyl derived from carboxylic acid", groups obtained by binding carbonyl (—C(O)—) with a hydrogen atom or one substituent which the above-mentioned "N-mono-substituted carbamoyl" has on its nitrogen atom are exemplified, and examples include formyl; chain or cyclic $C_{2-8}$ alkanoyl which may be optionally halogenated such as acetyl, propionyl, butyryl, isobutyryl, valeryl, isovaleryl, pivaloyl, hexanoyl, cyclobutanecarbonyl, cyclopetanecarbonyl, cyclohexanecarbonyl, crotonyl and trifluoroacetyl; benzoyl, nicotinoyl, isonicotinoyl and the like, and among them, $C_{2-5}$ alkanoyl such as acetyl, propionyl, butyryl, valeryl or pivaloyl is preferable.

As the "acyl derived from sulfinic acid", groups obtained by binding sulfinyl (—S(O)—) with one substituent which the above-mentioned "N-mono-substituted carbamoyl" has on its nitrogen atom are exemplified, and examples include chain or cyclic $C_{1-6}$ alkylsulfinyl which may be optionally halogenated such as methanesulfinyl, ethanesulfinyl, propanesulfinyl, cyclopropanesulfinyl, cyclopentanesulfinyl, cyclohexanesulfinyl or the like; benzenesulfinyl, tolenesulfinyl and the like.

As the "acyl derived from sulfonic acid", groups obtained by binding sulfonyl (—S(O)$_2$—) with one substituent which the above-mentioned "N-mono-substituted carbamoyl" has on its nitrogen atom are exemplified, and examples include chain or cyclic $C_{1-6}$ alkylsulfonyl which may be optionally halogenated such as methanesulfonyl, ethanesulfonyl, propanesulfonyl, cyclopropanesulfonyl, cyclopentanesulfonyl, cyclohexanesulfonyl or the like; benzenesulfonyl, toluenesulfonyl and the like.

Examples of the "acyl derived from phosphonic acid" include (mono- or di-$C_{1-4}$ alkyl)phosphono which may optionally form a ring, such as dimethylphosphono, diethylphosphono, diisopropylphosphono, dibutylphosphono and 2-oxido-1,3,2-dioxaphosphinan-2-yl, or the like.

$R^1$ is preferably an aryl group which may be optionally substituted with a substituent selected from a halogen atom, $C_{1-6}$ alkyl, $C_{2-6}$ alkenyl, $C_{2-6}$ alkynyl, amino which may be optionally substituted, nitro, cyano, amidino which may be optionally substituted, and carboxyl which may be optionally esterified or amidated; or a heterocyclic group which may be optionally substituted with a substituent selected from a halogen atom, $C_{1-6}$ alkyl, $C_{2-6}$ alkenyl, $C_{2-6}$ alkynyl, amino which may be optionally substituted, nitro, cyano, amidino which may be optionally substituted, and carboxyl which may be optionally esterified or amidated.

Among these, $R^1$ is preferably aryl which may be optionally substituted, and in particular, aryl (preferably $C_{6-14}$ aryl such as phenyl, 1-naphthyl and 2-naphthyl, and the like) which may be optionally substituted with a halogen atom or $C_{2-4}$ alkenyl (preferably a halogen atom) is preferable.

Further, $R^1$ is preferably a heterocyclic group which may be optionally substituted, and in particular, a heterocyclic group (preferably indolyl, benzofuranyl, 2H-chromen-3-yl, further preferably indolyl) which may be optionally substituted with a halogen atom is preferable.

In particular, $R^1$ is preferably naphthyl which may be optionally substituted with a halogen atom.

In the above-mentioned formula, W represents a bond or a divalent chain hydrocarbon group which may be optionally substituted.

Examples of the "divalent chain hydrocarbon group" in the "divalent chain hydrocarbon group which may be optionally substituted" represented by W include $C_{1-6}$ alkylene (for example, methylene, ethylene, trimethylene, tetramethylene, and the like), $C_{2-6}$ alkenylene (for example, vinylene, propylene, 1- or 2-butenylene, butadienylene and the like) and $C_{2-8}$ alkynylene (for example, ethynylene, 1- or 2-propynylene, 1- or 2-butynylene and the like), and the like.

Examples of the substituent in the "divalent chain hydrocarbon group which may be optionally substituted" represented by W include the same groups as those exemplified for the substituent in the term of the above-mentioned "cyclic hydrocarbon group which may be optionally substituted" represented by $R^1$, and the like.

Example of W is preferably a bond or $C_{2-6}$ alkenylene, and among these, a bond is more preferable.

In the above-mentioned formula, $Y^1$ represents —C(O)—, —S(O)— or —S(O)$_2$— (preferably —C(O)—).

In the above-mentioned formula, $X^1$ represents a lower alkylene which may be optionally substituted or a lower alkenylene which may be optionally substituted.

Examples of the "lower alkylene" in the term of "lower alkylene which may be optionally substituted" represented by $X^1$ include $C_{1-6}$ alkylene such as methylene, ethylene, trimethylene and tetramethylene, and the like.

Examples of the "lower alkenylene" in the term of "lower alkenylene which may be optionally substituted" represented by $X^1$ include $C_{2-6}$ alkenylene such as vinylene, propylene, 1- or 2-butenylene and butadienylene, and the like.

Examples of the "substituent" in the terms of "lower alkylene which may be optionally substituted" and the "lower alkenylene which may be optionally substituted" represented by $X^1$ include the same groups as those exemplified for the substituent in the term of the above-mentioned "cyclic hydrocarbon group which may be optionally substituted" represented by $R^1$, and the like, and are preferably lower alkyl (for example, $C_{1-6}$ alkyl such as methyl, ethyl, propyl and the like), lower alkenyl (for example, $C_{2-6}$ alkenyl such as vinyl, allyl and the like), lower alkynyl (for example, $C_{2-6}$ alkynyl such as ethynyl and propargyl, and the like), amino which may be optionally substituted, a hydroxy group which may be optionally substituted, carboxy, a lower alkoxy carbonyl group (for example, $C_{1-6}$ alkoxycarbonyl such as methoxycarbonyl and ethoxycarbonyl, and the like), a carbamoyl group which may be optionally substituted (for example, a carbamoyl group which may be optionally substituted with $C_{1-6}$ alkyl or acyl (for example, formyl, $C_{2-6}$ alkanoyl, benzoyl, $C_{1-6}$ alkoxycarbonyl which may be optionally halogenated, $C_{1-6}$ alkylsulfonyl which may be optionally halogenated, benzenesulfonyl, p-toluenesulfonyl and the like), or an oxo group. 1 to 3 of these substituents may be at optional position(s) which can be substituted.

$X^1$ is preferably $C_{1-6}$ alkylene which may be optionally substituted with a hydroxy group, and among these, ethylene which may be optionally substituted with a hydroxy group (for example, a divalent group represented by the formula:

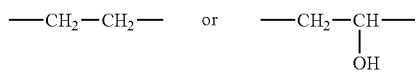

and the like are preferable in particular.

In the above-mentioned formula, —X¹—Y¹— is preferably in particular:

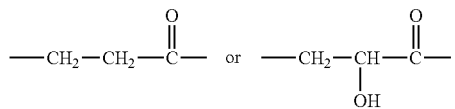

and the like.

In the above-mentioned formula, $X^2$ represents a bond or a lower alkylene which may be optionally substituted.

Examples of the "lower alkylene" in the term of "lower alkylene which may be optionally substituted" represented in $X^2$ include $C_{1-6}$ alkylene such as methylene, ethylene, trimethylene and tetramethylene, and the like.

Examples of the "substituent" in the term of "lower alkylene which may be optionally substituted" represented by $X^2$ include the same groups as those exemplified for the substituent in the term of the above-mentioned "cyclic hydrocarbon group which may be optionally substituted" represented by $R^1$, and the like. Among these, preferable examples may be lower alkyl (for example, $C_{1-6}$ alkyl such as methyl, ethyl, propyl and the like), lower alkenyl (for example, $C_{2-6}$ alkenyl such as vinyl, allyl and the like), lower alkynyl (for example, $C_{2-6}$ alkynyl such as ethynyl and propargyl, and the like), amino which may be optionally substituted, a hydroxy group which may be optionally substituted, carboxy, a lower alkoxycarbonyl group (for example, $C_{1-6}$ alkoxycarbonyl such as methoxycarbonyl and ethoxycarbonyl, and the like), a carbamoyl group which may be optionally substituted (for example, a carbamoyl group which may be optionally substituted with $C_{1-6}$ alkyl or acyl (for example, formyl, $C_{2-6}$ alkanoyl, benzoyl, $C_{1-6}$ alkoxycarbonyl which may be optionally halogenated, $C_{1-6}$ alkylsulfonyl which may be optionally halogenated, benzenesulfonyl, p-toluenesulfonyl and the like), or an oxo group, and the like. 1 to 3 of these substituents may be at optional substitutable position(s).

$X^2$ is preferably a bond.

In the above-mentioned formula, A represents a piperazine ring which may be further substituted or a piperidine ring which may be further substituted [preferably, the formula:

(wherein the ring A' represents a piperazine ring which may be further substituted), or the formula:

(wherein the ring A" represents a piperidine ring which may be further substituted)].

The substituent which the divalent group represented by A may optionally have (the substituent which a piperazine ring represented by the ring A' may optionally have, and the substituent which a piperidine ring represented by the ring A" may optionally have) includes the same groups as those exemplified for the substituent in the term of the above-mentioned "heterocyclic group which may be optionally substituted" represented by $R^1$, and the like. 1 to 5 (preferably 1 to 3) of these optional substituents may be at substitutable position(s). Among these, preferable ones may be a $C_{1-6}$ alkyl group (which may be optionally substituted with a $C_{1-6}$ alkylsulfinyl group, a $C_{1-6}$ alkylsulfonyl group, a hydroxy group or carboxyl which may be optionally esterified or amidated), a hydroxy group, a carboxyl group which may be optionally esterified or amidated, and an oxo group, and the like.

In the above-mentioned formula, $Y^2$ represents —C(O)—, —S(O)—, —S(O)$_2$— or —C((=NR$^7$)— (wherein $R^7$ represents a hydrogen atom, a hydroxy group which may be optionally substituted, a lower alkoxycarbonyl group or an acyl group).

Examples of the substituent in the term of "hydroxy group which may be optionally substituted" represented by $R^7$ include (1) lower alkyl (for example, $C_{1-6}$ alkyl such as methyl, ethyl, propyl, isopropyl, butyl, isobutyl, tert-butyl, pentyl, and hexyl and the like) which may be optionally substituted with a substituent selected from a halogen atom (for example, fluorine, chlorine, bromine and iodine, and the like) and $C_{1-6}$ alkoxy which may be optionally halogenated (for example, methoxy, ethoxy, trifluoromethoxy, 2,2,2-trifluoroethoxy, trichloromethoxy, 2,2,2-trichloroethoxy and the like), (2) acyl such as $C_{1-6}$ alkanoyl (for example, formyl, acetyl, propionyl, valeroyl, pivaloyl and the like), benzoyl, $C_{1-6}$ alkylsulfonyl (for example, methanesulfonyl and the like), benzenesulfonyl, and the like (3) $C_{1-6}$ alkoxycarbonyl which may be optionally halogenated (for example, methoxycarbonyl, ethoxycarbonyl, trifluoromethoxycarbonyl, 2,2,2-trifluoroethoxycarbonyl, trichloromethoxycarbonyl, 2,2,2-trichloroethoxycarbonyl and the like), $C_{1-6}$ alkoxycarbonyl which may be optionally substituted with phenyl (for example, benzyloxycarbonyl and the like), and the like.

Examples of the "lower alkoxycarbonyl group" represented by $R^7$ include $C_{1-6}$ alkoxycarbonyl such as methoxycarbonyl, ethoxycarbonyl, and the like; and the like.

Examples of the "acyl" represented by $R^7$ include the same groups as acyl exemplified for the substituent in the term of the "cyclic hydrocarbon group which may be optionally substituted" represented by $R^1$ (preferably, $C_{2-6}$ alkanoyl such as formyl, acetyl, propionyl, valeroyl, pivaloyl and the like) and the like.

$R^7$ is preferably a hydrogen atom.

$Y^2$ is preferably —C(O)— or —C(=NH)—.

In the above-mentioned formula, $X^3$ represents a $C_{1-4}$ alkylene which may be optionally substituted or a $C_{2-4}$ alkenylene which may be optionally substituted.

Examples of the "$C_{1-4}$ alkylene" in the term of "$C_{1-4}$ alkylene which may be optionally substituted" represented by $X^3$ include methylene, ethylene, trimethylene, tetramethylene, and the like and among these, $C_{2-4}$ alkylene such as ethylene, trimethylene, tetramethylene and the like is preferable.

Examples of the "$C_{2-4}$ alkenylene" in the term of "$C_{2-4}$ alkenylene which may be optionally substituted" represented by $X^3$ include vinylene, propylene, 1- or 2-butenylene, butadienylene and the like.

Examples of the "substituent" in the terms of "$C_{1-4}$ alkylene which may be optionally substituted" and the "$C_{2-4}$ alkenylene which may be optionally substituted" represented by $X^3$ include the same groups as those exemplified for the substituent in the term of for the above-mentioned "cyclic hydrocarbon group which may be optionally substituted" represented by $R^1$, and the like. Among these, preferable examples may be lower alkyl (for example, $C_{1-6}$ alkyl such as methyl, ethyl, propyl and the like), lower alkenyl (for example, $C_{2-6}$ alkenyl such as vinyl, allyl and the like), lower alkynyl (for example, $C_{2-6}$ alkynyl such as ethynyl and propargyl, and the like), amino which may be optionally substituted, a hydroxy group which may be optionally substituted, carboxy, a lower alkoxycarbonyl group (for example, $C_{1-6}$ alkoxycarbonyl such as methoxycarbonyl and ethoxycarbonyl, and the like), a carbamoyl group which may be optionally substituted (for example, a carbamoyl group which may be optionally substituted with $C_{1-6}$ alkyl or acyl (for example, formyl, $C_{2-6}$ alkanoyl, benzoyl, $C_{1-6}$ alkoxycarbonyl which may be optionally halogenated, $C_{1-6}$ alkylsulfonyl which may be optionally halogenated, benzenesulfonyl, p-toluenesulfonyl and the like), or an oxo group, and the like. 1 to 3 of these substituents may be at optional substitutable position(s).

When $X^3$ is $C_{2-4}$ alkenylene substituted with two lower alkyl groups, said two lower alkyl groups may be bound to each other to form aryl group such as $C_{6-14}$ aryl (e.g. phenyl, naphthyl, etc.) together with adjacent carbon atoms of $X^3$ to which said two alkyl groups attach respectively.

In the above-mentioned formula, $Z^3$ represents —N($R^4$)—, —O— or a bond (wherein $R^4$ represents a hydrogen atom, a hydrocarbon group which may be optionally substituted, or an acyl group).

Examples of the "hydrocarbon group" in the term of "hydrocarbon group which may be optionally substituted" represented by $R^4$ include alkyl, alkenyl, alkynyl, aryl, cycloalkyl, cycloalkenyl, aralkyl and the like.

The alkyl, alkenyl, alkynyl, aryl, cycloalkyl and cycloalkenyl include respectively the same groups as those exemplified for alkyl, alkenyl, alkynyl, aryl, cycloalkyl and cycloalkenyl in the terms of "alkyl which may be optionally substituted", "alkenyl which may be optionally substituted", "alkynyl which may be optionally substituted", "aryl which may be optionally substituted", "cycloalkyl which may be optionally substituted" and "cycloalkenyl which may be optionally substituted" as the substituent in the term of above-mentioned "cyclic hydrocarbon group which may be optionally substituted" represented by $R^1$, and the like.

Examples of the aralkyl include phenyl-$C_{1-6}$ alkyl groups such as benzyl, phenethyl, 3-phenylpropyl and 4-phenylbutyl, and $C_{7-16}$ aralkyl groups such as naphthyl-$C_{1-6}$ alkyl groups, for example, (1-naphthyl)methyl, 2-(1-naphthyl)ethyl and 2-(2-naphthyl)ethyl, and the like.

Examples of the "acyl group" represented by $R^4$ include the same groups as those exemplified for the substituent in the term of "cyclic hydrocarbon group which may be optionally substituted" represented by $R^1$, and the like.

Examples of the "substituent" in the term of "hydrocarbon group which may be optionally substituted" represented by $R^4$ include the same groups as those exemplified for the substituent in the term of the above-mentioned "cyclic hydrocarbon group which may be optionally substituted" represented by $R^1$, and the like. Among these, preferable examples may be lower alkyl (for example, $C_{1-6}$ alkyl such as methyl, ethyl, propyl and the like), lower alkenyl (for example, $C_{2-6}$ alkenyl such as vinyl, allyl and the like), lower alkynyl (for example, $C_{2-6}$ alkynyl such as ethynyl and propargyl, and the like), amino which may be optionally substituted, a hydroxy group which may be optionally substituted, carboxy, a lower alkoxycarbonyl group (for example, $C_{1-6}$ alkoxycarbonyl such as methoxycarbonyl and ethoxycarbonyl, and the like), a carbamoyl group which may be optionally substituted (for example, a carbamoyl group which may be optionally substituted with $C_{1-6}$ alkyl or acyl (for example, formyl, $C_{2-6}$ alkanoyl, benzoyl, $C_{1-6}$ alkoxycarbonyl which may be optionally halogenated, $C_{1-6}$ alkylsulfonyl which may be optionally halogenated, benzenesulfonyl, p-toluenesulfonyl and the like), or an oxo group, and the like. 1 to 3 of these substituents may be at optional substitutable position(s).

$Z^3$ is preferably a bond.

In the above-mentioned formula, when ══════ is a single bond, $Z^1$ represents —C($R^2$)($R^{2'}$)—, —N($R^2$)— or —O—, and $Z^2$ represents —C($R^3$)($R^{3'}$)—, —N($R^3$)—, —O— or a bond (provided that when $Z^1$ is —O—, $Z^2$ is not —O—), and when ══════ is a double bond, $Z^1$ represents —C($R^2$)= or a nitrogen atom, and $Z^2$ represents =C($R^3$)— or a nitrogen atom.

Herein, each of $R^2$, $R^{2'}$, $R^3$ and $R^{3'}$ represents a hydrogen atom, a hydrocarbon group which may be optionally substituted or a heterocyclic group which may be optionally substituted, or each pair of $R^2$ and $R^3$, and $R^{2'}$ and $R^{3'}$ may be bound to each other to form a ring which may be optionally substituted.

Examples of the "hydrocarbon group" in the term of "hydrocarbon group which may be optionally substituted" represented by $R^2$, $R^{2'}$, $R^3$ and $R^{3'}$ include the same groups as those exemplified for the "hydrocarbon group" in the term of "hydrocarbon group which may be optionally substituted" represented by $R^4$, and the like.

Examples of the "substituent" in the term of "hydrocarbon group which may be optionally substituted" represented by $R^2$, $R^{2'}$, $R^3$ and $R^{3'}$ include the same number of the same groups as those exemplified for the substituent in the term of "hydrocarbon group which may be optionally substituted" represented by $R^4$, and the like.

Examples of the "heterocyclic group" in the term of "heterocyclic group which may be optionally substituted" represented by $R^2$, $R^{2'}$, $R^3$ and $R^{3'}$ include the same groups as those exemplified for the "heterocyclic group" in the term of "heterocyclic group which may be optionally substituted" represented by $R^1$, and the like.

Examples of the substituent in the term of "heterocyclic group which may be optionally substituted" represented by $R^2$, $R^{2'}$, $R^3$ and $R^{3'}$ include the same number of the same groups as those exemplified for the substituent in the term of "heterocyclic group which may be optionally substituted" represented by $R^4$, and the like.

Preferable examples of $R^2$, $R^{2'}$, $R^3$ and $R^{3'}$ may include respectively a hydrogen atom, $C_{1-6}$ alkyl (the $C_{1-6}$ alkyl group may be optionally substituted with a halogen atom, hydroxy, carbamoyl, N—$C_{1-6}$ alkylcarbamoyl, N,N-di-$C_{1-6}$ alkylcarbamoyl, carboxyl, $C_{1-4}$ alkoxycarbonyl, $C_{1-6}$ alkoxy, amino, mono- or di-$C_{1-6}$ alkylamino, $C_{1-6}$ alkanoylamino and the like) and the like.

The "ring" in the term of "ring which may be optionally substituted" which each pair of $R^2$ and $R^3$, and $R^{2'}$ and $R^{3'}$ may be bound to each other to form may be either of a homocyclic ring or a heterocyclic ring.

Examples of the "homocyclic ring or heterocyclic ring" include 1) an aromatic heterocyclic ring or non-aromatic heterocyclic ring which contains preferably 1 to 3 of one or two kinds of hetero atom(s) selected from a nitrogen atom, a sulfur atom and an oxygen atom in addition to carbon atoms, and 2) a cyclic hydrocarbon (homocyclic ring) consisting of carbon atoms.

Examples of the "aromatic heterocyclic ring" include 5- to 6-membered aromatic heterocyclic rings which contain 1 to 3 of hetero atom(s) selected from a nitrogen atom, a sulfur atom and an oxygen atom in addition to carbon atoms (for example, pyridine, pyrazine, pyrimidine, pyridazine, pyrrole, imidazole, pyrazole, triazole, thiophene, furan, thiazole, isothiazole, oxazole and isoxazole rings), and the like.

Examples of the "non-aromatic heterocyclic ring" include 5- to 9-membered (preferably 5- to 6-membered) non-aromatic heterocyclic rings which contain 1 to 3 of hetero atom(s) selected from a nitrogen atom, a sulfur atom and an oxygen atom in addition to carbon atoms (for example, tetrahydropyridine, dihydropyridine, tetrahydropyrazine, tetrahydropyrimidine, tetrahydropyridazine, dihydropyran, dihydropyrrole, dihydrothiophene, dihydrofuran, piperidine, piperazine, hexahydropyrimidine, hexahydropyridazine, tetrahydropyran, morpholine, pyrrolidine, pyrazoline, imidazoline, thiazoline, isothiazoline, oxazoline, isooxazoline, pyrazolidine, tetrahydrothiophene, tetrahydrofuran, tetrahydrothiazole, tetrahydroisothiazole, tetrahydrooxazole and tetrahydroisooxazole rings and the like), and the like.

Examples of the "cyclic hydrocarbon group (homocyclic ring)" include 3- to 10-membered (preferably 5- to 9-membered and more preferably 5- to 6-membered) cyclic hydrocarbons, and include benzene, $C_{3-10}$ cycloalkene (for example, cyclobutene, cyclopentene, cyclohexene, cycloheptene, cyclooctene and the like), $C_{3-10}$ cycloalkane (for example, cyclobutane, cyclopentane, cyclohexane, cycloheptane, cyclooctane and the like), and the like. The cycloalkene is preferably $C_{5-6}$ cycloalkene (for example, cyclopentene, cyclohexene and the like), and the cycloalkane is preferably $C_{5-6}$ cycloalkane (for example, cyclopentane, cyclohexane and the like).

Examples of the substituent in the term of "ring which may be optionally substituted" include the same groups as those exemplified for the substituent which the "hydrocarbon group" in the term of "hydrocarbon group which may be optionally substituted" represented by $R^4$ may optionally have, and the like. 1 to 5 (preferably 1 to 3) of these optional substituents may be at substitutable position(s).

When ------ is a double bond, $Z^1$ is —$C(R^2)$= and $Z^2$ is =$C(R^3)$—, the example of the "ring" which $R^2$ and $R^3$ are bound to each other to form is preferably a benzene ring and the like.

In the above-mentioned formula, the group:

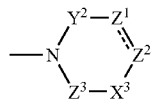

is preferably represented by the formula:

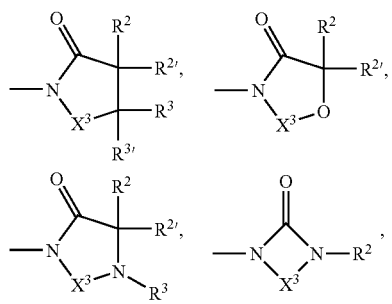

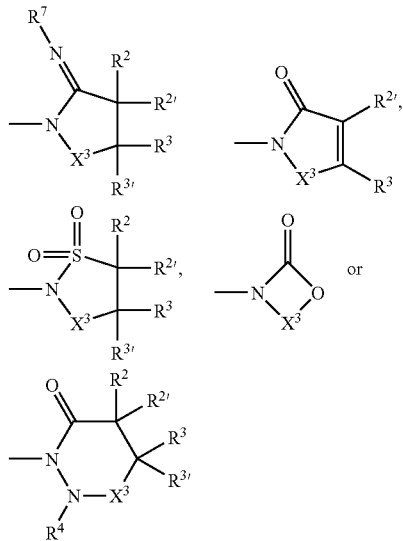

wherein each symbol is as defined above, and the like and among these, the groups of the formula:

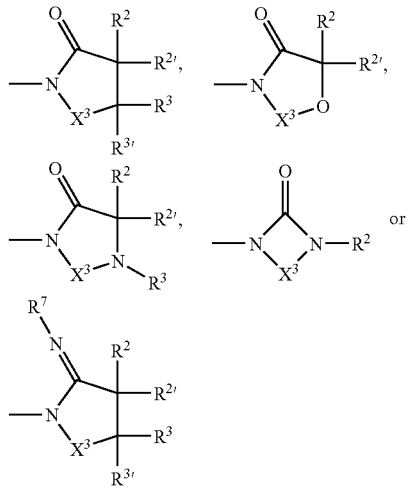

wherein each symbol is as defined above (more preferably, $R^2$ is a hydrogen atom and $X^3$ is $C_{2-4}$ alkylene) are preferable. In the above-mentioned formula, a represents 0, 1 or 2 (preferably 2).

As the compound represented by the formula (I) in the present invention, in particular, 4-(1-{(2S)-3-[(6-chloronaphthalen-2-yl)sulfonyl]-2-hydroxypropanoyl}piperidin-4-yl)morpholin-3-one, 1-(4-{(2S)-3-[(6-chloronaphthalen-2-yl)sulfonyl]-2-hydroxypropanoyl}piperazin-1-yl)piperidin-2-one, 1-(1-{(2S)-3-[(6-chloronaphthalen-2-yl)sulfonyl]-2-hydroxypropanoyl}piperidin-4-yl)tetrahydropyrimidin-2(1H)-one, 1-(4-{(2S)-3-[(6-chloronaphthalen-2-yl)sulfonyl]-2-hydroxypropanoyl}piperazin-1-yl)tetrahydropyrimidin-2(1H)-one, 1-(1-{3-[(6-chloronaphthalen-2-yl)sulfonyl]propanoyl}piperazin-4-yl)tetrahydropyrimidin-2(1H)-one, (2S)-3-[(6-chloronaphthalen-2-yl)sulfonyl]-1-(2-imino-1,4'- bipiperidin-1'-yl)-1-oxopropan-2-ol, 1'-{(2S)-3-[(6-Chloronaphthalen-2-yl)sulfonyl]-2-hydroxypropanoyl}-1,4'-bipiperidin-2-one,
2-(1-{(2S)-3-[(6-Chloronaphthalen-2-yl)sulfonyl]-2-hydroxypropanoyl}piperidin-4-yl)isoindolin-1-one and the like are preferably used.

A salt of a compound represented by the formula (I) (hereinafter, abbreviated as Compound (I) in some cases) includes pharmaceutically acceptable salts, for example, acid addition salts with acids such as trifluoroacetic acid, acetic acid, lactic acid, succinic acid, maleic acid, tartaric acid, citric acid, gluconic acid, ascorbic acid, benzoic acid, methanesulfonic acid, p-toluenesulfonic acid, cinnamic acid, fumaric acid, phosphonic acid, hydrochloric acid, nitric acid, hydrobromic acid, hydriodic acid, sulfamic acid, sulfuric acid and the like, metal salts such as sodium, potassium, magnesium, calcium and the like, and organic salts such as trimethylamine, triethylamine, pyridine, picoline, N-methylpyrrolidine, N-methylpiperidine, N-methylmorpholine and the like.

A prodrug of Compound (I) refers to a compound which is converted into Compound (I) by a reaction due to an enzyme or gastric acid under the physiological condition in a living body, that is, a compound which is changed into Compound (I) by enzymatic oxidation, reduction, hydrolysis or the like, or a compound which is changed into Compound (I) by hydrolysis with gastric acid. A prodrug of Compound (I) includes a compound obtained by acylating, alkylating or phosphorylating the amino group of Compound (I) (e.g. a compound obtained by eicosanoylating, alanylating, pentylaminocarbonylating, (5-methyl-2-oxo-1,3-dioxolen-4-yl)methoxycarbonylating, tetrahydrofuranylating, pyrrolidylmethylating, pivaloyloxymethylating or tert-butylating the amino group of Compound (I)), a compound obtained by acylating, alkylating, phosphorylating or borating the hydroxyl group of Compound (I) (e.g. a compound obtained by acetylating, palmitoylating, propanoylating, pivaloylating, succinylating, fumarylating, alanylating or dimethylaminomethylcarbonylating the hydroxyl group of Compound (I)) and a compound obtained by esterifying or amidating the carboxyl group of Compound (I) (e.g. a compound obtained by ethylesterifying, phenylesterifying, carboxymethylesterifying, dimethylaminomethylesterifying, pivaloyloxymethylesterifying, ethoxycarbonyloxyethylesterifying, phthalidylesterifying, (5-methyl-2-oxo-1,3-dioxolen-4-yl)methylesterifying, cyclohexyloxycarbonylethylesterifying or methylamidating the carboxyl group of Compound (I)). These compounds can be prepared from Compound (I) by a known method per se.

A prodrug of Compound (I) may be also a compound which is changed into Compound (I) under the physiological condition as described in "Development of Medicaments", vol. 7, Molecular Design, p. 163-198 published by HIROKAWASHOTEN in 1990.

Compound (I) may be labeled with an isotope (e.g. $^3$H, $^{14}$C, $^{35}$S, $^{125}$I) or the like.

The compound (I) or its salt can be prepared, for example, by methods as shown hereinafter. Each compound in the following reaction scheme may form a salt so far as it does not inhibit the reaction, and the salt includes those similar to the salt of the compound (I).

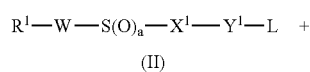

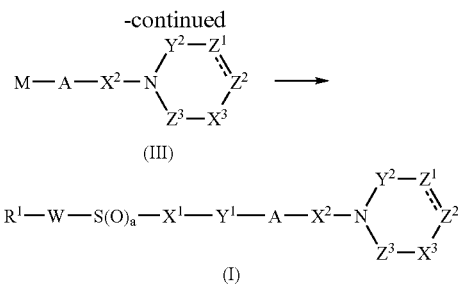

That is, the compound (I) can be prepared by reacting the compound (II):

$$R^1\text{---}W\text{---}S(O)_a\text{---}X^1\text{---}Y^1\text{-L} \qquad (II)$$

wherein L represents a leaving group [for example, a group which forms free acid, its salt (inorganic salt, organic salt and the like) or its reactive derivative (for example, acid halide, ester, acid azide, acid anhydride, mixed acid anhydride, active amide, active ester, active thioester and the like) such as a halogen atom (for example, fluorine, chlorine, bromine, iodine, and the like), $C_{1-6}$ alkylsulfonyloxy group which may be optionally substituted with 1 to 3 of halogen atoms (for example, methanesulfonyloxy, ethanesulfonyloxy, trifluoromethanesulfonyloxy and the like), arylsulfonyloxy which may optionally have substituent (for example, benzenesulfonyloxy, p-toluenesulfonyloxy, p-bromobenzenesulfonyloxy and the like), or a hydroxy group] and the other symbols are as defined above (in particular, the compound (II) in which L is a hydroxy group is referred to as a free acid (II')) with the compound (III) represented by the formula (III):

wherein M represents a hydrogen atom, an alkali metal (for example, lithium, sodium, potassium, cesium and the like), an alkali earth metal (for example, magnesium, calcium and the like) or a leaving group (for example, trimethylsilyl group) and the other symbols are as defined above.

Further, this method is also carried out by reacting the compound (III) or its salt with a free acid (II') or its salt (inorganic salt, organic salt, and the like) or its reactive derivative (for example, acid halide, ester, acid azide, acid anhydride, mixed acid anhydride, active amide, active ester, active thioester, and the like). Examples of the salt of the compound (III) include acid addition salts with acids which are described as those forming acid addition salts of the compound (I).

As the inorganic salt used for compound (II), an alkali metal salt (for example, lithium salt, sodium salt, potassium salt, cesium salt, and the like), an alkaline earth metal salt (for example, magnesium salt, calcium salt, and the like), and the like are used, and as the organic salt, for example, trimethylamine salt, triethylamine salt, tert-butyldimethylamine salt, dibenzylmethylamine salt, benzyldimethylamine salt, N,N-dimethylaniline salt, pyridine salt, quinoline salt, and the like are used. Further, examples of the acid halide include acid chloride, acid bromide, and the like; examples of the ester include eaters with lower alkyls such as methyl and ethyl; the mixed acid anhydrides include a mono-$C_{1-4}$ alkyl carbonic acid mixed acid anhydride (for example, the mixed acid anhydride of the free acid (II') with mono-methylcarbonic acid, mono-ethylcarbonic acid, mono-isoproylcarbonic acid, mono-isobutylcarbonic acid, mono-tert-butylcarbonic acid, mono-benzylcarbonic acid, mono-(p-nitrobenzyl)carbonic acid, mono-allylcarbonic acid, and the like), a $C_{1-6}$ aliphatic carboxylic acid mixed acid anhydride (for example, the mixed acid anhydride of the free acid (II') with acetic acid, cyanoacetic acid, propionic acid, butyric acid, isobutyric acid, valeric acid, isovaleric acid, pivalic acid, trifluoroacetic acid, trichloroacetic acid, acetoacetic acid, and the like), a $C_{7-11}$ aromatic carboxylic acid mixed acid anhydride (for example, the mixed acid anhydride of the free acid (II') with benzoic acid, p-toluic acid, p-chlorobenzoic acid, and the like), an organic sulfonic acid mixed acid anhydride (the mixed acid anhydride with methane sulfonic acid, ethane sulfonic acid, benzenesulfonic acid, p-toluenesulfonic acid, and the like) and the like; and the active amide includes amide with a nitrogen-containing heterocyclic compound (for example, the acid amide of the free acid (II') with pyrazole, imidazole, benzotriazole, and the like, and these nitrogen-containing heterocyclic compounds may be optionally substituted with $C_{1-6}$ alkyl (for example, methyl, ethyl, propyl, isopropyl, butyl, isobutyl, sec-butyl, tert-butyl, and the like), $C_{1-6}$ alkoxy (for example, methoxy, ethoxy, propoxy, isopropoxy, butoxy, tert-butoxy, and the like), a halogen atom (for example, fluorine, chlorine, bromine, and the like), oxo, thioxo, $C_{1-6}$ alkylthio (for example, methylthio, ethylthio, propylthio, butylthio, and the like), and the like) and the like.

Examples of the active ester include p-nitrophenyl ester, 2,4-dinitrophenyl ester, cyanomethyl ester, pentachlorophenyl ester, N-hydroxysuccinimide ester, N-hydroxyphthalimide ester, 1-hydroxybenzotriazole ester, 6-chloro-1-hydroxybenzotriazole ester, 1-hydroxy-1H-2-pyridone ester and the like in addition to an organic phosphate (for example, diethoxy phosphate, diphenoxy phosphate and the like). Examples of the active thio ester include esters with an aromatic heterocyclic thiol compound (for example, 2-pyridylthiol ester, 2-benzothiazolylthiol ester) (these heterocyclic rings may be optionally substituted with $C_{1-6}$ alkyl (for example, methyl, ethyl, propyl, isopropyl, butyl, isobutyl, sec-butyl, tert-butyl, and the like), $C_{1-6}$ alkoxy (for example, methoxy, ethoxy, propoxy, isopropoxy, butoxy, tert-butoxy, and the like), a halogen atom (for example, fluorine, chlorine, bromine, and the like), $C_{1-6}$ alkylthio (for example, methylthio, ethylthio, propylthio, butylthio, and the like), and the like).

This reaction is usually carried out in a solvent, and if necessary, carried out in the presence of a base or a condensing agent (for example, carbodiimides (DCC, WSC, DIC and the like), phosphoric acid derivatives (for example, diethyl cyano phosphate, DPPA, BOP-Cl, and the like), chlorinated 4-(4,6-dimethoxy-1,3,5-triazin-2-yl)-4-methylmorpholinium (DMTMM: Kunishima et al, Tetrahedron, 1999, Vol. 55, page 13159), and the like.

As the solvent, a solvent which does not hinder the reaction is appropriately selected, and examples thereof include alcohols (for example, methanol, ethanol, propanol, isopropanol, butanol, tert-butanol, and the like), ethers (for example, dioxane, tetrahydrofuran, diethyl ether, tert-butyl methyl ether, diisopropyl ether, ethylene glycol-dimethyl ether, and the like), esters (for example, ethyl formate, ethyl acetate, n-butyl acetate, and the like), carboxylic acids (for example, formic acid, acetic acid, propionic acid, and the like), halogenated hydrocarbons (for example, dichloromethane, chloroform, carbon tetrachloride, trichloroethylene, 1,2-dichloroethane, chlorobenzene, and the like), hydrocarbons (for example, n-hexane, benzene, toluene, and the like), amides (for example, formamide, N,N-dimethylformamide, N,N-dimethyl acetamide, and the like), ketones (for example, acetone, methyl ethyl ketone, methyl isobutyl ketone, and the like), nitriles (for example, acetonitrile, propionitrile, and the like), dimethyl sulfoxide, sulfolane, hexamethylphosphoramide, water, and the like. They are used alone or as a mixed solvent thereof.

Examples of the base include inorganic bases such as lithium hydroxide, potassium hydroxide, sodium hydroxide, calcium hydroxide, sodium carbonate, potassium carbonate, sodium bicarbonate and potassium. bicarbonate, the alkali metal salts of a $C_{1-6}$ lower fatty acid such as sodium formate, sodium acetate and potassium acetate, tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine and N-methylmorpholine.

In this reaction, the compound (III) is used in an amount of 0.5 to 5 equivalents, preferably 0.8 to 2 equivalents relative to the compound (II).

The reaction temperature is −50 to 150° C. and preferably −20 to 100° C.

The reaction time varies depending on the kind of the compound (II) or (III), the kind of the solvent and the base, the reaction temperature and the like, but usually it is from about 1 minute to about 100 hours, preferably from about 15 minutes to 48 hours.

The starting materials and intermediates used in each of the above-mentioned reactions can be prepared by using or modifying known methods, for example, the methods described in Examples hereinafter or chemical equivalents thereof, or according to the methods of the present invention.

The compound (I) thus obtained can be isolated and purified from a reaction mixture by known procedures, for example, extraction, concentration, neutralization, filtration, recrystallization, column chromatography, thin layer chromatography, and the like.

The salt of the compound (I) can be prepared according to known methods per se, for example, adding an inorganic acid or an organic acid to the compound (I).

When optical isomers of the compound (I) are present, either of these individual optical isomers and a mixture thereof are included in the scope of the present invention, and if necessary, these optical isomers can be optically resolved according to known methods per se, or can also be prepared individually.

Further, the compound (I) or its salt may be a hydrate, and both of the hydrate and non-hydrate are included in the scope of the present invention.

The compound (I) or its salt of the present invention is safe with low toxicity (for example, it is superior as medicaments from the viewpoints such as acute toxicity, chronic toxicity, genetic toxicity, reproductive toxicity, cardiac toxicity, drug interactions, carcinogenicity, and the like), inhibits FXa, and has anticoagulation effect; therefore it is useful for preventing (including secondary preventing) and treating various arterial and venous thrombosis of human beings and animals, in particular mammals (for example, human being, monkey, cat, pig, horse, cattle, mouse, rat, guinea pig, dog, rabbit, and the like), for example, myocardial infarction, cerebral infarction, deep vein thrombosis, pulmonary thromboembolism or atherosclerotic obliterans, economy-class syndrome, thromboembolism during and post operation, cancer and the following disorders.

Among these, it is preferably used for preventing and treating ischemic cerebral infarction (e.g. thromboembolic stroke, for example, thromboembolic stroke due to atrial fibrillation, and the like; and ischemic cerebral infarction caused by progression of atherosclerosis or activation of blood coagulation system), deep vein thrombosis or pulmonary thromboembolism, for example, deep vein thrombosis or pulmonary thromboembolism after a joint operation including total hip arthroplasty (THA) or total knee arthroplasty (TKA); or the secondary prevention of myocardial infarction.

Brain:

Prevention or treatment of cerebral infarction, ischemic cerebrovascular disorder, thromboembolic stroke caused by atrial fibrillation, heart failure, valvular disease and heart valve replacement, acute ischemic cerebral apoplexy, acute stage cerebral thrombosis, cerebrovascular contraction after subarachnoid hemorrhage, Alzheimer's disease, transient ischemic attack (TIA), mixed dementia, cerebrovascular dementia, asymptomatic/multiple cerebral infarction, lacunar infarction and the like, prognosis improvement or secondary onset prevention of cerebral infarction, prevention or treatment of thrombus after an extracranial and intracranial arterial bypass operation, combination use or supplemental use with a thrombolytic agent against cerebral infarction (among them, ischemic cerebrovascular disorder), combination therapy with an anti-platelet drug such as aspirin in preventing onset of cerebral infarction.

Heart:

Prevention or treatment of acute coronary disease such as acute myocardial infarction, myocardial infarction, ischemic coronary disease, unstable angina, myocardiopathy, acute heart failure, congestive chronic heart failure, valvular disease and the like, prognosis improvement or secondary onset prevention of acute coronary disease such as angina, prevention or treatment of thrombus formation after artificial valve or artificial heart replacement, prevention or treatment of vascular reocclusion and restenosis after coronary intervention such as stent indwelling or PTCA (percutaneous transluminal coronary angioplasty) or atherectomy, prevention or treatment of vascular reocclusion and restenosis after coronary bypass operation, combination use or supplemental use with a thrombolytic agent against acute coronary disease, combination therapy with an anti-platelet drug such as aspirin in preventing onset of myocardial infarction.

Periphery:

Prevention or treatment of deep vein thrombosis, chronic arterial obliterans, atherosclerotic obliterans, peripheral circulation failure such as Buerger's disease, peripheral circulation failure after frostbite, aneurysm, varix, adult respiratory distress syndrome, acute renal failure, chronic renal disease (e.g. diabetic nephropathy, chronic glumerular nephritis, IgA nephropathy etc.), diabetic circulation disorder, pain, nerve disorder, diabetic complication such as diabetic retinopathy and the like, prognosis improvement or secondary onset prevention of deep vein thrombosis, prevention or treatment of deep vein thrombosis or pulmonary thromboembolism after a joint operation including total hip arthroplasty (THA) or total knee arthroplasty (TKA), prevention or treatment of deep vein thrombosis or pulmonary thromboembolism after an orthopedic, plastic surgical or general surgical operation including a spine operation, prevention or treatment of thrombus after a peripheral vascular bypass operation or artificial vessel or vena cava filter indwelling, prevention or treatment of reocclusion and restenosis after stent indwelling or PTA (percutaneous transluminal angioplasty) or peripheral vascular intervention such as atherectomy, prevention or treatment of deep vein thrombosis or pulmonary thromboembolism accompanied with acute internal disease, combination use or supplemental therapy with a thrombolytic agent against deep vein thrombosis and pulmonary thromboembolism, combination therapy with an anti-platelet drug such as aspirin in therapy of peripheral circulation failure such as arteriosclerotic obliterans.

Others:

Prevention or treatment of pulmonary embolism, acute pulmonary embolism, economy class syndrome, thrombocytopenia or activation of blood coagulation system or complement activation caused by dialysis, thrombocytopenia on a major operation, thrombocytopenic purpura, disseminated intravascular coagulation syndrome (DIC) developed in a patient suffering from progression of arteriosclerosis or cancer metastasis or systemic inflammatory reaction syndrome (SIRS) or pancreatitis or cancer or leukemia or a major operation or sepsis or the like, various organ disorders such as liver function disorder caused by oligemia or ischemia or retention of blood, various organ failures caused by progression of shock or DIC (e.g. lung failure, liver failure, kidney failure, heart failure etc.), systemic lupus erythematosus, diffuse collagen disease, hyperthyroidism, puerperal palsy and the like, inhibition of rejective response on transplantation, organ protection or function improvement on transplantation, prevention of perfusion blood coagulation during blood extracorporeal circulation, substitute therapeutic use against development of thrombocytopenia caused by heparin administration, promotion of bedsore or wound healing, inhibition of activation of blood excessive coagulation reaction on various hormone supplement therapy, substitute therapeutic use for a patient resistant or contraindicative to a coumarin drug including warfarin, inhibition of activation of excessive coagulation reaction on administration of a blood preparation or a blood coagulation factor-containing preparation, and the like.

Compound (I) of the present invention or a salt thereof can be orally or parenterally administered as it is or as a composition comprising a pharmacologically acceptable carrier.

An oral dosage form of a pharmaceutical composition containing Compound (I) of the present invention or a salt thereof includes a tablet (including a sugar-coated tablet, a film coating tablet), a pill, a granule, powder, a capsule (including a soft capsule, a microcapsule), syrup, emulsion and suspension. A parenteral dosage form of a pharmaceutical composition containing Compound (I) of the present invention or a salt thereof includes an injection, an infusion, a drip and a suppository. It is also advantageous that Compound (I) of the present invention or a salt thereof in combination with an appropriate base (e.g. a polymer of butyric acid, a polymer of glycolic acid, a copolymer of butyric acid-glycolic acid, a mixture of a polymer of butyric acid and a polymer of glycolic acid, polyglycerol fatty acid ester etc.) is formulated into a sustained release form.

The content of Compound (I) or a salt thereof in a pharmaceutical composition of the present invention varies depending on the form of a composition, and is usually 2 to 85% by weight, preferably 5 to 70% by weight of the total composition.

Compound (I) or a salt thereof may be formulated into the aforementioned dosage forms by known methods used generally in the art (e.g. the methods as disclosed in Japanese Pharmacopoeia, etc.). When Compound (I) or a salt thereof is formulated into the aforementioned dosage forms, if necessary, appropriate amounts of an excipient, a binder, a disintegrant, a lubricant, a sweetener, a surfactant, a suspending agent, an emulsifying agent and the like which are conventionally used in pharmaceutical field may be added.

For example, when Compound (I) or a salt thereof is formulated into a tablet, an excipient, a binder, a disintegrant, a lubricant and the like are added. When Compound (I) or a salt thereof is formulated into a pill or a granule, an excipient, a binder, a disintegrant and the like are added. When Compound (I) or a salt thereof is formulated into powder or a capsule, an excipient and the like are added. When Compound (I) or a salt thereof is formulated into syrup, a sweetener and the like are added. When Compound (I) or a salt thereof is formulated into an emulsion or a suspension, a suspending agent, a surfactant, an emulsifying agent and the like are added.

An Excipient includes lactose, white sugar, glucose, starch, sucrose, microcrystalline cellulose, licorice powder, mannitol, sodium hydrogencarbonate, calcium phosphate, calcium sulfate and the like.

A binder includes 5 to 10% by weight starch paste, a 10 to 20% by weight gum arabic solution or gelatin solution, a 1 to 5% by weight tragacanth solution, a carboxymethylcellulose solution, a sodium alginate solution, glycerin and the like.

A disintegrant includes starch, calcium carbonate and the like.

A lubricant includes magnesium stearate, stearic acid, calcium stearate, purified talc and the like.

A sweetener includes glucose, fructose, invert sugar, sorbitol, xylitol, glycerin, simple syrup and the like.

A surfactant includes sodium lauryl sulfate, Polysorbate 80, sorbitan monofatty acid ester, polyoxyl stearate 40 and the like.

A suspending agent includes gum arabic, sodium alginate, sodium carboxymethylcellulose, methylcellulose, bentonite and the like.

An emulsifying agent includes gum arabic, tragacanth, gelatin, Polysorbate 80 and the like.

Further, when Compound (I) or a salt thereof is formulated into the aforementioned dosage forms, if desired, appropriate amounts of a coloring agent, a preservative, a flavor, a corrigent, a stabilizer, a thickener and the like which are conventionally used in pharmaceutical field may be added.

A pharmaceutical composition of the present invention containing Compound (I) or a salt thereof is safe and low toxic and can be used safely. A daily dose of a pharmaceutical composition of the present invention varies depending on the condition and body weight of a patient, the kind of a compound, an administration route and the like. For example, when it is administered orally to an adult patient (body weight about 60 kg) with thrombosis, the daily dose is about 1 to 1000 mg, preferably about 3 to 500 mg, more preferably about 10 to 350 mg of an active ingredient (Compound (I) or a salt thereof), which may be administered once or in two or three divided portions.

When Compound (I) or a salt thereof of the present invention is administered parenterally, it may be usually administered as a form of a solution (e.g. an injection). A dose per time varies depending on a subject to be administered, an organ to be targeted, symptom, an administration method and the like. For example, conveniently, about 0.01 mg to about 100 mg, preferably about 0.01 to about 50 mg, more preferably about 0.01 to about 20 mg per kg body weight of Compound (I) or a salt thereof is administered intravenously in a dosage form of an injection. An injection includes, in addition to intravenous injection, subcutaneous injection, intradermal injection, intramuscular injection, drip injection and the like. A long-acting preparation includes an iontophoresis transdermal agent. Such an injection is prepared by a known method per se, that is, by dissolving, suspending or emulsifying Compound (I) or a salt thereof of the present invention in a sterile aqueous or oily liquid. An aqueous liquid for injection includes physiological saline, and an isotonic solution containing glucose and other supplemental agent (e.g. D-sorbitol, D-mannitol, sodium chloride etc.) and may be used in combination with a suitable solubilizer, for example, alcohol (e.g. ethanol), polyalcohol (e.g. propylene glycol, polyethylene glycol) or a nonionic surfactant (e.g. Polysorbate 80, HCO-50). An oily liquid for injection includes sesame oil and soybean oil and may be used in combination with a solubilizer such as benzyl benzoate or benzyl alcohol. In addition, a buffer (e.g. phosphate buffer, sodium acetate buffer), a soothing agent (e.g. benzalkonium chloride, procaine hydrochloride etc.), a stabilizer (e.g. human serum albumin, polyethylene glycol etc.), a preservative (e.g. benzyl alcohol, phenol etc.) and the like may be added. The injection thus obtained is usually filled in an ampule.

The pharmaceutical composition of the present invention can be appropriately used in combination with a drug (hereinafter, abbreviated as a concomitant drug) such as a thrombolytic agent (e.g. TPA, urokinase etc.), an Alzheimer's disease treating drug (e.g. Avan, Calan etc.), a cholesterol treating drug (e.g. an HMG-CoA reductase inhibitor such as simvastatin, pravastatin etc.), a TG lowering drug (e.g. clofibrate etc.), an AII antagonist (e.g. candesartan cilexetil, losartan etc.), an anti-platelet drug (e.g. clopidogrel, abciximab, aspirin etc.), a Ca antagonist (e.g. Calslot, amlodipine etc.), an ACE inhibitor (e.g. enalapril, captopril etc.), a β blocker (e.g. metoprolol, carvedilol etc.) or an antiarrhythmic drug (e.g. procaine amide etc.). The concomitant drug may be a low-molecular compound, a high-molecular protein, a polypeptide, an antibody, or a vaccine. An administration mode of the compound of the present invention and a concomitant drug is not limited particularly, as long as the compound of the present invention and the concomitant drug are combined upon administration. For example, such an administration mode includes (1) administration of a single preparation obtained by formulating the compound of the present invention and a concomitant drug simultaneously, (2) simultaneous administration of two kinds of preparations obtained by formulating the compound of the present invention and a concomitant drug separately, via a single administration route, (3) separate administration at an interval of two kinds of preparations obtained by formulating the compound of the present invention and a concomitant drug separately, via a single administration route, (4) simultaneous administration of two kinds of preparations obtained by formulating the compound of the present invention and a concomitant drug separately, via different administration routes, and (5) separate administration at an interval of two kinds of preparations obtained by formulating the compound of the present invention and a concomitant drug separately, via different administration routes (e.g. administration of the compound of the present invention followed by the concomitant drug, or administration in the reverse order). The dose of a concomitant drug can be selected appropriately on the basis of a dose clinically used. In addition, a combination ratio of the compound of the present invention and a concomitant drug can be selected appropriately depending on a subject to be administered, an administration route, a disease to be treated, symptom, and a combination thereof. For example, when a subject to be administered is a human, 0.01 to 100 parts by weight of a concomitant drug may be used based on 1 part by weight of the compound of the present invention.

BEST MODE FOR CARRYING OUT THE INVENTION

The present invention is further illustrated by the following Examples, Formulation Examples and Experimental Examples which are merely examples and do not limit the present invention, and various changes may be made without departing from the scope of the present invention.

In Examples, elution of column chromatography was confirmed under observation with TLC (Thin Layer Chromatography). For TLC observation, 60F$_{254}$ manufactured by Merck or NH manufactured by Fuji Silysia Chemical Ltd. as a TLC plate, a solvent used as an eluting solvent in column chromatography as a developing solvent, and a UV detector as a detection method were used. As a silica gel for a column, Kiesel Gel 60 (70 to 230 mesh) or Kiesel Gel 60 (230 to 400 mesh) manufactured by Merck was used. As a basic silica gel for a column, basic silica NH-DM1020 (100 to 200 mesh) manufactured by Fuji Silysia Chemical Ltd. was used. NMR spectrum was measured with a Varian Gemini 200-type or Mercury 300-type spectrometer using tetramethylsilane as an internal or external standard, and chemical shift was expressed as δ value and a coupling constant was expressed as Hz. IR spectrum was measured with Shimadzu FTZR-8200-type spectrometer. A numerical value shown within ( ) for a mixed solvent is a mixing ratio by volume of each solvent. In addition, % for a solution shows the amount (gram) of a solute in 100 ml of a solution. In addition, symbols used in Examples have the following meanings.

s: singlet
d: doublet
t: triplet
q: quartet
dd: double doublet
m: multiplet
br: broad
brs: broad singlet
J: coupling constant
THF: tetrahydrofuran
DMF: N,N'-dimethylformamide
DMSO: diemthylsulfoxide
CDI: N,N'-carbonyldiimidazole
WSC: water-soluble carbodiimides
HOBt: 1-hydroxybenztriazole

REFERENCE EXAMPLE 1

(2S)-3-[(6-Chloronaphthalen-2-yl)thio]-2-hydroxypropionic acid

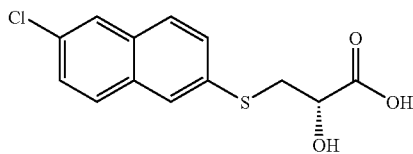

1a) Methyl (2S)-3-[(6-chloronaphthalen-2-yl)thio]-2-hydroxypropionate

Under an argon atmosphere, a solution of 3M ethyl magnesium bromide in diethyl ether was added dropwise to THF (25 mL) under ice-cooling. To this solution was added dropwise a solution of 6-chloronaphthalene-2-thiol (5.0 g) in THF (50 mL) at 0° C. and the mixture was stirred at room temperature for 30 minutes. To the resulting solution was added dropwise a solution of methyl (2R)-oxylane-2-carboxylate (2.3 mL) in THF (15 mL) and the mixture was stirred at room temperature for 3 hours. An aqueous ammonium chloride solution (50 mL) was added to the reaction mixture and the mixture was extracted with ethyl acetate (100 mL). The extract was washed with saturated saline solution, dried over anhydrous magnesium sulfate and concentrated under reduced pressure. The residue was recrystallized from hexane/ethyl acetate (3:1) to obtain the title compound (5.9 g, 77%) as colorless needle-like crystals.

NMR (CDCl$_3$) δ: 3.12 (1H, d, J=6.0), 3.35 (1H, dd, J=14.1, 5.7), 3.48 (1H, dd, J=14.1, 4.2), 3.58 (3H, s), 4.43-4.48 (1H, m), 7.39-7.43 (1H, m), 7.49-7.52 (1H, m), 7.66-7.69 (2H, m), 7.76-7.77 (1H, m), 7.83-7.84 (1H, m).

1b) (2S)-3-[(6-Chloronaphthalen-2-yl)thio]-2-hydroxypropionic acid

An aqueous 8N sodium hydroxide solution (6.8 mL) was added to a suspension of methyl (2S)-3-[(6-chloronaphthalen-2-yl)thio]-2-hydroxypropionate (5.4 g) obtained in Reference Example 1a) in ethanol (150 mL) and the mixture was stirred at room temperature for 3 hours. Ethanol was distilled off under reduced pressure and then the resulting precipitate was obtained by filtration. The solid was suspended in water (100 mL), pH of the suspension was adjusted to about 3 with 1N hydrochloric acid and then the precipitate was collected by filtration to obtain the title compound (5.0 g, 97%) as a white solid.

NMR (CD$_3$OD) δ: 3.27 (1H, dd, J=14.1, 6.9), 3.51 (1H, dd, J=14.1, 4.2), 4.33 (1H, dd, J=6.9, 4.2), 7.40-7.43 (1H, m), 7.51-7.54 (1H, m), 7.71-7.77 (2H, m), 7.82 (1H, s), 7.86 (1H, s).

EXAMPLE 1

1'-{(2S)-3-[(6-Chloronaphthalen-2-yl)sulfonyl]-2-hydroxypropanoyl}-1,4'-bipiperidin-2-one

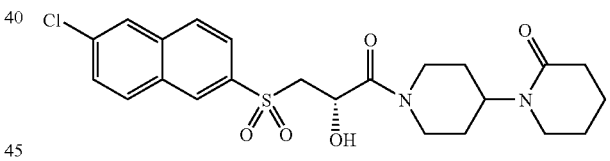

WSC (0.19 g) was added to a mixture of (2S)-3-[(6-chloronaphthalen-2-yl)sulfonyl]-2-hydroxypropionic acid (0.31 g), 1,4'-bipiperidin-2-one (0.18 g) and HOBt (0.15 g) in DMF (15 mL) and the mixture was stirred at room temperature for 15 hours. The reaction mixture was concentrated under reduced pressure, and diluted with dichloromethane and an aqueous sodium bicarbonate solution. The organic layer was separated, dried over anhydrous sodium sulfate, and concentrated under reduced pressure. The residue was purified by basic silica gel column chromatography (ethyl acetate to ethyl acetate/methanol=10/1) to obtain the title compound (0.26 g, 54%) as a colorless powder.

NMR (CDCl$_3$) δ: 1.62-1.79 (9H, m), 2.41-2.45 (2H, m), 2.68-2.82 (1H, m), 3.14-3.26 (3H, m), 3.40-3.48 (2H, m), 3.97-4.01 (1H, m), 4.60-4.68 (1H, m), 4.80-4.84 (1H, m), 4.96-5.04 (1H, m), 7.59(1H, dd, J=2.1, 8.7), 7.94-7.97 (4H, m), 8.51 (1H, s).

Elemental analysis for $C_{23}H_{27}ClN_2O_5S \cdot H_2O \cdot 0.2CH_2Cl_2$
Calcd (%): C, 54.21; H, 5.77; N, 5.45
Found (%): C, 54.44; H, 5.56; N, 5.17

EXAMPLE 2

1-(1-{(2S)-3-[(6-Chloronaphthalen-2-yl)sulfonyl]-2-hydroxypropanoyl}piperidin-4-yl)pyrrolidin-2-one

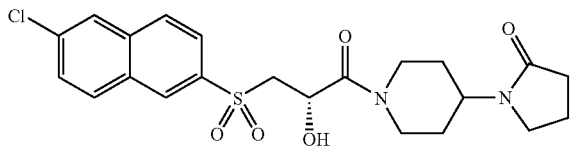

According to the manner similar to that in Example 1, the title compound (0.19 g, 41%) was obtained as a colorless powder from 1-(4-piperidinyl)-2-pyrrolidinone.

NMR (CDCl$_3$) δ: 1.62-1.87 (3H, m), 2.01-2.08 (3H, m), 2.39-2.44 (2H, m), 2.66-2.81 (1H, m), 3.13-3.48 (5H, m), 3.75-4.24 (3H, m), 4.61-4.65 (1H, m), 5.02-5.03 (1H, m), 7.59 (1H, dd, J=2.1, 8.7), 7.94-7.97 (4H, m), 8.51 (1H, s).

Elemental analysis for $C_{22}H_{25}ClN_2O_5S \cdot 0.5H_2O$

Calcd (%): C, 55.75; H, 5.53; N, 5.91

Found (%): C, 55.63; H, 5.74; N, 5.71

EXAMPLE 3

1-(1-{3-[(6-Chloronaphthalen-2-yl)sulfonyl]propanoyl}piperidin-4-yl)pyrrolidin-2-one

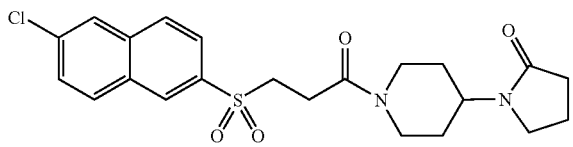

After 3-((6-chloronaphthalen-2-yl)sulfonyl)propinoic acid (0.30 g), HOBt (0.23 g) and WSC (0.29 g) were dissolved in DMF (10 mL), 1-(piperidin-4-yl)-2-pyrrolidinone (0.17 g) and triethylamine (0.10 g) were added thereto, and the mixture was stirred at room temperature for 15 hours. The reaction mixture was concentrated under reduced pressure, and diluted with ethyl acetate and an aqueous sodium bicarbonate solution. The organic layer was separated, dried over anhydrous sodium sulfate, and concentrated under reduced pressure. The residue was purified by basic silica gel column chromatography (ethyl acetate to ethyl acetate/methanol 10/1) to obtain the title compound (0.17 g, 39%) as a colorless powder.

NMR (CDCl$_3$) δ: 1.45-1.80 (4H, m), 1.97-2.07 (2H, m), 2.40 (2H, t, J=4.9), 2.53-2.62 (1H, m), 2.84-2.99 (2H, m), 3.08-3.18 (1H, m), 3.29 (2H, t, J=7.1), 3.47-3.63 (2H, m), 3.88-3.94 (1H, m), 4.11-4.21 (1H, m), 4.61-4.66 (1H, m), 7.60 (1H, dd, J=1.9, 8.9), 7.89-7.97 (4H, m), 8.48 (1H, s).

Elemental analysis for $C_{22}H_{25}ClN_2O_4S$

Calcd (%): C, 58.85; H, 5.61; N, 6.24

Found (%): C, 58.89; H, 5.77; N, 6.25

EXAMPLE 4

3-(1-{(2S)-3-[(6-chloronaphthalen-2-yl)sulfonyl]-2-hydroxypropanoyl}piperidin-4-yl)-1,3-oxazolidin-2-one

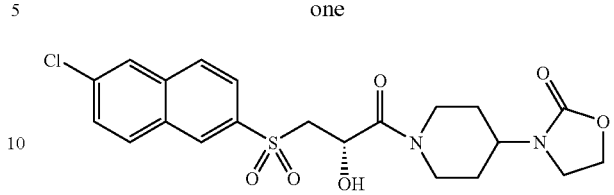

According to the manner similar to that described in Example 1, the title compound (0.19 g, 41%) was obtained as a colorless powder from 3-(piperidin-4-yl)-1,3-oxazolidin-2-one (0.17 g).

NMR (CDCl$_3$) δ: 1.52-1.95 (4H, m), 2.67-2.82 (1H, m), 3.13-3.26 (1H, m), 3.41-3.56 (4H, m), 3.68-3.84 (1H, m), 3.95-4.03 (2H, s), 4.36 (2H, t, J=8.0), 4.62-4.67 (1H, m), 4.96-5.06 (1H, m), 7.60 (1H, dd, J=2.1, 8.9), 7.91-7.97 (4H, m), 8.51 (1H, s).

Elemental analysis for $C_{21}H_{23}ClN_2O_6S \cdot 0.5H_2O$

Calcd (%): C, 52.99; H, 5.08; N, 5.89

Found (%): C, 52.91; H, 5.06; N, 5.91

EXAMPLE 5

2-(1-{(2S)-3-[(6-Chloronaphthalen-2-yl)sulfonyl]-2-hydroxypropanoyl}piperidin-4-yl)isoindolin-1-one

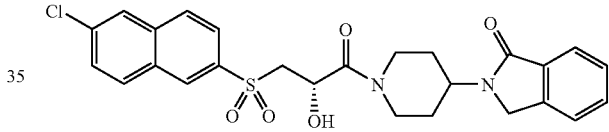

According to the manner similar to that in Example 1, the title compound (0.13 g, 25%) was obtained as a colorless powder from 2-(piperidin-4-yl)isoindolin-1-one (0.22 g).

NMR (CDCl$_3$) δ: 1.68-1.87 (3H, m), 1.88-2.05 (2H, m), 2.77-2.90 (1H, m), 3.22-3.35 (1H, m), 3.44-3.51 (2H, m), 4.05-4.10 (1H, m), 4.33-4.36 (2H, m), 4.52-4.60 (1H, m), 4.68-4.76 (1H, m), 5.00-5.08 (1H, m), 7.46-7.61 (4H, m), 7.86 (1H, d, J=7.4), 7.95-7.98 (4H, m), 8.52 (1H, s).

Elemental analysis for $C_{26}H_{25}ClN_2O_5S \cdot H_2O$

Calcd (%): C, 58.81; H, 5.12; N, 5.28

Found (%): C, 58.74; H, 5.17; N, 5.24

EXAMPLE 6

(R,S)-1-(1-{3-[(6-Chloronaphthalen-2-yl)sulfonyl]-2-hydroxypropanoyl}piperidin-4-yl)pyrrolidin-2-one

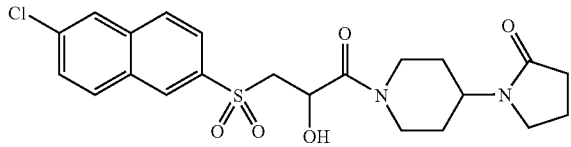

According to the manner similar to that in Example 1, the title compound (0.15 g, 32%) was obtained as a colorless powder from (R,S)-3-((6-chloronaphthalen-2-yl)sulfonyl)-2-hydroxypropinoic acid (0.31 g).

NMR (CDCl$_3$) δ: 1.55-1.87 (3H, m), 2.01-2.05 (3H, m), 2.39-2.44 (2H, m), 2.70-2.81 (1H, m), 3.13-3.48 (5H, m), 3.75-4.24 (3H, m), 4.59-4.66 (1H, m), 4.98-5.04 (1H, m), 7.60(1H, dd, J=2.1, 8.7), 7.94-7.98 (4H, m), 8.51 (1H, s).

Elemental analysis for C$_{22}$H$_{25}$ClN$_2$O$_5$S.1.5H$_2$O.0.4AcOEt

Calcd (%): C, 53.76; H, 5.96; N, 5.31

Found (%): C, 53.88; H, 5.57; N, 4.94

EXAMPLE 7

4-(1-{(2S)-3-[(6-Chloronaphthalen-2-yl)sulfonyl]-2-hydroxypropanoyl}piperidin-4-yl)morpholin-3-one

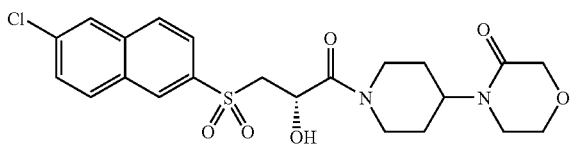

7a) Benzyl 4-[(2-hydroxyethyl)amino]piperidin-1-carboxylate

A solution of benzyl 4-oxopiperidin-1-carboxylate (7.0 g), 2-aminoethanol (2.8 g) and acetic acid (2.7 g) in 1,2-dichloroethane (150 mL)-methanol (10 mL) was stirred at room temperature for 3 hours, sodium triacetoxyborohydride (12.7 g) was added thereto, and the mixture was stirred at room temperature for 15 hours. A 1N sodium hydroxide solution was added to the reaction mixture, pH of the aqueous layer was adjusted to about 12, and then the organic layer was separated. The organic layer was dried over anhydrous sodium sulfate, and the solvent was distilled off under reduced pressure to obtain the title compound (9.0 g, quantitative) as a colorless oil.

NMR (CDCl$_3$) δ: 1.21-1.33 (2H, m), 1.86-1.97 (4H, m), 2.58-2.67 (1H, m), 2.78-2.92 (4H, m), 3.63 (2H, t, J=5.2), 4.10 (2H, br), 5.12 (2H, s), 7.29-7.36 (5H, m).

7b) Benzyl 4-(3-oxo-4-morpholinyl)piperidin-1-carboxylate

Benzyl 4-[(2-hydroxyethyl)amino]piperidin-1-carboxylate (7.5 g) obtained in Example 7a) and triethylamine (4.1 mL) were dissolved in THF (70 mL), chloroacetyl chloride (2.2 mL) was added dropwise thereto with cooling at 0° C., and the mixture was stirred at 0° C. for 2 hours. The solvent was distilled off under reduced pressure, the residue was diluted with water, and the mixture was extracted with ethyl acetate. The extract was washed with a 5% aqueous citric acid solution and a saturated saline solution, and dried over anhydrous sodium sulfate, and the solvent was distilled off under reduced pressure. The residue was dissolved in DMF (60 mL), the solution was cooled to 0° C., and then sodium hydride (60% in oil; 1.2 g) was added to the reaction mixture. The mixture was stirred at 0° C. for one hour, at room temperature for one hour and at 80° C. for 15 hours. The reaction mixture was concentrated under reduced pressure, water was added thereto, the solution was acidified with 1N hydrochloric acid, and the mixture was extracted with ethyl acetate. The extract was washed with water and saturated saline solution, and dried over anhydrous sodium sulfate, and the solvent was distilled off under reduced pressure. The residue was purified by silica gel column chromatography (ethyl acetate/hexane=2/1 to ethyl acetate) to obtain the title compound (3.8g, 44%) as a colorless oil.

NMR (CDCl$_3$) δ: 1.56-1.69 (4H, m), 2.85-2.93 (2H, m), 3.24 (2H, t, J=5.1), 3.87 (2H, t, J=5.1), 4.19 (2H, s), 4.31 (2H, br), 4.60-4.71 (1H, m), 5.13 (2H, s), 7.29-7.37 (5H, m).

7c) 4-(Piperidin-4-yl)morpholin-3-one

Benzyl 4-(3-oxo-4-morpholinyl)piperidin-1-carboxylate (3.8 g) obtained in Example 7b) was dissolved in ethanol (50 mL), 10% palladium on carbon (containing 50% water; 0.38 g) was added thereto, and the mixture was stirred at room temperature for 15 hours under a hydrogen atmosphere. The reaction mixture was filtered and the solvent was distilled off under reduced pressure to obtain the title compound (2.2 g, quantitative) as a light yellow oil.

NMR (CDCl$_3$) δ: 1.54-1.69 (5H, m), 2.75 (2H, dt, J=3.0, 11.3), 3.13-3.17 (2H, m), 3.31 (2H, t, J=5.1), 3.88 (2H, t, J=5.1), 4.19 (2H, s), 4.52-4.63 (1H, m).

7d) 4-(1-{(2S)-3-[(6-chloronaphthalen-2-yl)sulfonyl]-2-hydroxypropanoyl}piperidin-4-yl)morpholin-3-one 4-(Piperidin-4-yl)morpholin-3-one (0.18 g) obtained in Example 7c), (2S)-3[(6-chloronaphthalen-2-yl)sulfony]-2-hydroxypropionic acid (0.31 g) and HOBt (0.23 g) were dissolved in DMF (10 mL), WSC (0.29 g) was added thereto, and the mixture was stirred at room temperature for 15 hours. The reaction mixture was concentrated under reduced pressure, and the residue was diluted with an aqueous sodium bicarbonate solution, and extracted with ethyl acetate. The extract was washed successively with water, an aqueous 5% citric acid solution, and saturated saline solution, and dried over sodium sulfate, and the solvent was distilled off under reduced pressure. The residue was purified by silica gel column chromatography (from ethyl acetate to ethyl acetate/methanol=5/1) to obtain the title compound (0.20 g, 42%) as a colorless powder.

NMR (CDCl$_3$) δ: 1.60-1.82 (4H, m), 2.69-2.83 (1H, m), 3.15-3.29 (3H, m), 3.41-3.48 (2H, m), 3.67-3.90 (3H, m), 4.02-4.05 (1H, m), 4.20 (2H, s), 4.62-4.80 (2H, m), 5.02 (1H, m), 7.58-7.61 (1H, m), 7.94-7.97 (4H, m), 8.51 (1H, s).

Elemental analysis for C$_{22}$H$_{25}$ClN$_2$O$_6$S.0.5H$_2$O

Calcd (%): C, 53.93; H, 5.35; N, 5.72

Found (%): C, 53.82; H, 5.22; N, 5.52

EXAMPLE 8

1-(4-{(2S)-3-[(6-Chloronaphthalen-2-yl)sulfonyl]-2-hydroxypropanoyl}piperazin-1-yl)piperidin-2-one

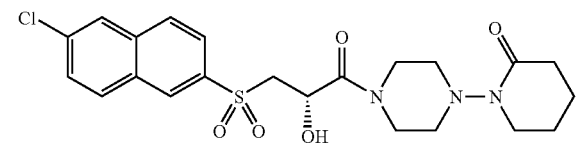

8a) 1-(4-Benzylpiperazin-1-yl)piperidin-2-one

To a solution of 4-benzylpiperazin-1-amine (3.0 g) in DMF (70 mL) was added dropwise 5-bromovarelyl chloride (3.1 g) at 0° C. and the mixture was further stirred at the same temperature for 2 hours. Sodium hydride (60% in oil; 1.3 g) was added to the reaction mixture, and the mixture was stirred at 0° C. for 10 minutes, at room temperature for 30 minutes, and at 80° C. for 15 hours. The solvent was distilled off under reduced pressure, and the residue was diluted with water and extracted with dichloromethane. The extract was dried over anhydrous sodium sulfate, and the solvent was distilled off under reduced pressure. The residue was purified by basic silica gel column chromatography (ethyl acetate/hexane=1/4) to obtain the title compound (3.0g, 70%) as a yellow oil.

NMR (CDCl₃) δ: 1.67-1.81 (4H, m), 2.37 (2H, t, J=6.6), 2.53 (4H, br), 2.74 (2H, t, J=4.9), 3.18 (2H, br), 3.37 (2H, t, J=6.0), 3.52 (2H, s), 7.23-7.35 (5H, m).

8b) 1-(Piperazin-1-yl)piperidin-2-one

To a solution of 1-(4-benzylpiperazin-1-yl)piperidin-2-one (1.0 g) obtained in Example 8a) in methanol (15 mL) was added 20% palladium hydroxide on carbon (containing 50% water, 0.20 g), and the mixture was stirred at room temperature for 15 hours under a hydrogen atmosphere. The reaction mixture was filtered, and the solvent was distilled off under reduced pressure to obtain the title compound (0.65 g, 97%) as a yellow solid.

NMR (CDCl₃) δ: 1.65-1.85 (4H, m), 2.33-2.39 (2H, m), 2.66-3.81 (10H, m).

8c) 1-(4-{(2S)-3-[(6-Chloronaphthalen-2-yl)sulfonyl]-2-hydroxypropanoyl}piperazin-1-yl)piperidin-2-one 1-(Piperazin-1-yl)piperidin-2-one (0.44 g) obtained in Example 8b), (2S)-3-[(6-chloronaphthalen-2-yl)sulfony]-2-hydroxypropionic acid (0.76 g), HOBt (0.37 g) and triethylamine (0.34 mL) were dissolved in DMF (10 mL), WSC (0.46 g) was added thereto, and the mixture was stirred at room temperature for 15 hours. The reaction mixture was concentrated under reduced pressure, and the residue was diluted with an aqueous sodium bicarbonate solution, and extracted with dichloromethane. The extract was washed with an aqueous sodium bicarbonate solution and dried over sodium sulfate, and the solvent was distilled off under reduced pressure. The residue was purified by silica gel column chromatography (ethyl acetate to ethyl acetate/methanol=10/1), and recrystallized form ethyl acetate to obtain the title compound (0.32 g, 28%) as a colorless powder.

m.p. 198° C. NMR (CDCl₃) δ: 1.67-1.75 (2H, m), 1.79-2.05 (2H, m), 2.36 (2H, t, J=6.4), 3.16-3.80 (13H, m), 4.99 (1H, m), 7.58 (1H, dd, J=1.7, 8.7), 7.94-7.97 (4H, m), 8.51 (1H, s).

Elemental analysis for C₂₂H₂₆ClN₃O₅S
Calcd (%): C, 55.05; H, 5.46; N, 8.75
Found (%): C, 54.78; H, 5.45; N, 8.81

EXAMPLE 9

1-(1-{(2S)-3-[(6-Chloronaphthalen-2-yl)sulfonyl]-2-hydroxypropanoyl}piperidin-4-yl)azepan-2-one

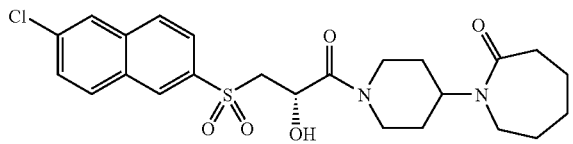

9a) Benzyl 4-(2-oxoazepan-1-yl)piperidin-1-carboxylate

To a solution of benzyl 4-aminopiperidin-1-carboxylate (1.7 g) and triethylamine (1.1 mL) in THF (40 mL) was added dropwise 5-bromohexanoyl chloride (1.1 mL), and the mixture was stirred at 0° C. for 2 hours. The solvent was distilled off under reduced pressure and the residue was diluted with water, and extracted with ethyl acetate. The extract was washed with an aqueous 5% citric acid solution and a saturated saline solution, and dried over anhydrous sodium sulfate, and the solvent was distilled off under reduced pressure. The residue was dissolved in DMF (40 mL), and cooled at 0° C., sodium hydride (60% in oil; 0.60 g) was added thereto, and the mixture was stirred at 0° C. for one hour, at room temperature for one hour and at 80° C. for 15 hours. The solvent was distilled off under reduced pressure, the residue was diluted with water, and the solution was acidified with 1N hydrochloric acid, and extracted with ethyl acetate. The extract was washed with water and saturated saline solution, and dried over anhydrous sodium sulfate, and the solvent was distilled off under reduced pressure. The residue was purified by silica gel column chromatography (ethyl acetate/hexane=2/1 to 5/1) to obtain the title compound (0.25 g, 10%) as a yellow oil.

NMR (CDCl₃) δ: 1.52-1.69 (10H, m), 2.52-2.55 (2H, m), 2.80-2.90 (2H, m), 3.20-3.24 (2H, m), 4.25 (2H, br), 4.63-4.72 (1H, m), 5.13 (2H, s), 7.26-7.37 (5H, m).

9b) 1-(Piperidin-4-yl)azepan-2-one

To a solution of benzyl 4-(2-oxoazepan-1-yl)piperidin-1-carboxylate (0.25 g) obtained in Example 9a) in ethanol (10 mL) was added 10% palladium on carbon (containing 50% water; 0.03 g), and the mixture was stirred at room temperature for 15 hours under a hydrogen atmosphere. The reaction mixture was filtered, and the solvent was distilled off under reduced pressure to obtain the title compound (0.15 g, quantitative) as a brown oil.

NMR (CDCl₃) δ: 1.46-1.69 (11H, m), 2.52-2.56 (2H, m), 2.71 (2H, dt, J=2.9, 11.9), 3.09-3.13 (2H, m), 3.28-3.31 (2H, m), 4.53-4.63 (1H, m).

9c) 1-(1-{(2S)-3-[(6-chloronaphthalen-2-yl)sulfonyl]-2-hydroxypropanoyl}piperidin-4-yl)azepan-2-one According to the manner similar to that in Example 1, the title compound (0.10 g, 27%) was obtained as a colorless powder from 1-(piperidin-4-yl)azepan-2-one (0.15 g) obtained in Example 9b).

NMR (CDCl₃) δ: 1.50-1.71 (10H, m), 2.55-2.57 (2H, m), 2.67-2.81 (1H, m), 3.12-3.24 (3H, m), 3.39-3.46 (2H, m), 3.71-3.87 (1H, m), 3.95-4.00 (1H, m), 4.58-4.66 (1H, m), 4.75-4.83 (1H, m), 5.02 (1H, m), 7.59 (1H, dd, J=2.3, 8.7), 7.94-7.97 (4H, m), 8.51 (1H, s).

Elemental analysis for C₂₄H₂₉ClN₂O₅S
Calcd (%): C, 58.47; H, 5.93; N, 5.68
Found (%): C, 58.24; H, 5.75; N, 5.56

EXAMPLE 10

1-(1-{(2S)-3-[(6-Chloronaphthalen-2-yl)sulfonyl]-2-hydroxypropanoyl}piperidin-4-yl)imidazolidin-2-one

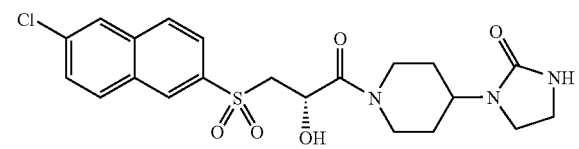

According to the manner similar to that in Example 1, the title compound (0.22 g, 46%) was obtained as a colorless powder from 1-(piperidin-4-yl)-2-imidazolidinone (0.17 g).

NMR (CDCl₃) δ: 1.55-1.64 (2H, m), 1.77-1.85 (2H, m), 2.66-2.77 (1H, m), 3.11-3.24 (1H, m), 3.37-3.45 (6H, m), 3.75-3.88 (1H, m), 3.97-4.02 (2H, m), 4.40 (1H, s), 4.61-4.66 (1H, m), 4.98-5.03 (1H, m), 7.59 (1H, dd, J=2.3, 8.7), 7.94-7.97 (4H, m), 8.51 (1H, s).

Elemental analysis for $C_{21}H_{24}ClN_3O_5S$

Calcd (%): C, 54.13; H, 5.19; N, 9.02

Found (%): C, 54.06; H, 5.16; N, 8.95

EXAMPLE 11

1-(1-{(2S)-3-[(6-Chloronaphthalen-2-yl)sulfonyl]-2-hydroxypropanoyl}piperidin-4-yl)tetrahydropyrimidin-2(1H)-one

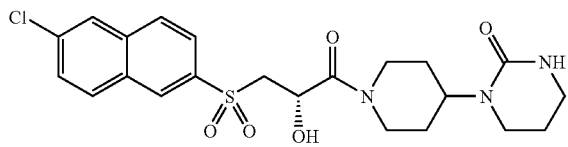

(2S)-3-[(6-Chloronaphthalen-2-yl)sulfonyl]-2-hydroxypropionic acid, 1-(piperidin-4-yl)tetrahydropyrimidin-2(1H)-one, and HOBt (23.0 g) were dissolved in DMF, WSC was added thereto, and the mixture was stirred at room temperature for 15 hours. The reaction mixture was concentrated under reduced pressure, diluted with an aqueous sodium bicarbonate solution, and extracted with dichloromethane. The extract was washed with an aqueous 5% citric acid solution and saturated saline solution, and dried over sodium sulfate, and the solvent was distilled off under reduced pressure. The residue was purified by silica gel column chromatography (ethyl acetate to ethyl acetate/methanol=10/1) to obtain the title compound as a colorless powder.

Crystal A

The above colorless amorphous material was dissolved in heated ethyl acetate, and crystallized to obtain colorless crystals as Crystal A.

m.p. 173° C NMR (CDCl$_3$) δ: 1.57-1.78 (4H, m), 1.90-1.93 (2H, m), 2.70-2.76 (1H, m), 3.11-3.20 (3H, m), 3.27-3.30 (2H, m), 3.40-3.48 (2H, m), 3.78-3.90 (1H, m), 3.94-3.99 (1H, m), 4.56-4.66 (3H, m), 4.97-5.03 (1H, m), 7.59(1H, dd, J=1.8, 8.7), 7.94-7.97 (4H, m), 8.51 (1H, s).

Elemental analysis for $C_{22}H_{26}ClN_3O_5S$

Calcd (%): C, 55.05; H, 5.46; N, 8.75

Found (%): C, 54.96; H, 5.57; N, 8.80

Crystal B

The above colorless amorphous material was dissolved in heated methanol, concentrated to remove about one half of the solvent, and crystallized to obtain colorless crystals as Crystal B.

m.p. 185° C.

EXAMPLE 12

1-(1-{(2S)-3-[(6-chloronaphthalen-2-yl)sulfonyl]-2-hydroxypropanoyl}piperidin-4-yl)-4-methylpiperazin-2-one

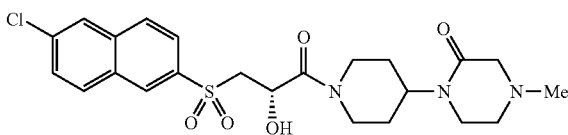

12a) Benzyl 4-({2-[(tert-butoxycarbonyl)amino]ethyl}amino)piperidin-1-carboxylate According to the manner similar to that in Example 7a), the title compound (20 g, quantitative) was obtained as a colorless oil from tert-butyl (2-aminoethyl)carbamate (8.5 g).

NMR (CDCl$_3$) δ: 1.23-1.37 (3H, m), 1.44 (9H, s), 1.83-1.87 (2H, m), 2.59-2.66 (1H, m), 2.75 (2H, t, J=5.9), 2.85-2.93 (2H, m), 3.17-3.23 (2H, m), 4.08-4.11 (2H, m), 4.89 (1H, br), 5.12 (2H, s), 7.30-7.36 (5H, m).

12b) tert-Butyl 4-{1-[(benzoyloxy)carbonyl]piperidin-4-yl}-3-oxopiperazin-1-carboxylate According to the manner similar to that in Example 7b), the title compound (4.7 g, 43%) was obtained as a yellow oil from benzyl 4-({2-[(tert-butoxycarbonyl)amino]ethyl}amino)piperidin-1-carboxylate (10 g) obtained in Example 12a).

NMR (CDCl$_3$) δ: 1.47 (9H, s), 1.53-1.68 (4H, m), 2.88 (2H, m), 3.22 (2H, t, J=5.3), 3.59 (2H, t, J 5.3), 4.09 (2H, m), 4.30 (2H, br), 4.63-4.68 (1H, m), 5.13 (2H, s), 7.35-7.37 (5H, m).

12c) Benzyl 4-(4-methyl-2-oxopiperazin-1-yl)piperidin-1-carboxylate tert-Butyl 4-{1-[(benzoyloxy)carbonyl]piperidin-4-yl}-3-oxopiperazin-1-carboxylate (0.42 g) obtained in Example 12b) was dissolved in trifluoroacetic acid (1 mL) and dichloromethane (1 mL), and the mixture was stirred at room temperature for one hour. The reaction mixture was concentrated, toluene was added to the residue and it was concentrated again under reduced pressure. The residue was dissolved in dichloromethane (15 mL) and formalin (37%; 0.5 mL) was added. After the reaction mixture was stirred at room temperature for 2 hours, sodium triacetoxyborohydride (0.53 g) was added, and the mixture was stirred at room temperature for 15 hours. The reaction mixture was washed with an aqueous sodium bicarbonate solution and dried over anhydrous sodium sulfate, and the solvent was distilled off under reduced pressure to obtain the title compound (0.38 g, quantitative) as a light yellow oil.

NMR (CDCl$_3$) δ: 1.62 (4H, br), 2.32 (3H, s), 2.62 (2H, t, J=5.4), 2.88 (2H, m), 3.12 (2H, s), 3.22 (2H, t, J=5.4), 4.30 (2H, br), 4.59-4.70 (1H, m), 5.12 (2H, s), 7.34-7.37 (5H, m).

12d) 4-Methyl-1-(piperidin-4-yl)piperazin-2-one

According to the manner similar to that in Example 7c), the title compound (0.20 g, 43%) was obtained as a light yellow oil from benzyl 4-(4-methyl-2-oxopiperazin-1-yl)piperidin-1-carboxylate (0.33 g) obtained in Example 12c).

NMR (CDCl$_3$) δ: 1.56-1.66 (5H, m), 2.32 (3H, s), 2.61-2.64 (2H, m), 2.69-2.78 (2H, m), 3.12-3.16 (4H, m), 3.28 (2H, t, J=5.4), 4.51-4.61 (1H, m).

12e) 1-(1-{(2S)-3-[(6-Chloronaphthalen-2-yl)sulfonyl]-2-hydroxypropanoyl}piperidin-4-yl)-4-methylpiperazin-2-one According to the manner similar to that in Example 1, the title compound (0.24 g, 49%) was obtained as a colorless powder from 4-methyl-1-(piperidin-4-yl)piperazin-2-one (0.20 g) obtained in Example 12d).

NMR (CDCl$_3$) δ: 1.64-1.79 (4H, m), 2.33 (3H, s), 2.62-2.77 (3H, m), 3.14 (2H, s), 3.19-3.27 (3H, m), 3.40-3.48 (2H, m), 3.70-3.84 (1H, m), 3.98-4.02 (1H, m), 4.62-4.74 (2H, m), 5.01 (1H, m), 7.60 (1H, dd, J=1.8, 8.7), 7.94-7.97 (4H, m), 8.51 (1H, s).

Elemental analysis for $C_{23}H_{28}ClN_3O_5S \cdot 0.5H_2O$

Calcd (%): C, 54.92; H, 5.81; N, 8.35

Found (%): C, 54.71; H, 5.81; N, 8.38

EXAMPLE 13

1-(1-{(2S)-3-[(6-Chloronaphthalen-2-yl)sulfonyl]-2-hydroxypropanoyl}piperidin-4-yl)-3-methylimidazolidin-2-one

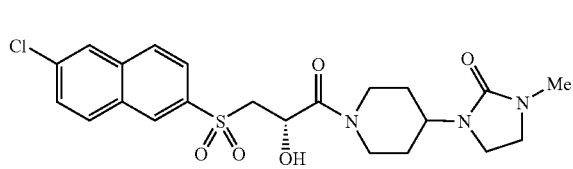

13a) Benzyl 4-(3-methyl-2-oxoimidazolidin-1-yl)piperidin-1-carboxylate

Sodium hydride (80 mg) was added to a solution of benzyl 4-(2-oxoimidazolidin-1-yl)piperidin-1-carboxylate (0.30 g) in DMF (5 mL), the mixture was stirred at room temperature for 30 minutes. After addition of methyl iodide (0.25 mL), the mixture was stirred at room temperature for 15 hours. The reaction mixture was concentrated under reduced pressure, diluted with water, and extracted with ethyl acetate. The extract was washed with water, an aqueous 5% citric acid solution and saturated saline solution and dried over anhydrous sodium sulfate, and the solvent was distilled off under reduced pressure to obtain the title compound (0.32 g, quantitative) as a colorless oil.

NMR (CDCl$_3$) δ: 1.51-1.71 (4H, m), 2.78 (3H, s), 2.82-2.90 (2H, m), 3.20-3.31 (4H, m), 3.86-3.94 (1H, m), 4.27 (2H, br), 5.12 (2H, s), 7.34-7.37 (5H, m).

13b) 1-Methyl-3-(piperidin-4-yl)imidazolidin-2-one

According to the manner similar to that in Example 7c), the title compound (0.18 g, quantitative) was obtained as a colorless oil from the benzyl 4-(3-methyl-2-oxoimidazolidin-1-yl)piperidin-1-carboxylate (0.32 g) obtained in Example 13a).

NMR (CDCl$_3$) δ: 1.48-1.71 (5H, m), 2.66-2.74 (2H, m), 2.78 (3H, m), 3.10-3.14 (2H, m), 3.24-3.29 (4H, m), 3.77-3.85 (1H, m).

13c) 1-(1-{(2S)-3-[(6-Chloronaphthalen-2-yl)sulfonyl]-2-hydroxypropanoyl}piperidin-4-yl)-3-methylimidazolidin-2-one According to the manner similar to that in Example 1, the title compound (0.22 g, 46%) was obtained as a colorless powder from the 1-methyl-3-(piperidin-4-yl)imidazolidin-2-one (0.18 g) obtained in Example 13b).

NMR (CDCl$_3$) δ: 1.54-1.86 (4H, m), 2.66-2.74 (1H, m), 2.79 (3H, s), 3.11-3.33 (5H, m), 3.39-3.47 (2H, m), 3.72-3.85 (1H, m), 3.95-4.01 (2H, m), 4.60-4.64 (1H, m), 4.98-5.04 (1H, m), 7.59 (1H, dd, J=1.7, 8.7), 7.94-8.02 (4H, m), 8.51 (1H, s).

Elemental analysis for C$_{22}$H$_{26}$ClN$_3$O$_5$S.H$_2$O
Calcd (%): C, 53.06; H, 5.67; N, 8.44
Found (%): C, 53.14; H, 5.91; N, 8.62

EXAMPLE 14

1-Benzyl-3-(1-{(2S)-3-[(6-Chloronaphthalen-2-yl)sulfonyl]-2-hydroxypropanoyl}piperidin-4-yl)imidazolidin-2-one

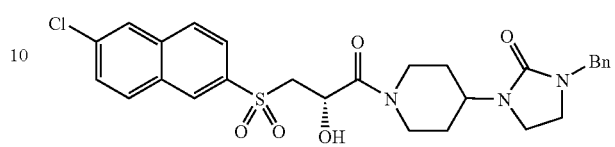

According to the manner similar to that in Example 1, the title compound (0.23 g, 41%) was obtained as a colorless powder from 1-benzyl-3-(piperidin-4-yl)imidazolidin-2-one (0.26 g).

NMR (CDCl$_3$) δ: 1.54-1.86 (4H, m), 2.66-2.79 (1H, m), 3.20-3.24 (5H, m), 3.40-3.44 (2H, m), 3.72-3.84 (1H, m), 3.96-4.16 (2H, m), 4.38 (2H, s), 4.62-4.65 (1H, m), 5.02-5.03 (1H, m), 7.28-7.34 (5H, m), 7.59(1H, dd, J=1.8, 8.7), 7.94-7.97 (4H, m), 8.51 (1H, s).

Elemental analysis for C$_{28}$H$_{30}$ClN$_3$O$_5$S.0.5H$_2$O
Calcd (%): C, 59.51; H, 5.53; N, 7.44
Found (%): C, 59.68; H, 5.80; N, 7.46

EXAMPLE 15

1-(4-{(2S)-3-[(6-chloronaphthalen-2-yl)sulfonyl]-2-hydroxypropanoyl}piperazin-1-yl)pyrrolidin-2-one

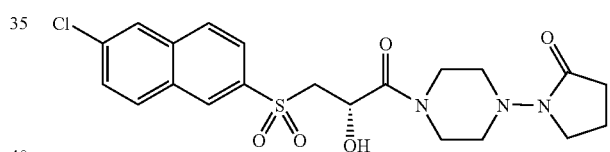

15a) 1-(4-Benzylpiperazin-1-yl)pyrrolidin-2-one

According to the manner similar to that in Example 8a), the title compound (5.10 g, 31%) was obtained as a yellow oil from 4-bromobutanoyl chloride (11.7 g).

NMR (CDCl$_3$) δ: 1.95-2.05 (2H, m), 2.34 (2H, t, J=8.6), 2.61-2.64 (4H, m), 2.94-2.97 (4H, m), 3.45 (2H, t, J=7.0), 3.53 (2H, s), 7.25-7.32 (5H, m).

15b) 1-(Piperazin-1-yl)pyrrolidin-2-one

According to the manner similar to that in Example 8b), the title compound (3.2 g, 95%) was obtained as a colorless oil from the 1-(4-benzylpiperazin-1-yl)pyrrolidin-2-one (5.1 g) obtained in Example 15a).

NMR (CDCl$_3$) δ: 2.00-2.07 (4H, m), 2.33-2.37 (2H, m), 2.93-2.99 (6H, m), 3.45-3.49 (2H, m).

15c) 1-(4-{(2S)-3-[(6-chloronaphthalen-2-yl)sulfonyl]-2-hydroxypropanoyl}piperazin-1-yl)pyrrolidin-2-one According to the manner similar to that in Example 1, the title compound (0.28 g, 30%) was obtained as a colorless powder from the 1-(piperazin-1-yl)pyrrolidin-2-one (0.34 g) obtained in Example 15b).

NMR (CDCl$_3$) δ: 1.99-2.09 (2H, m), 2.36 (2H, t, J=8.4), 3.04-3.14 (4H, m), 3.39-3.50 (4H, m), 3.64-3.85 (5H, m), 4.98-5.03 (1H, m), 7.59 (1H, dd, J=1.9, 8.7), 7.94-7.97 (4H, m), 8.51 (1H, s).
Elemental analysis for C$_{21}$H$_{24}$ClN$_3$O$_5$S
Calcd (%): C, 54.13; H, 5.19; N, 9.02
Found (%): C, 54.07; H, 5.21; N, 9.09

EXAMPLE 16

1-(1-{(2S)-3-[(6-Chloronaphthalen-2-yl)sulfonyl]-2-hydroxypropanoyl}piperidin-4-yl)-1,3-dihydro-2H-imidazol-2-one

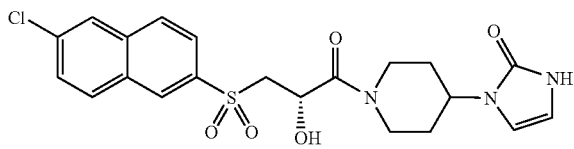

16a) Benzyl 4-({[(2,2-dimethoxyethyl)amino]carbonyl}amino)piperidin-1-carboxylate 2-Aminoacetaldehydedimethylacetal (0.36 g) was added to a solution of benzyl 4-isocyanatopiperidin-1-carboxylate (0.88 g) in acetonitrile (15 mL), and the mixture was stirred at room temperature for 2 hours. After the reaction mixture was concentrated under reduced pressure, the residue was diluted with 0.01N hydrochloric acid, and extracted with ethyl acetate. The extract was washed with saturated saline solution, and dried over anhydrous sodium sulfate, and the solvent was distilled off under reduced pressure to obtain the title compound (1.24 g, quantitative) as a colorless oil.
NMR (CDCl$_3$) δ: 1.29 (2H, m), 1.91-1.96 (2H, m), 2.90-2.99 (2H, m), 3.30 (2H, t, J=5.7), 3.40 (6H, s), 3.72-3.79 (1H, m), 4.09 (2H, m), 4.35 (1H, t, J=5.1), 4.57-4.61 (2H, m), 5.12 (2H, s), 7.31-7.36 (5H, m).

16b) Benzyl 4-{2-oxo-2,3-dihydro-1H-imidazol-1-yl}piperidin-1-carboxylate

Benzyl 4-({[(2,2-dimethoxyethyl)amino]carbonyl}amino)piperidin-1-carboxylate (0.37 g) obtained in Example 16a) was dissolved in water (5 mL) and methanol (10 mL), and 1N hydrochloric acid (5 mL) was added thereto. The mixture was stirred at room temperature for 3 days. After the reaction mixture was concentrated under reduced pressure, the residue was diluted with water, and extracted with ethyl acetate. The extract was washed with water and saturated saline solution, and dried over anhydrous sodium sulfate, and the solvent was distilled off under reduced pressure to obtain the title compound (0.27 g, 90%) as a colorless solid.
NMR (CDCl$_3$) δ: 1.63 (2H, m), 1.92-1.96 (2H, m), 2.88-2.96 (2H, m), 4.09-4.22 (1H, m), 4.34 (2H, br), 5.14 (2H, s), 6.19 (1H, t, J=2.4), 6.30 (1H, t, J=2.6), 7.26-7.38 (5H, m), 9.66 (1H, br).

16c) 1-(Piperidin-4-yl)-1,3-dihydro-2H-imidazol-2-one

According to the manner similar to that in Example 7c), the title compound (0.14 g, quantitative) was obtained as a colorless solid from the benzyl 4-{2-oxo-2,3-dihydro-1H-imidazol-1-yl}piperidin-1-carboxylate (0.26 g) obtained in Example 16b).
NMR (CDCl$_3$) δ: 2.03-2.07 (2H, m), 2.32-2.46 (4H, m), 2.97-3.07 (2H, m), 3.53-3.57 (2H, m), 4.09-4.17 (1H, m), 6.31 (1H, d, J=3.0), 6.37 (1H, d, J=2.6).

16d) 1-(1-{(2S)-3-[(6-Chloronaphthalen-2-yl)sulfonyl]-2-hydroxypropanoyl}piperidin-4-yl)-1,3-dihydro-2H-imidazol-2-one According to the manner similar to that in Example 1, the title compound (40 mg, 10%) was obtained as a colorless powder from the 1-(piperidin-4-yl)-1,3-dihydro-2H-imidazol-2-one (0.14 g) obtained in Example 16c).
NMR (CDCl$_3$) δ: 1.62-1.78 (2H, m), 2.05-2.34 (4H, m), 2.69-2.85 (1H, m), 3.16-3.30 (1H, m), 3.42-3.56 (2H, m), 4.09-4.14 (1H, m), 4.20-4.28 (1H, m), 4.63-4.70 (1H, m), 5.00-5.06 (1H, m), 6.22 (1H, dd, J=3.0, 12.4), 6.29-6.30 (1H, m), 7.60 (1H, dd, J=1.9, 8.7), 7.95-7.98 (4H, m), 8.51 (1H, s).
Elemental analysis for C$_{21}$H$_{22}$ClN$_3$O$_5$S·0.5H$_2$O
Calcd (%): C, 53.33; H, 4.90; N, 8.88
Found (%): C, 53.56; H, 4.97; N, 8.62

EXAMPLE 17

1-(1-{(2S)-3-[(6-chloronaphthalen-2-yl)sulfonyl]-2-hydroxypropanoyl}piperidin-4-yl)-3-dihydro-2H-benzoimidazol-2-one

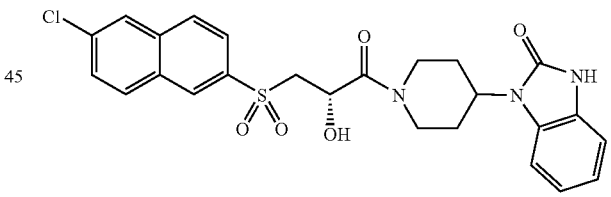

According to the manner similar to that in Example 1, the title compound (0.29 g, 55%) was obtained as a colorless powder from 1-(piperidin-4-yl)-1,3-dihydro-2H-benzoimidazol-2-one (0.22 g).
NMR (CDCl$_3$) δ: 1.93-2.02 (2H, m), 2.38-2.55 (2H, m), 2.76-2.85 (1H, m), 3.21-3.30 (1H, m), 3.48-3.57 (2H, m), 3.87-3.97 (1H, m), 4.11-4.18 (1H, m), 4.55-4.56 (1H, m), 4.75-4.79 (1H, m), 5.10-5.11 (1H, m), 7.05-7.15 (4H, m), 7.58-7.61(1H, m), 7.95-7.98 (4H, m), 8.53 (1H, s), 8.80-8.84 (1H, m).
Elemental analysis for C$_{25}$H$_{24}$ClN$_3$O$_5$S·0.5H$_2$O
Calcd (%): C, 57.41; H, 4.82; N, 8.03
Found (%): C, 57.70; H, 5.04; N, 7.69

EXAMPLE 18

1-(1-{(2S)-3-[(6-Chloronaphthalen-2-yl)sulfonyl]-2-hydroxypropanoyl}piperidin-4-yl)-3-methyl-1,3-dihydro-2H-benzoimidazol-2-one

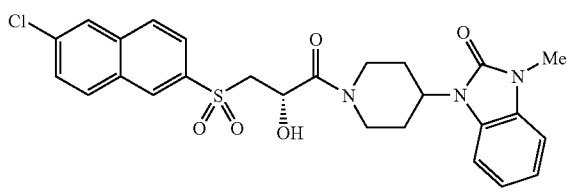

According to the manner similar to that in Example 1, the title compound (95 mg, 18%) was obtained as a colorless powder from 3-methyl-1-(piperidin-4-yl)-1,3-dihydro-2H-benzoimidazol-2-one hydrochloride (0.27 g) and triethylamine (0.10 g).

NMR (CDCl$_3$) δ: 1.89-2.00 (2H, m), 2.32-2.52 (2H, m), 2.76-2.89 (1H, m), 3.21-3.34 (1H, m), 3.42 (3H, s), 3.45-3.55 (2H, m), 3.80-3.88 (1H, m), 4.09-4.16 (1H, m), 4.55-4.64 (1H, m), 4.74-4.77 (1H, m), 5.05-5.10 (1H, m), 6.99-7.12 (4H, m), 7.60(1H, dd, J=1.9, 8.7), 7.95-7.98 (4H, m), 8.53 (1H, s).

Elemental analysis for C$_{26}$H$_{26}$ClN$_3$O$_5$S.0.5H$_2$O
Calcd (%): C, 58.15; H, 5.07; N, 7.82
Found (%): C, 58.21; H, 5.20; N, 7.60

EXAMPLE 19

(2S)-3-[(6-Chloronaphthalen-2-yl)sulfonyl]-1-[4-(1,1-dioxidoisothizolin-2-yl)piperidin-1-yl]-1-oxopropan-2-ol

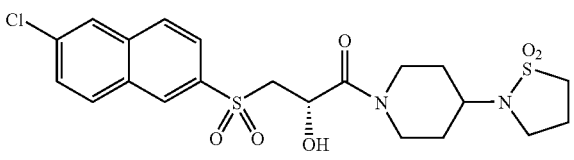

19a) 1-Benzyl-4-(1,1-dioxidoisothiazolin-2-yl)piperidine

According to the manner similar to that in Example 8a), the title compound (4.90 g, 63%) was obtained as a yellow solid from 3-chloropropylsulfonyl chloride (3.5 mL) and 4-amino-1-benzylpiperidine (5.0 g).

NMR (CDCl$_3$) δ: 1.75-1.88 (4H, m), 2.03-2.12 (2H, m), 2.28-2.38 (2H, m), 2.91-2.95 (2H, m), 3.13 (2H, t, J=7.6), 3.28 (2H, t, J=6.6), 3.42-3.49 (1H, m), 3.49 (2H, s), 7.25-7.34 (5H, m).

19b) 4-(1,1-Dioxidoisothiazolin-2-yl)piperidine

According to the manner similar to that in Example 8b), the title compound (3.45 g, quantitative) was obtained as a colorless solid from the 1-benzyl-4-(1,1-dioxidoisothiazolin-2-yl)piperidine (4.90 g) obtained in Example 19a).

NMR (CDCl$_3$) δ: 1.59-1.92 (6H, m), 2.28-2.39 (2H, m), 2.70 (2H, dt, J=2.3, 12.1), 3.11-3.16 (3H, m), 3.30 (2H, t, J=6.8), 3.49-3.60 (1H, m).

19c) (2S)-3-[(6-Chloronaphthalen-2-yl)sulfonyl]-1-[4-(1,1-dioxidoisothiazolin-2-yl)piperidin-1-yl]-1-oxopropan-2-ol According to the manner similar to that in Example 1, the title compound (0.28 g, 51%) was obtained as a colorless powder from the 4-(1,1-dioxidoisothiazolin-2-yl)piperidine (0.23 g) obtained in Example 19b).

NMR (CDCl$_3$) δ: 1.63-1.84 (2H, m), 1.97-2.08 (2H, m), 2.32-2.42 (2H, m), 2.72-2.94 (1H, m), 3.14-3.30 (5H, m), 3.40-3.46 (2H, m), 3.64-3.81 (2H, m), 3.93-4.02 (1H, m), 4.46-4.58 (1H, m), 4.97-5.02 (1H, m), 7.60 (1H, dd, J=2.1, 8.9), 7.94-7.97 (4H, m), 8.51 (1H, s).

Elemental analysis for C$_{21}$H$_{25}$ClN$_2$O$_6$S$_2$
Calcd (%): C, 50.34; H, 5.03; N, 5.59
Found (%): C, 50.02; H, 5.04; N, 5.42

EXAMPLE 20

1-(1-{(2S)-3-[(6-Chloronaphthalen-2-yl)sulfonyl]-2-hydroxypropanoyl}piperidin-4-yl)-3-methyltetrahydropyrimidin-2(1H)-one

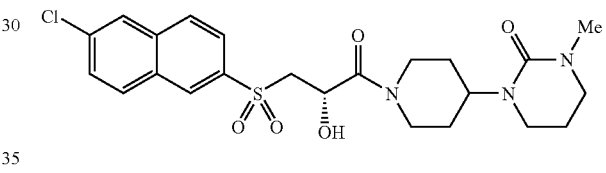

According to the manner similar to that in Example 1, the title compound (60 mg, 32%) was obtained as a colorless powder from 1-methyl-3-(piperidin-4-yl)tetrahydropyrimidin-2(1H)-one (75 mg).

NMR (CDCl$_3$) δ: 1.52-1.84 (4H, m), 1.93-1.96 (2H, m), 2.65-2.79 (1H, m), 2.94 (3H, s), 3.09-3.25 (5H, m), 3.38-3.46 (2H, m), 3.75-3.86 (1H, m), 3.92-3.97 (1H, m), 4.57-4.68 (2H, m), 4.96-5.05 (1H, m), 7.59.(1H, dd, J=2.2, 8.6), 7.94-7.97 (4H, m), 8.51 (1H, s). Elemental analysis for C$_{23}$H$_{28}$ClN$_3$O$_5$S.0.6H$_2$O. Calcd (%): C, 54.72; H, 5.83; N, 8.32. Found (%): C, 54.61; H, 5.82; N, 8.19.

EXAMPLE 21

3-(1-{(2S)-3-[(6-Chloronaphthalen-2-yl)sulfonyl]-2-hydroxypropanoyl}piperidin-4-yl)-1,3-oxazinan-2-one

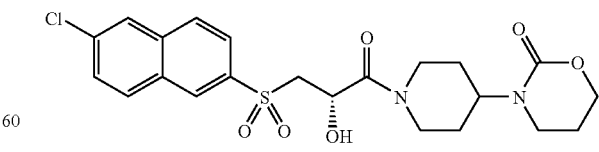

According to the manner similar to that in Example 1, the title compound (0.39 g, 41%) was obtained as a colorless powder from 3-(piperidin-4-yl)-1,3-oxazinan-2-one (0.37 g).

NMR (CDCl$_3$) δ: 1.65-2.08 (6H, m), 2.66-2.80 (1H, m), 3.17-3.25 (3H, m), 3.40-3.48 (2H, m), 3.68-3.84 (1H, m), 4.00-4.04 (1H, m), 4.25 (2H, t, J=5.2), 4.38-4.45 (1H, m), 4.62-4.70 (1H, m), 4.95-5.05 (1H, m), 7.59 (1H, dd, J=2.1, 8.7), 7.94-7.97 (4H, m), 8.51 (1H, s).

Elemental analysis for $C_{22}H_{25}ClN_2O_6S \cdot 0.5H_2O$

Calcd (%): C, 53.93; H, 5.35; N, 5.72

Found (%): C, 54.23; H, 5.36; N, 5.50

EXAMPLE 22

1-(4-{(2S)-3-[(6-Chloronaphthalen-2-yl)sulfonyl]-2-hydroxypropanoyl}piperazin-1-yl)-3-methylpyrrolidin-2-one

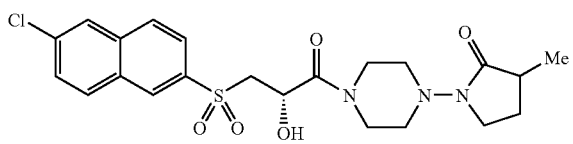

22a) 1-(4-Benzylpiperazin-1-yl)-3-methylpyrrolidin-2-one

A mixture of 3-methyldihydrofuran-2(3H)-one (2.0 g), thionyl chloride (1.5 ml) and zinc chloride (10 mg) was stirred at 80° C. for 15 hours. The mixture was cooled to room temperature, and the reaction mixture was added dropwise to a solution of 4-benzylpiperazin-1-amine (3.8 g) in THF (50 mL) at 0° C., followed by stirring at 0° C. for 2 hours. Sodium hydride (60% in oil; 2.4 g) was added thereto and the mixture was stirred at room temperature for 15 hours. Ice was added thereto, and then the reaction mixture was concentrated under reduced pressure. The residue was diluted with water, and extracted with dichloromethane. The extract was dried over anhydrous sodium sulfate, and the solvent was distilled off under reduced pressure. The residue obtained was purified by basic silica gel column chromatography (ethyl acetate/hexane=1/5) to obtain the title compound (2.0 g, 37%) as a yellow oil.

NMR (CDCl$_3$) δ: 1.18 (3H, d, J=7.2), 1.48-1.63 (1H, m), 2.12-2.29 (1H, m), 2.28-2.49 (1H, m), 2.62 (4H, dd), 2.84-3.08 (4H, m), 3.26-3.47 (2H, m), 3.48-3.64 (2H, m), 7.20-7.40 (5H, m).

22b) 3-Methyl-1-(piperazin-1-yl)pyrrolidin-2-one

According to the manner similar to that in Example 8b), the title compound (1.22 g, 91%) was obtained as a colorless powder from 1-(4-benzylpiperazin-1-yl)-3-methylpyrrolidin-2-one (2.0 g) obtained in Example 22a).

NMR (CDCl$_3$) δ: 1.19 (3H, d, J=7.2 Hz), 1.51-1.68 (1H, m), 1.76-1.93 (1H, m), 2.14-2.29 (1H, m), 2.32-2.48 (1H, m), 2.88-3.08 (8H, m), 3.31-3.48 (2H, m).

22c) 1-(4-1(2S)-3-[(6-Chloronaphthalen-2-yl)sulfonyl]-2-hydroxypropanoyl}piperazin-1-yl)-3-methylpyrrolidin-2-one According to the manner similar to that in Example 1, the title compound (0.25 g, 52%) was obtained as a colorless powder from 3-methyl-1-(piperazin-1-yl)pyrrolidin-2-one (0.18 g) obtained in Example 22b).

NMR (CDCl$_3$) δ: 1.19 (3H, d, J=7.0), 1.58-1.71 (1H, m), 2.15-2.33 (1H, m), 2.33-2.51 (1H, m), 3.00-3.20 (4H, m), 3.31-3.49 (4H, m), 3.58-3.73 (3H, m), 3.72-3.88 (2H, m), 4.92-5.10 (1H, m), 7.59 (1H, dd, J=8.9, 2.1), 7.94-8.00 (4H, m), 8.51 (1H, s).

Elemental analysis for $C_{22}H_{26}ClN_3O_5S \cdot 0.5H_2O$

Calcd (%): C, 54.04; H, 5.57; N, 8.59

Found (%): C, 54.30; H, 5.63; N, 8.37

EXAMPLE 23

1-(4-{(2S)-3-[(6-Chloronaphthalen-2-yl)sulfonyl]-2-hydroxypropanoyl}piperazin-1-yl)-5-methylpyrrolidin-2-one

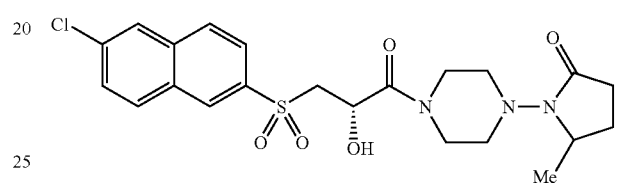

23a) 1-(4-Benzylpiperazin-1-yl)-5-methylpyrrolidin-2-one

According to the manner similar to that in Example 22a), the title compound (2.7 g, 70%) was obtained as a yellow oil from 5-methyldihydrofuran-2(3H)-one (1.6 g).

NMR (CDCl$_3$) δ: 1.23 (3H, d, J=6.2), 1.45-1.63 (1H, m), 2.01-2.38 (3H, m), 2.48 (4H, s), 3.26 (4H, s), 3.51 (2H, s), 3.56-3.70 (1H, m), 7.18-7.40 (5H, m).

23b) 5-Methyl-1-(piperazin-1-yl)pyrrolidin-2-one

According to the manner similar to that in Example 8b), the title compound (1.8 g, 99%) was obtained as a gray solid from 1-(4-benzylpiperazin-1-yl)-5-methylpyrrolidin-2-on (2.7 g) obtained in Example 23a).

NMR (CDCl$_3$) δ: 1.22-1.28 (3H, m), 1.48-1.62 (2H, m), 2.06-2.40 (3H, m), 2.89 (4H, t, J=5.1), 3.12-3.32 (4H, m), 3.57-3.68 (1H, m).

23c) 1-(4-{(2S)-3-[(6-Chloronaphthalen-2-yl)sulfonyl]-2-hydroxypropanoyl}piperazin-1-yl)-5-methylpyrrolidin-2-one According to the manner similar to that in Example 1, the title compound (0.20 g, 42%) was obtained as a colorless powder from 5-methyl-1-(piperazin-1-yl)pyrrolidin-2-one (0.18 g) obtained in Example 23b).

NMR (CDCl$_3$) δ: 1.26 (3H, d, J=6.2), 1.48-1.68 (1H, m), 2.07-2.43 (3H, m), 3.18-3.73 (11H, m), 3.78 (1H, d, J=6.8), 4.91-5.07 (1H, m), 7.58 (1H, dd, J=8.7, 2.1), 7.87-8.00 (4H, m), 8.51 (1H, s).

Elemental analysis for $C_{22}H_{26}ClN_3O_5S$

Calcd (%): C, 55.05; H, 5.46; N, 8.75

Found (%): C, 54.96; H, 5.48; N, 8.68

EXAMPLE 24

1-(4-{(2S)-3-[(6-Chloronaphthalen-2-yl)sulfonyl]-2-hydroxypropanoyl}piperazin-1-yl)-3,3-dimethylpyrrolidin-2-one

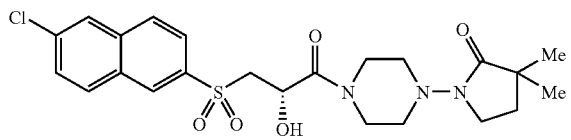

24a) 1-(4-Benzylpiperazin-1-yl)-3,3-dimethylpyrrolidin-2-one

According to the manner similar to that in Example 22a), the title compound (0.68 g, 12%) was obtained as a yellow oil from 3,3-dimethyldihydrofuran-2(3H)-one (2.3 g).

NMR (CDCl$_3$) δ: 1.07-1.26 (6H, m), 1.75-1.98 (2H, m), 2.49-2.68 (4H, m), 2.78-3.06 (4H, m), 3.29-4.32 (4H, m), 7.20-7.37 (5H, m).

24b) 3,3-Dimethyl-1-(piperazin-1-yl)pyrrolidin-2-one

According to the manner similar to that in Example 8b), the title compound (0.48 g, quantitative) was obtained as a colorless powder from 1-(4-benzylpiperazin-1-yl)-3,3-dimethylpyrrolidin-2-one (0.68 g) obtained in Example 24a).

NMR (CDCl$_3$) δ: 1.09-1.26 (6H, m), 1.66-1.99 (3H, m), 2.75-3.05 (8H, m), 3.32-4.31 (2H, m).

24c) 1-(4-{(2S)-3-[(6-Chloronaphthalen-2-yl)sulfonyl]-2-hydroxypropanoyl}piperazin-1-yl)-3,3-dimethylpyrrolidin-2-one According to the manner similar to that in Example 1, the title compound (65 mg, 13%) was obtained as a colorless powder from 3,3-dimethyl-1-(piperazin-1-yl)pyrrolidin-2-one (0.20 g) obtained in Example 24b).

NMR (CDCl$_3$) δ: 1.13 (6H, s), 1.85 (2H, t, J=6.8), 2.98-3.23 (4H, m), 3.26-3.48 (4H, m), 3.55-3.72 (3H, m), 3.73-3.88 (2H, m), 4.90-5.07 (1H, m), 7.59 (1H, dd, J=8.9, 2.1), 7.90-8.04 (4H, m), 8.51 (1H, s).

Elemental analysis for C$_{23}$H$_{28}$ClN$_3$O$_5$S
Calcd (%): C, 55.92; H, 5.71; N, 8.51
Found (%): C, 55.75; H, 5.67; N, 8.22

EXAMPLE 25

1-(4-{(2S)-3-[(6-Chloronaphthalen-2-yl)sulfonyl]-2-hydroxypropanoyl}piperazin-1-yl)tetrahydropyrimidin-2(1H)-one

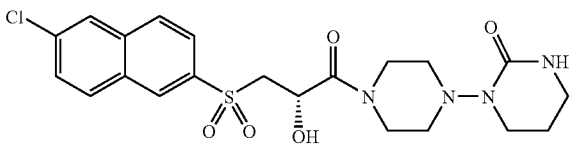

25a) 1-(4-Benzylpiperazin-1-yl)tetrahydropyrimidin-2(1H)-one

A solution of tert-butyl (3-oxopropyl)carbamate (4.2 g) and 4-benzylpiperazin-1-amine (4.6 g) in methanol (60 mL) was heated under reflux for 3 hours, and the solvent was distilled off under reduced pressure. After the residue was dissolved in methanol (60 mL), acetic acid (4.1 mL) and sodium triacetoxyborohydride (3.2 g) were added thereto, and the mixture was stirred at room temperature for 15 hours. The reaction mixture was concentrated under reduced pressure, made alkaline with 1N sodium hydroxide and potassium carbonate, and extracted with dichloromethane. The organic layer was dried over anhydrous sodium sulfate, and the solvent was distilled off under reduced pressure. The residue obtained was dissolved in ethyl acetate (10 mL). and then a 4N hydrochloric acid-ethyl acetate solution (100 ml) was slowly added at 0° C., followed by stirring at room temperature for 5 hours. The precipitate was collected by filtration, dried, and then suspended in acetonitrile (200 mL). DBU (14.6 g) and CDI (7.8 g) were added thereto, and the mixture was heated under reflux for 15 hours. The reaction mixture was concentrated under reduced pressure, and the residue was diluted with an aqueous sodium bicarbonate solution and extracted with dichloromethane. The extract was dried over anhydrous sodium sulfate, and the solvent was distilled off under reduced pressure. The residue was purified by basic silica gel column chromatography (ethyl acetate), and recrystallized from diethyl ether to obtain the title compound (3.1 g, 46%) as white crystals.

NMR (CDCl$_3$) δ: 1.92-1.98 (2H, m), 2.55 (4H, br), 3.10-3.20 (6H, m), 3.40 (2H, t, J=6.1), 3.52 (2H, s), 4.48 (1H, br), 7.22-7.34 (5H, m).

25b) 1-(Piperazin-1-yl)tetrahydropyrimidin-2(1H)-one

To a solution of 1-(4-benzylpiperazin-1-yl)tetrahydropyrimidin-2(1H)-one obtained in Example 25a) (0.82 g) was added 20% palladium hydroxide on carbon (containing 50% water; 0.20 g), and the mixture was stirred at room temperature for 60 hours under a hydrogen atmosphere. The reaction mixture was filtered, and the solvent was distilled off under reduced pressure to obtain the title compound (0.56 g, quantitative) as colorless crystals.

NMR (CDCl$_3$) δ: 1.65 (2H, br), 1.91-1.99 (2H, m), 2.92-3.22 (9H, m), 3.41 (2H, t, J=5.8), 4.51 (1H, br).

25c) 1-(4-{(2S)-3-[(6-Chloronaphthalen-2-yl)sulfonyl]-2-hydroxypropanoyl}piperazin-1-yl)tetrahydropyrimidin-2(1H)-one 1-(Piperazin-1-yl)tetrahydropyrimidin-2(1H)-one obtained in Example 25b) (0.55 g), (2S)-3-[(6-chloronaphthalen-2-yl)sulfony]-2-hydroxypropionic acid (0.94 g) and HOBt (0.46 g) were dissolved in DMF (20 mL), WSC was added thereto, and the mixture was stirred at room temperature for 15 hours. The reaction mixture was concentrated under reduced pressure, and the residue was washed with an aqueous sodium bicarbonate solution, and extracted with dichloromethane. The extract was dried over sodium sulfate, and the solvent was distilled off under reduced pressure. The residue was purified by basic silica gel column chromatography (ethyl acetate to ethyl acetate/methanol=5/1), and recrystallized from ethyl acetate-methanol to obtain the title compound (0.88 g, 61%) as a colorless powder.

NMR (CDCl$_3$) δ: 1.93-2.01 (2H, m), 3.18-3.23 (4H, m), 3.41-3.49 (10H, m), 3.91 (1H, d, J=6.8), 4.55 (1H, br), 4.96-5.02 (1H, m), 7.58 (1H, dd, J=8.7, 1.9), 7.93-7.97 (4H, m), 8.51 (1H, s).
Elemental analysis for C$_{21}$H$_{25}$ClN$_4$O$_5$S
Calcd (%): C, 52.44; H, 5.24; N, 11.65
Found (%): C, 52.31; H, 5.30; N, 11.40

EXAMPLE 26

1-(4-{(2S)-3-[(6-Chloronaphthalen-2-yl)sulfonyl]-2-hydroxypropanoyl}piperazin-1-yl)imidazolidin-2-one

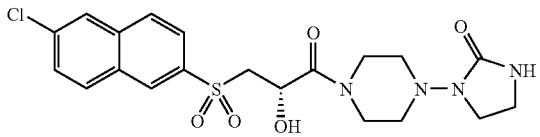

26a) 1-(4-Benzylpiperazin-1-yl)imidazolidin-2-one

According to the manner similar to that in Example 25a), the title compound (1.3 g, 80%) was obtained as a light brown powder from tert-butyl (2-oxoethyl)carbamate (1.1 g).
NMR (CDCl$_3$) δ: 2.62 (4H, s), 2.86-3.01 (4H, m), 3.29-3.43 (2H, m), 3.44-3.53 (2H, m), 3.53 (2H, s), 4.48 (1H, s), 7.19-7.38 (5H, m).

26b) 1-(Piperazin-1-yl)imidazolidin-2-one

According to the manner similar to that in Example 8b), the title compound (0.85 g, quantitative) was obtained as a gray oil from 1-(4-benzylpiperazin-1-yl)imidazolidin-2-one (1.3 g) obtained in Example 26a).
NMR (CDCl$_3$) δ: 2.82-2.95 (4H, m), 2.95-3.08 (4H, m), 3.30-3.56 (5H, m), 4.80 (1H, s).

26c) 1-(4-{(2S)-3-[(6-Chloronaphthalen-2-yl)sulfonyl]-2-hydroxypropanoyl}piperazin-1-yl)imidazolidin-2-one According to the manner similar to that in Example 1, the title compound (0.37 g, 27%) was obtained as a colorless powder from 1-(piperazin-1-yl)imidazolidin-2-one (0.51 g) obtained in Example 26b).
NMR (CDCl$_3$) δ: 2.22-2.36 (1H, m), 2.87-3.10 (4H, m), 3.30-3.92 (11H, m), 4.99 (1H, dd, J=6.7, 4.4), 7.59 (1H, dd, J=8.9, 2.1), 7.87-8.07 (4H, m), 8.51 (1H, s).
Elemental analysis for C$_{20}$H$_{23}$ClN$_4$O$_5$S
Calcd (%): C, 51.44; H, 4.96; N, 12.00
Found (%): C, 51.55; H, 4.92; N, 11.90

EXAMPLE 27

3-(4-{(2S)-3-[(6-Chloronaphthalen-2-yl)sulfonyl]-2-hydroxypropanoyl}piperazin-1-yl)-1,3-oxazolidin-2-one

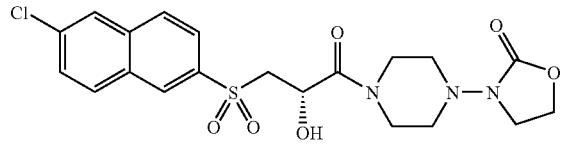

27a) 3-(4-Benzylpiperazin-1-yl)-1,3-oxazolidin-2-one

According to the manner similar to that in Example 25a), the title compound (1.6 g, 88%) was obtained as a yellow oil from hydroxyacetaldehyde (0.42 g).
NMR (CDCl$_3$) δ: 2.63 (4H, d, J=4.1), 2.93-3.06 (4H, m), 3.53 (2H, s), 3.58-3.72 (2H, m), 4.27-4.38 (2H, m), 7.19-7.39 (5H, m).

27b) 3-(Piperazin-1-yl)-1,3-oxazolidin-2-one

According to the manner similar to that in Example 8b), the title compound (1.1 g, quantitative) was obtained as a colorless oil from 3-(4-benzylpiperazin-1-yl)-1,3-oxazolidin-2-one (1.6 g) obtained in Example 27a).
NMR (CDCl$_3$) δ: 2.91-3.04 (8H, m), 3.30-3.45 (1H, m), 3.60-3.69 (2H, m), 4.28-4.38 (2H, m).

27c) 3-(4-{(2S)-3-[(6-Chloronaphthalen-2-yl)sulfonyl]-2-hydroxypropanoyl}piperazin-1-yl)-1,3-oxazolidin-2-one According to the manner similar to that in Example 1, the title compound (0.56 g, 60%) was obtained as a colorless powder from 3-(piperazin-1-yl)-1,3-oxazolidin-2-one (0.34 g) obtained in Example 27b).
NMR (CDCl$_3$) δ: 3.01-3.18 (4H, m), 3.39-3.48 (2H, m), 3.59-3.89 (7H, m), 4.29-4.42 (2H, m), 4.93-5.08 (1H, m), 7.59 (1H, dd, J=8.7, 2.1), 7.87-8.00 (4H, m), 8.51 (1H, s).
Elemental analysis for C$_{20}$H$_{22}$ClN$_3$O$_6$S
Calcd (%): C, 51.34; H, 4.74; N, 8.98
Found (%): C, 51.31; H, 4.78; N, 8.90

EXAMPLE 28

1-(4-{(2S)-3-[(6-Chloronaphthalen-2-yl)sulfonyl]-2-hydroxypropanoyl}piperazin-1-yl)-3-methylimidazolidin-2-one

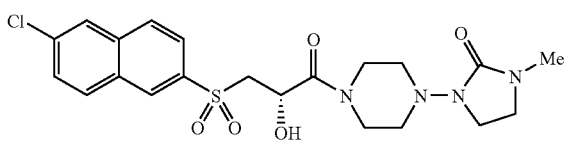

28a) 1-(4-Benzylpiperazin-1-yl)-3-methylimidazolidin-2-one

According to the manner similar to that in Example 13a), the title compound (0.17 g, 41%) was obtained as a colorless powder from 1-(4-benzylpiperazin-1-yl)imidazolidin-2-one (0.39 g) obtained in Example 26a).

NMR (CDCl$_3$) δ: 2.52-2.66 (4H, m), 2.76 (3H, s), 2.92-3.03 (4H, m), 3.17-3.30 (2H, m), 3.31-3.41 (2H, m), 3.53 (2H, s), 7.23-7.38 (5H, m).

28b) 1-Methyl-3-(piperazin-1-yl)imidazolidin-2-one

According to the manner similar to that in Example 8b), the title compound (0.12 g, quantitative) was obtained as a gray solid from 1-(4-benzylpiperazin-1-yl)-3-methylimidazolidin-2-one (0.17 g) obtained in Example 28a).

NMR (CDCl$_3$) δ: 2.56-2.65 (1H, m), 2.77 (3H, s), 2.99 (8H, s), 3.18-3.31 (2H, m), 3.33-3.43 (2H, m).

28c) 1-(4-{(2S)-3-[(6-Chloronaphthalen-2-yl)sulfonyl]-2-hydroxypropanoyl}piperazin-1-yl)-3-methylimidazolidin-2-one According to the manner similar to that in Example 1, the title compound (0.14 g, 46%) was obtained as a colorless powder from 1-methyl-3-(piperazin-1-yl)imidazolidin-2-one (0.11 g) obtained in Example 28b).

NMR (CDCl$_3$) δ: 2.77 (3H, s), 2.91-3.17 (4H, m), 3.19-3.49 (6H, m), 3.53-3.87 (5H, m), 4.99 (1H, dd, J=7.1, 3.5), 7.58 (1H, dd, J=8.9, 2.1), 7.85-8.04 (4H, m), 8.51 (1H, s).

Elemental analysis for $C_{21}H_{25}ClN_4O_5S \cdot 0.2H_2O$

Calcd (%): C, 52.05; H, 5.28; N, 11.56
Found (%): C, 52.18; H, 5.44; N, 11.29

EXAMPLE 29

2-(1-{(2S)-3-[(6-Chloronaphthalen-2-yl)sulfonyl]-2-hydroxypropanoyl}piperidin-4-yl)tetrahydropyridazin-3(2H)-one

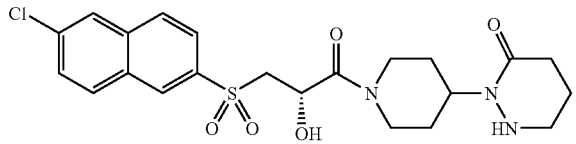

29a) tert-Butyl 2-{1-[(benzyloxy)carbonyl]piperidin-4-yl}-3-oxotetrahydropyridazin-1(2H)-carboxylate According to the manner similar to that in Example 8a), the title compound (1.3 g, quantitative) was obtained as a yellow oil from benzyl 4-[2-(tert-butoxycarbonyl)hydrazino]piperidin-1-carboxylate (1.1 g) and 4-bromobutyryl chloride (0.35 g).

NMR (CDCl$_3$) δ: 1.47 (9H, s), 1.54-2.51 (8H, m), 2.75-3.04 (3H, m), 4.09-4.54 (4H, m), 5.06-5.18 (2H, m), 7.28-7.44 (5H, m).

29b) 2-(Piperidin-4-yl)tetrahydropyridazin-3(2H)-one tert-Butyl 2-{1-[(benzyloxy)carbonyl]piperidin-4-yl}-3-oxotetrahydropyridazin-1(2H)-carboxylate (0.84 g) obtained in Example 29a} was dissolved in trifluoroacetic acid (1 mL) and dichloromethane (1.5 mL), and the mixture was stirred at room temperature for 2 hours. The reaction mixture was concentrated under reduced pressure, and the residue was made alkaline with an aqueous sodium bicarbonate solution and then extracted with dichloromethane. The extract was dried over anhydrous sodium sulfate, and the solvent was distilled off under reduced pressure. The residue was dissolved in ethanol (10 mL), and 10% palladium on carbon (0.1 g) was added, followed by stirring under a hydrogen atmosphere for 15 hours. After the catalyst was removed, the solvent was distilled off under reduced pressure to obtain the title compound (0.40 g, quantitative) as a yellow oil.

NMR (CDCl$_3$) δ: 1.53-2.56 (13H, m), 2.57-2.78 (1H, m), 2.89-3.25 (2H, m), 4.18-4.50 (1H, m).

29c) 2-(1-{(2S)-3-[(6-Chloronaphthalen-2-yl)sulfonyl]-2-hydroxypropanoyl}piperidin-4-yl)tetrahydropyridazin-3(2H)-one According to the manner similar to that in Example 1, the title compound (0.09 g, 9%) was obtained as a colorless powder from 2-(piperidin-4-yl)tetrahydropyridazin-3(2H)-one (0.37 g) obtained in Example 29b).

NMR (CDCl$_3$) δ: 1.63-2.07 (6H, m), 2.42-3.24 (6H, m), 3.26-4.04 (5H, m), 4.50-4.76 (2H, m), 5.01 (1H, s), 7.59 (1H, dd, J=8.8, 2.0), 7.86-8.05 (4H, m), 8.52 (1H, d, J=3.0).

Elemental analysis for $C_{22}H_{26}ClN_3O_5S$

Calcd (%): C, 55.05; H, 5.46; N, 8.75
Found (%): C, 54.91; H, 5.28; N, 8.45

EXAMPLE 30

1-(4-{(2S)-3-[(6-Chloronaphthalen-2-yl)sulfonyl]-2-hydroxypropanoyl}piperazin-1-yl)-3-methyltetrahydropyrimidin-2(1H)-one

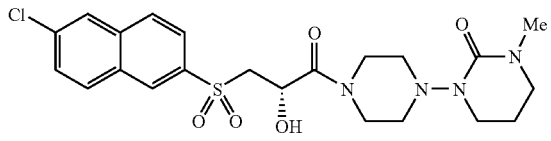

30a) 1-(4-Benzylpiperazin-1-yl)-3-methyltetrahydropyrimidin-2(1H)-one

Lithium bis(trimethylsilyl)amide (1M THF solution; 1.5 mL) was added to a solution of 1-(4-benzylpiperazin-1-yl)tetrahydropyrimidin-2(1H)-one (0.27 g) obtained in Example 25a) in THF (10 mL) at 0° C., and the mixture was stirred at room temperature for one hour. Methyl iodide (0.09 mL) was added thereto, and the mixture was stirred at room temperature for 15 hours. The reaction mixture was concentrated under reduced pressure, and the residue was diluted with an aqueous sodium bicarbonate solution, and extracted with dichloromethane. The extract was dried over anhydrous sodium sulfate, and the solvent was distilled off under reduced pressure to obtain the title compound (0.30 g, quantitative) as a brown oil.

NMR (CDCl$_3$) δ: 1.83-2.05 (3H, m), 2.52 (4H, s), 2.90 (2H, s), 3.04-3.23 (4H, m), 3.33-3.46 (3H, m), 3.51 (3H, s), 7.21-7.40 (5H, m).

30b) 1-Methyl-3-(piperazin-1-yl)tetrahydropyrimidin-2(1H)-one

According to the manner similar to that in Example 8b), the title compound (0.20 g, quantitative) was obtained as a light brown solid from 1-(4-benzylpiperazin-1-yl)-3-methyltetrahydropyrimidin-2(1H)-one (0.29 g) obtained in Example 30a).

NMR (CDCl$_3$) δ: 1.87-2.05 (2H, m), 2.16-2.32 (2H, m), 2.53 (1H, s), 2.90 (6H, s), 3.06-3.23 (4H, m), 3.33-3.46 (3H, m).

30c) 1-(4-{(2S)-3-[(6-Chloronaphthalen-2-yl)sulfonyl]-2-hydroxypropanoyl}piperazin-1-yl)-3-methyltetrahydropyrimidin-2(1H)-one According to the manner similar to that in Example 1, the title compound (0.28 g, 56%) was obtained as a yellow powder from 1-methyl-3-(piperazin-1-yl)tetrahydropyrimidin-2(1H)-one (0.20 g) obtained in Example 30b).

NMR (CDCl$_3$) δ: 1.89-2.05 (3H, m), 2.89 (3H, s), 3.09-3.23 (5H, m), 3.30-3.51 (7H, m), 3.83 (2H, d, J=6.8), 4.88-5.06 (1H, m), 7.58 (1H, dd, J=8.9, 2.1), 7.88-8.02 (4H, m), 8.51 (1H, d, J=0.8).

Elemental analysis for $C_{22}H_{27}ClN_4O_5S \cdot 0.5H_2O$
Calcd (%): C, 52.43; H, 5.60; N, 11.12
Found (%): C, 52.78; H, 5.86; N, 11.04

EXAMPLE 31

1-(1-{(2S)-3-[(6-Chloronaphthalen-2-yl)sulfonyl]-2-hydroxypropanoyl}piperidin-4-yl)-4-methyltetrahydropyrimidin-2(1H)-one

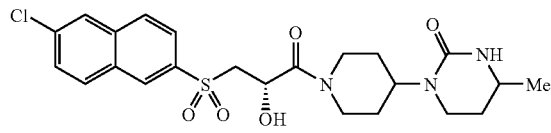

31a) Benzyl 4-(4-methyl-2-oxotetrahydropyrimidin-1(2H)-yl)piperidin-1-carboxylate A solution of benzyl 4-isocyanatopiperidin-1-carboxylate (0.26 g) in acetonitrile (10 mL) was added to a solution of 4-bromobutan-2-amine hydrobromide (0.17 g) and triethylamine (0.10 g) in acetonitrile (10 mL), followed by stirring at room temperature for one hour. Potassium tert-butoxide (0.29 g) and THF (20 mL) were added thereto, and the mixture was further stirred at room temperature for 15 hours. The reaction mixture was concentrated under reduced pressure, and the residue was diluted with water, and extracted with ethyl acetate. The extract was washed with water and saturated saline solution and dried over anhydrous sodium sulfate, and the solvent was distilled off under reduced pressure. The residue was purified by silica gel column chromatography (ethyl acetate to ethyl acetate/methanol=10/1) to obtain the title compound (0.15 g, 45%) as a light brown solid.

NMR (CDCl$_3$) δ: 1.17 (3H, d, J=6.2), 1.42-1.73 (5H, m), 1.91 (1H, dd, J=4.0, 1.1), 2.86 (2H, d, J=5.3), 3.00-3.25 (2H, m), 3.48 (1H, s), 4.27 (2H, s), 4.37-4.58 (2H, m), 5.12 (2H, s), 7.29-7.42 (5H, m).

31b) 4-Methyl-1-(piperidino-4-yl)tetrahydropyrimidin-2(1H)-one

According to the manner similar to that in Example 7c), the title compound (88 mg, quantitative) was obtained as a colorless solid from benzyl 4-(4-methyl-2-oxotetrahydropyrimidin-1(2H)-yl)piperidin-1-carboxylate (0.15 g) obtained in Example 31a).

NMR (CDCl$_3$) δ: 1.16 (3H, d, J=6.4), 1.41-1.74 (6H, m), 1.87-2.02 (1H, m), 2.64-2.83 (2H, m), 3.04-3.19 (3H, m), 3.20-3.33 (1H, m), 3.37-3.56 (1H, m), 4.27-4.48 (2H, m).

31c) 1-(1-{(2S)-3-[(6-Chloronaphthalen-2-yl)sulfonyl]-2-hydroxypropanoyl}piperidin-4-yl)-4-methyltetrahydropyrimidin-2(1H)-one According to the manner similar to that in Example 1, the title compound (123 mg, 58%) was obtained as a light brown powder from 4-methyl-1-(piperidino-4-yl)tetrahydropyrimidin-2(1H)-one (85 mg) obtained in Example 31b).

NMR (CDCl$_3$) δ: 1.15-1.23 (3H, m), 1.43-2.01 (5H, m), 2.72 (1H, s), 3.00-3.31 (3H, m), 3.33-3.61 (3H, m), 3.68-4.03 (2H, m), 4.39-4.71 (3H, m), 5.02 (1H, d, J=4.7), 7.59 (1H, dd, J=8.7, 2.1), 7.86-8.06 (4H, m), 8.51 (1H, s).

Elemental analysis for $C_{23}H_{28}ClN_3O_5S$
Calcd (%): C, 55.92; H, 5.71; N, 8.51
Found (%): C, 55.74; H, 5.87; N, 8.69

EXAMPLE 32

1-(1-{3-[(6-chloronaphthalen-2-yl)sulfonyl]propanoyl}piperidin-4-yl)tetrahydropyrimidin-2(1H)-one

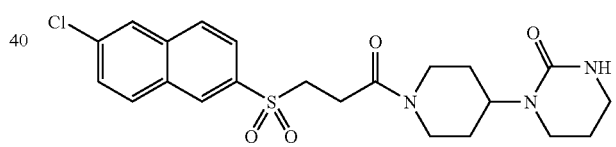

1-(Piperidin-4-yl)tetrahydropyrimidin-2(1H)-one (0.18 g), 3-((6-chlorohaphtalen-2-yl)sulfonyl)propionic acid (0.30 g), HOBt (0.23 g) and triethylamine (0.42 mL) were dissolved in DMF (10 mL), WSC (0.29 g) was added thereto, and the mixture was stirred at room temperature for 15 hours. The reaction mixture was concentrated under reduced pressure, and the residue was diluted with an aqueous sodium bicarbonate solution, and extracted with dichloromethane. The extract was dried over sodium sulfate, and the solvent was distilled off under reduced pressure. The residue was purified by basic silica gel chromatography (ethyl acetate to ethyl acetate/methanol=10/1) to obtain the title compound (0.35 g, 76%) as a colorless powder.

NMR (CDCl$_3$) δ: 1.41-1.80 (4H, m), 1.83-2.00 (2H, m), 2.49-2.67 (1H, m), 2.76-2.97 (2H, m), 3.04-3.19 (3H, m), 3.22-3.35 (2H, m), 3.42-3.66 (2H, m), 3.80-3.96 (1H, m), 4.45-4.71 (3H, m), 7.60 (1H, dd, J=8.9, 1.9), 7.84-8.02 (4H, m), 8.48 (1H, s).

Elemental analysis for $C_{22}H_{26}ClN_3O_4S$
Calcd (%): C, 56.95; H, 5.65; N, 9.06
Found (%): C, 56.65; H, 5.61; N, 9.00

EXAMPLE 33

1-(1-{3-[(6-Chloronaphthalen-2-yl)sulfonyl]
propanoyl}piperazin-4-yl)tetrahydropyrimidin-2
(1H)-one

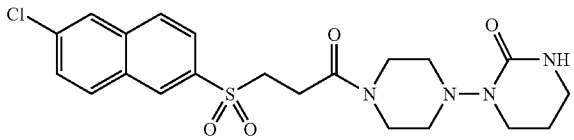

1-(Piperazin-4-yl)tetrahydropyrimidin-2(1H)-one (0.37 g), 3-((6-chlorohaphtalen-2-yl)sulfonyl)propionic acid (0.60 g), HOBt (0.46 g) and triethylamine (0.61 mL) were dissolved in DMF (10 mL), WSC (0.58 g) was added thereto, and the mixture was stirred at room temperature for 15 hours. The reaction mixture was concentrated under reduced pressure, and the residue was diluted with an aqueous sodium bicarbonate solution, and extracted with dichloromethane. The extract was dried over sodium sulfate, and the solvent was distilled off under reduced pressure. The residue was purified by basic silica gel chromatography (from ethyl acetate to ethyl acetate/methanol=10/1), and recrystallized from ethyl acetate-methanol to obtain the title compound (0.83 g, 89%) as a light brown powder.

NMR (CDCl$_3$) δ: 1.88-2.01 (2H, m), 2.75-3.64 (16H, m), 4.46 (1H, s), 7.59 (1H, dd, J=8.7, 2.1), 7.84-8.01 (4H, m), 8.47 (1H, d, J=0.9).

Elemental analysis for $C_{21}H_{25}ClN_4O_4S \cdot 0.5H_2O$

Calcd (%): C, 53.21; H, 5.53; N, 11.82

Found (%): C, 53.52; H, 5.78; N, 11.52

EXAMPLE 34

Ethyl [3-(1-{(2S)-3-[(6-chloronaphthalen-2-yl)sulfonyl]-2-hydroxypropanoyl}piperidin-4-yl)-2-oxotetrahydropyrimidin-1(2H)-yl]acetate

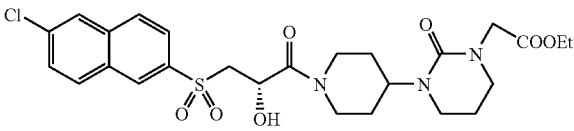

34a) Benzyl 4-[3-(ethoxycarbonylmethyl)-2-oxotetrahydropyrimidin-1(2H)-yl]piperidin-1-carboxylate Lithium bis(trimethylsilyl)amide (1.1M THF solution (3.63 mL)) was added dropwise to a solution of benzyl 4-(2-oxotetrahydropyrimidin-1(2H)-yl)piperidino-1-carboxylate (1.2 g) in DMF (50 mL) under ice-cooling, and the mixture was stirred for 40 minutes. Ethyl bromoacetate (0.55 mL) was added to the mixture under ice-cooling, and the reaction mixture was stirred at room temperature overnight. The reaction solution was diluted with an aqueous saturated ammonium solution, and the solvent was concentrated under reduced pressure. The residue was diluted with ethyl acetate and THF, washed with saturated saline solution and dried on anhydrous sodium sulfate, and the solution was concentrated under reduced pressure. The residue was purified by silica gel column chromatography (ethyl acetate/hexane=1/4 to 1/1) to obtain the title compound (0.3 g, 19%) as a yellow oil.

NMR (CDCl$_3$) δ: 1.27 (3H, t, J=6.9), 1.47-1.67 (4H, m), 1.93-2.01 (2H, m), 2.80-2.93 (2H, m), 3.17 (2H, t, J=6.0), 3.31 (2H, t, J=6.0), 4.05 (2H, s), 4.17 (2H, q, J=6.9), 4.20-4.32 (2H, m), 4.44-4.54 (1H, m), 5.11 (2H, s), 7.28-7.39 (5H, m).

34b) Ethyl [2-oxo-3-(piperidin-4-yl)tetrahydropyrimidin-1(2H)-yl-acetate

Benzyl 4-[3-(ethoxycarbonylmethyl)-2-oxotetrahydropyrimidin-1(2H)-yl]piperidinyl-carboxylate (0.30 g) obtained in Example 34a) and 10% palladium on carbon (60 mg) were suspended in methanol (20 mL), followed by stirring at room temperature for 8 hours under a hydrogen atmosphere. The reaction mixture was filtered and the filtrate was concentrated under reduced pressure to obtain the title compound (180 mg, 90%) as a yellow oil.

NMR (CDCl$_3$) δ: 1.27 (3H, t, J=7.2), 1.55-1.85 (4H, m), 1.95-2.10 (2H, m), 2.65-2.81 (2H, m), 3.15-3.26 (4H, m), 3.32 (2H, t, J=6.0), 4.07 (2H, s), 4.18 (2H, q, J=7.2), 4.40-4.55 (1H, m).

34c) Ethyl [3-(1-{(2S)-3-[(6-chloronaphthalen-2-yl)sulfonyl]-2-hydroxypropanoyl}piperidin-4-yl)-2-oxotetrahydropyrimidin-1(2H)-yl]acetate According to the manner similar to that in Example 1, the title compound (70 mg, 18%) was obtained as a white powder from ethyl [2-oxo-3-(piperidin-4-yl)tetrahydropyrimidin-1(2H)-yl]acetate (0.1 g) obtained in Example 34b).

NMR (CDCl$_3$) δ: 1.28 (3H, t, J=7.2), 1.46-1.79 (4H, m), 1.95-2.05 (2H, m), 2.61-2.81 (1H, m), 3.16-3.25 (2H, m), 3.30-3.47 (5H, m), 3.73-3.98 (2H, m), 4.06 (2H, s), 4.19 (2H, t, J=7.2), 4.50-4.70 (2H, m), 4.95-5.06 (1H, m), 7.59 (1H, dd, J=8.8, 2.2), 7.94 (3H, s), 7.96 (1H, d, J=8.8), 8.51 (1H, s).

Elemental analysis for $C_{26}H_{32}N_3O_7SCl \cdot 0.7CH_2Cl_2$

Calcd (%): C, 51.27; H, 5.38; N, 6.72

Found (%): C, 51.42; H, 5.41; N, 6.70

EXAMPLE 35 tert-Butyl [3-(1-{(2S)-3-[(6-chloronaphthalen-2-yl)sulfonyl]-2-hydroxypropanoyl}piperidin-4-yl)-2-oxotetrahydropyrimidin-1(2H)-yl]acetate

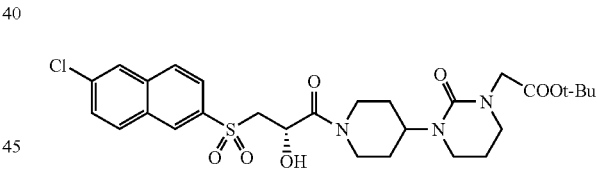

35a) Benzyl 4-[3-(tert-butoxycarbonylmethyl)-2-oxotetrahydropyrimidin-1(2H)-yl]piperidin-1-carboxylate According to the manner similar to that in Example 34a), the title compound (7.0 g, 76%) was obtained as a white powder from benzyl 4-(2-oxotetrahydropyrimidin-1(2H)-yl) piperidin-1-carboxylate (6.8 g) and tert-butyl bromoacetate (4.17 g).

NMR (CDCl$_3$) δ: 1.46 (9H, s), 1.48-1.80 (4H, m), 1.90-2.05 (2H, m), 2.78-2.92 (2H, m), 3.16 (2H, t, J=5.6), 3.29 (2H, t, J=5.8), 3.97 (2H, s), 4.14-4.29 (2H, m), 4.27-4.59 (1H, m), 5.12 (2H, s), 7.30-7.42 (5H, m).

35b) tert-Butyl [2-oxo-3-(piperidin-4-yl)tetrahydropyrimidin-1(2H)-yl]acetate According to the manner similar to that in Example 34b), the title compound (0.30 g, quantitative) was obtained as a white powder from benzyl 4-[3-(tert-butoxycarbonylmethyl)-2-oxotetrahydropyrimidin-1(2H)-yl]piperidin-1-carboxylate (0.45 g) obtained in Example 35a).

NMR (CDCl$_3$) δ: 1.46 (9H, s), 1.80-1.98 (4H, m), 2.10-2.25 (2H, m), 2.93 (2H, t, J=11.1), 3.24-3.30 (4H, m), 3.48-3.57 (2H, m), 3.96 (2H, s), 4.58-4.66 (1H, m).

35c) tert-Butyl [3-(1-{(2S)-3-[(6-chloronaphthalen-2-yl)sulfonyl]-2-hydroxypropanoyl}piperidin-4-yl)-2-oxotetrahydropyrimidin-1(2H)-yl]acetate According to the manner similar to that in Example 1, the title compound (0.38 g, 57%) was obtained as a white powder from tert-butyl [2-oxo-3-(piperidin-4-yl)tetrahydropyrimidin-1(2H)-yl]acetate (0.35 g) obtained in Example 35b).

NMR (CDCl$_3$) δ: 1.47 (9H, s), 1.53-1.82 (4H, m), 1.94-2.03 (2H, m), 2.64-2.78 (1H, m), 3.09-3.21 (3H, m), 3.28-3.47 (4H, m), 3.76-2.97 (4H, m), 4.52-4.68 (2H, m), 4.93-5.04 (1H, m), 7.58 (1H, dd, J=9.0, 2.1), 7.94 (3H, s), 7.96 (1H, d, J=9.0), 8.51 (1H, s).

Elemental analysis for C$_{28}$H$_{36}$N$_3$O$_7$SCl.0.2H$_2$O
Calcd (%): C, 56.26; H, 6.14; N, 7.03
Found (%): C, 51.27; H, 5.22; N, 6.87

EXAMPLE 36

2-[3-(1-{(2S)-3-[(6-Chloronaphthalen-2-yl)sulfonyl]-2-hydroxypropanoyl}piperidin-4-yl)-2-oxotetrahydropyrimidin-1(2H)-yl]acetamide

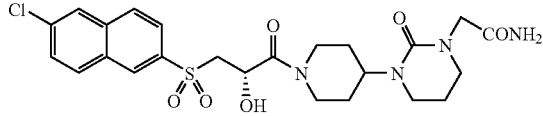

36a) [3-{1-[(Benzyloxy)carbonyl]piperidin-4-yl}-2-oxotetrahydropyrimidin-1(2H)-yl]acetic acid An aqueous 4N sodium hydroxide solution (10 mL) was added to a solution of benzyl 4-[3-(tert-butoxycarbonylmethyl)-2-oxotetrahydropyrimidin-1(2H)-yl]piperidin-1-carboxylate (1.7 g) obtained in Example 35a) in ethanol (20 mL), and the mixture was stirred at room temperature overnight. Ethanol was distilled off under reduced pressure, and 1N hydrochloric acid was added to the residue to adjust pH to 3, followed by extraction with chloroform. The extract was dried over anhydrous magnesium sulfate, and concentrated under reduced pressure to obtain the title compound (1.5 g, quantitative) as a white powder.

NMR (CDCl$_3$) δ: 1.45-1.70 (4H, m), 1.93-2.01 (2H, m), 2.75-2.90 (2H, m), 3.17 (2H, t, J=5.7), 3.34 (2H, t, J=5.7), 4.02 (2H, s), 4.20-4.35 (2H, m), 4.43-4.45 (1H, m), 5.12 (2H, s), 7.28-7.40 (5H, m).

36b) Benzyl 4-[3-(carbamoylmethyl)-2-oxotetrahydropyrimidin-1(2H)-yl]piperidino-1-carboxylate WSC (0.39 g) was added to a solution of [3-{1-[(benzyloxy)carbonyl]piperidin-4-yl}-2-oxotetrahydropyrimidin-1(2H)-yl]acetic acid (0.70 g) obtained in Example 36a) and HOBt-NH$_3$ (0.31 g) in THF/dichloromethane (1/1, 30 mL), and the mixture was stirred at room temperature for overnight. The solvent was distilled off under reduced pressure, and the residue was diluted with chloroform. The reaction mixture was washed with an aqueous saturated sodium bicarbonate solution, dried over anhydrous magnesium sulfate, and concentrated under reduced pressure. The white solid obtained was washed with ethyl acetate to obtain the title compound (0.70 g, quantitative) as a white powder.

NMR (CDCl$_3$) δ: 1.53-1.70 (4H, m), 1.93-2.02 (2H, m), 2.78-2.93 (2H, m), 3.17 (2H, t, J=5.8), 3.35 (2H, t, J=6.0), 3.93 (2H, s), 4.20-4.36 (2H, m), 4.40-4.56 (1H, m), 5.12 (2H, s), 5.58 (1H, brs), 6.52 (1H, brs), 7.27-7.38 (5H, m).

36c) 2-(2-Oxo-3-piperidin-4-yl) tetrahydropyrimidin-1(2H)-yl]acetamide

According to the manner similar to that in Example 34b), the title compound (0.30 g, 67%) was obtained as a white powder from benzyl 4-[3-(carbamoylmethyl)-2-oxotetrahydropyrimidin-1(2H)-yl]piperidin-1-carboxylate (0.70 g) obtained in Example 36b).

NMR (DMSO-d$_6$) δ: 1.40-1.58 (4H, m), 1.81-1.89 (2H, m), 2.46-2.54 (2H, m), 2.99 (2H, d, J=12.0), 3.11 (2H, t, J=6.0), 3.20 (2H, t, J=6.0), 3.77 (2H, s), 4.10-4.21 (1H, m), 6.93 (1H, brs), 7.19 (1H, brs).

36d) 2-[3-(1-{(2S)-3-[(6-Chloronaphthalen-2-yl) sulfonyl]-2-hydroxypropanoyl}piperidin-4-yl)-2-oxotetrahydropyrimidin-1(2H)-yl]acetamide According to the manner similar to that in Example 1, the title compound (0.21 g, 28%) was obtained as a white powder from 2-[2-oxo-3-(piperidin-4-yl)tetrahydropyrimidin-1 (2H)-yl]acetamide (0.30 g) was obtained in Example 36c).

NMR (CDCl$_3$) δ: 1.55-1.78 (4H, m), 1.96-2.05 (2H, m), 2.65-2.79 (1H, m), 3.11-3.22 (3H, m), 3.36-3.48 (4H, m), 3.75-4.01 (4H, m), 4.54-4.64 (2H, m), 4.92-5.05 (1H, m), 5.40 (1H, brs), 6.43 (1H, brs), 7.59 (1H, dd, J=9.0, 2.1), 7.94 (3H, s), 7.96 (1H, d, J=9.0), 8.51 (1H, s).

Elemental analysis for C$_{24}$H$_{29}$N$_4$O$_6$SCl.0.5H$_2$O
Calcd (%): C, 52.79; H, 5.54; N, 10.26
Found (%): C, 53.09; H, 5.65; N, 10.03

EXAMPLE 37

2-[3-(1-{(2S)-3-[(6-Chloronaphthalen-2-yl)sulfonyl]-2-hydroxypropanoyl}piperidin-4-yl)-2-oxotetrahydropyrimidin-1(2H)-yl]-N-methylacetamide

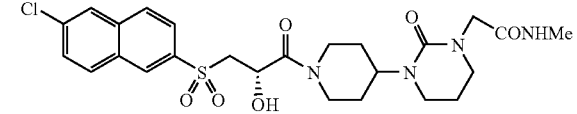

37a) Benzyl 4-[3-(methylcarbonylmethyl)-2-oxotetrahydropyrimidin-1(2H)-yl]piperidin-1-carboxylate WSC (0.39 g) was added to a solution of [3-{1-[(benzyloxy)carbonyl]piperidin-4-yl}-2-oxotetrahydropyrimidin-1 (2H)-yl]acetic acid (0.70 g) obtained in Example 36a), a solution of methylamine in THF (1.85 mL) and HOBt (0.31 g) in THF/dichloromethane (1/1, 30 mL) and the mixture was stirred at room temperature overnight. The solvent were distilled off under reduced pressure, and the residue was diluted with ethyl acetate. The mixture was washed with an aqueous saturated sodium bicarbonate solution and saturated saline solution, dried over anhydrous magnesium sulfate and then concentrated under reduced pressure. The residue was purified with basic silica gel column chromatography (ethyl acetate) to obtain the title compound (0.70 g, 97%) as a white powder.

NMR (CDCl$_3$) δ: 1.53-1.70 (4H, m), 1.89-2.01 (2H, m), 2.79 (3H, d, J=5.2), 2.80-2.86 (2H, m), 3.16 (2H, t, J=6.0), 3.34 (2H, t, J=6.0), 3.91 (2H, s), 4.25-4.31 (2H, m), 4.39-4.55 (1H, m), 5.12 (2H, s), 6.63 (1H, brs), 7.30-7.38 (5H, m).

37b) N-Methyl-2-[2-Oxo-3-(piperidin-4-yl)tetrahydropyrimidin-1(2H)-yl]acetamide According to the manner similar to in Example 34b), the title compound (0.35 g, 74%) was obtained as a white powder from benzyl 4-[3-(methylcarbonylmethyl)-2-oxotetrahydropyrimidin-1(2H)-yl]piperidin-1-carboxylate (0.70 g) obtained in Example 37a).

NMR (DMSO-d$_6$) δ: 1.85 (2H, d, J=12.6), 1.97-2.05 (2H, m), 2.16-2.32 (2H, m), 2.81 (3H, d, J=4.2), 2.95-3.08 (2H, m), 3.28 (2H, t, J=6.0), 3.36 (2H, t, J=6.0), 3.54 (2H, d, J=6.0), 3.93 (2H, s), 4.43-4.52 (1H, m).

37c) 2-[3-(1-{(2S)-3-[(6-Chloronaphthalen-2-yl)sulfonyl]-2-hydroxypropanoyl}piperidin-4-yl)-2-oxotetrahydropyrimidin-1(2H)-yl]-N-methylacetamide According to the manner similar to that in Example 1, the title compound (0.13 g, 19%) was obtained as a white powder from N-methyl-2-[2-Oxo-3-(piperidin-4-yl)tetrahydropyrimidin-1(2H)-yl]acetamide (0.32 g) obtained in Example 37b).

NMR (CDCl$_3$) δ: 1.55-1.88 (4H, m), 1.93-2.02 (2H, m), 2.65-2.78 (1H, m), 2.81 (1.5H, s), 2.82 (1.5H, s), 3.11-3.24 (3H, m), 3.34-3.53 (4H, m), 3.70-4.05 (4H, m), 4.53-4.70 (2H, m), 4.95-5.05 (1H, m), 6.47 (1H, brs), 7.59 (1H, dd, J=9.0, 2.1), 7.94 (3H, s), 7.95 (1H, d, J=9.0), 8.51 (1H, s).

Elemental analysis for C$_{25}$H$_{31}$N$_4$O$_6$SCl.0.2EtOAc
Calcd (%): C, 53.64; H, 5.86; N, 9.70
Found (%): C, 53.94; H, 5.78; N, 9.58

EXAMPLE 38

1-(1-{(2S)-3-[(6-Chloronaphthalen-2-yl)sulfonyl]-2-hydroxypropanoyl}piperidin-4-yl)-3-[(morpholin-4-yl)carbonylmethyl]tetrahydropyrimidin-2(1H)-one

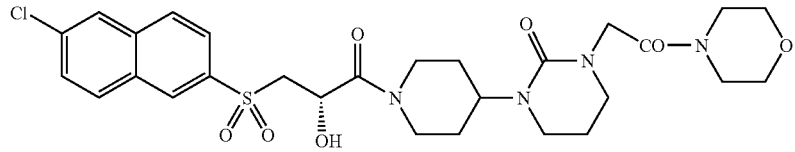

38a) Benzyl 4-[3-((morpholin-4-yl)carbonylmethyl)-2-oxotetrahydropyrimidin-1(2H)-yl]piperidin-1-carboxylate According to the manner similar to that in Example 37a), the title compound (0.51 g, 86%) was obtained as a white powder from [3-{1-[(benzyloxy)carbonyl]piperidin-4-yl}-2-oxotetrahydropyrimidin-1(2H)-yl]acetic acid (0.50 g) obtained in Example 36a) and morpholine (0.11 mL).

NMR (CDCl$_3$) δ: 1.52-1.68 (4H, m), 1.94-2.04 (2H, m), 2.75-2.90 (2H, m), 3.20 (2H, t, J=6.0), 3.34 (2H, t, J=5.7), 3.46-3.49 (2H, m), 3.58-3.62 (2H, m), 3.66-3.69 (4H, m), 4.13 (2H, s), 4.18-4.30 (2H, m), 4.43-4.53 (1H, m), 5.12 (2H, s), 7.29-7.42 (5H, m).

38b) 1-{2-[(Morpholin-4-yl)carbonylmethyl]-3-piperidin-4-yl}tetrahydropyrimidin-2(1H)-one According to the manner similar to that in Example 34b), the title compound (0.45 g, quantitative) was obtained as a white powder from benzyl 4-[3-((morpholin-4-yl)carbonylmethyl)-2-oxotetrahydropyrimidin-1(2H)-yl]piperidin-1-carboxylate (0.49 g) obtained in Example 38a).

NMR (CDCl$_3$) δ: 1.82-1.91 (2H, m), 1.95-2.05 (2H, m), 2.13-2.28 (2H, m), 2.86-3.03 (2H, m), 3.28 (2H, t, J=5.4), 3.34 (2H, t, J=6.0), 3.43-3.50 (2H, m), 3.50-3.63 (4H, m), 3.67-3.73 (4H, m), 4.12 (2H, s), 4.56-4.68 (1H, m).

38c) 1-(1-{(2S)-3-[(6-Chloronaphthalen-2-yl)sulfonyl]-2-hydroxypropanoyl}piperidin-4-yl)-3-[(morpholin-4-yl)carbonylmethyl]tetrahydropyrimidin-2(1H)-one According to the manner similar to that in Example 1, the title compound (36 mg, 6%) was obtained as a white powder from 1-{2-[(morpholin-4-yl)carbonylmethyl]-3-piperidin-4-yl}tetrahydropyrimidin-2(1H)-on (0.31 g) obtained in Example 38b).

NMR (CDCl$_3$) δ: 1.56-1.68 (2H, m), 1.70-1.88 (2H, m), 1.94-2.04 (2H, m), 2.61-2.80 (1H, m), 3.09-3.24 (3H, m), 3.32-3.42 (4H, m), 3.43-3.51 (2H, m), 3.57-3.64 (2H, m), 3.66-3.83 (5H, m), 3.90-4.00 (1H, m), 4.05-4.22 (2H, m), 4.53-4.68 (2H, m), 4.95-5.05 (1H, m), 7.59 (1H, dd, J=8.7, 2.1), 7.94 (3H, s), 7.95 (1H, d, J=8.7), 8.51 (1H, s).

Elemental analysis for C$_{28}$H$_{35}$N$_4$O$_7$SCl.0.5H$_2$O
Calcd (%): C, 54.58; H, 5.89; N, 9.09
Found (%): C, 54.62; H, 6.09; N, 9.13

EXAMPLE 39

1-(1-{(2S)-3-[(6-Chloronaphthalen-2-yl)sulfonyl]-2-hydroxypropanoyl}piperidin-4-yl)-3-(2-methoxyethyl)tetrahydropyrimidin-2(1H)-one

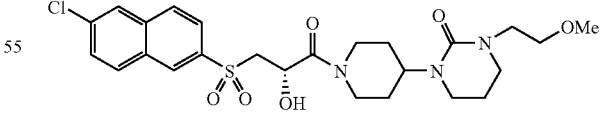

39a) Benzyl 4-[3-(2-hydroxyethyl)-2-oxotetrahydropyrimidin-1(2H)-yl]piperidin-1-carboxylate A solution of benzyl 4-[3-(tert-butoxycarbonylmethyl)-2-oxotetrahydropyrimidin-1(2H)-yl]piperidin-1-carboxylate (0.60 g) obtained in Example 35a) and lithium borohydride (0.091 g) in THF (15 mL) was refluxed for 5 hours. The reaction mixture was allowed to stand at room temperature and poured into an aqueous saturated ammonia solution under ice-cooling. The organic layer was separated, and the aqueous layer was extracted with dichloromethane. The organic layers were combined, washed with a saturated saline solution, dried over anhydrous magnesium sulfate and then concentrated under reduced pressure. The residue was purified by silica gel column chromatography (ethyl acetate to ethyl acetate/methanol=95/5) to obtain the title compound (0.50 g, 99%) as a colorless oil.

NMR (CDCl$_3$) δ: 1.47-1.66 (4H, m), 1.90-1.98 (2H, m), 2.80-2.95 (2H, m), 3.14 (2H, t, J=5.7), 3.31 (2H, t, J=6.0), 3.47 (2H, t, J=4.5), 3.70-3.80 (2H, m), 4.20-4.38 (2H, m), 4.42-4.53 (1H, m), 5.12 (2H, s), 7.28-7.42 (5H, m).

39b) Benzyl 4-[3-(2-methoxyethyl)-2-oxotetrahydropyrimidin-1(2H)-yl]piperidin-1-carboxylate Sodium hydride (60% in oil; 71 mg) was added under ice-cooling to a solution of benzyl 4-[3-(2-hydroxyethyl)-2-oxotetrahydropyrimidin-1(2H)-yl]piperidin-1-carboxylate (0.59 g) obtained in Example 39a) in THF (30 mL), and the mixture was stirred at room temperature for 30 minutes. Methyl iodide (0.11 mL) was added to the reaction mixture, followed by stirring at room temperature for 15 hours. The reaction solution was diluted with an aqueous saturated ammonia solution to separate the organic layer. The organic layer was washed with saturated saline solution, dried over anhydrous magnesium sulfate and concentrated under reduced pressure to obtain the title compound (0.60 g, quantitative) as a white powder.

NMR (CDCl$_3$) δ: 1.52-1.66 (4H, m), 1.85-1.93 (2H, m), 2.80-2.90 (2H, m), 3.11 (2H, t, J=6.0), 3.34 (3H, s), 3.34 (2H, t, J=6.0), 3.46-3.56 (4H, m), 4.20-4.30 (2H, m), 4.46-4.56 (1H, m), 5.12 (2H, s), 7.28-7.39 (5H, m).

39c) 1-(2-Methoxyethyl)-3-(piperidin-4-yl)tetrahydropyrimidin-2(1H)-one

According to the manner similar to that in Example 34b), the title compound (0.36 g, quantitative) was obtained as a white powder from benzyl 4-[3-(2-methoxyethyl)-2-oxotetrahydropyrimidin-1(2H)-yl]piperidin-1-carboxylate (0.60 g) obtained in Example 39b).

NMR (CDCl$_3$) δ: 1.62-1.73 (2H, m), 1.86-1.95 (2H, m), 2.69-2.78 (2H, m), 3.10-3.21 (6H, m), 3.30-3.36 (5H, m), 3.46-3.56 (4H, m), 4.38-4.49 (1H, m).

39d) 1-(1-{(2S)-3-[(6-Chloronaphthalen-2-yl)sulfonyl]-2-hydroxypropanoyl}piperidin-4-yl)-3-(2-methoxyethyl)tetrahydropyrimidin-2(1H)-one According to the manner similar to that in Example 1, the title compound (0.32 g, 40%) was obtained as a white powder from 1-(2-methoxyethyl)-3-(piperidino-4-yl)tetrahydropyrimidin-2(1H)-one (0.36 g) obtained in Example 39c).

NMR (CDCl$_3$) δ: 1.55-1.93(6H, m), 2.62-2.80 (1H, m), 3.09-3.25 (3H, m), 3.30-3.40 (7H, m), 3.40-3.55 (4H, m), 3.73-4.00 (2H, m), 4.53-4.70 (1H, m), 4.95-5.05 (1H, m), 7.59 (1H, dd, J=8.7, 1.8), 7.94 (3H, s), 7.95 (1H, d, J=8.7), 8.51 (1H, s).

Elemental analysis for C$_{25}$H$_{32}$N$_3$O$_6$SCl
Calcd (%): C, 55.81; H, 5.99; N, 7.81
Found (%): C, 55.58; H, 6.14; N, 7.80

EXAMPLE 40

1-(2-{[tert-Butyl(dimethyl)silyl]oxy}ethyl)-3-(1-{(2S)-3-[(6-chloronaphthalen-2-yl)sulfonyl]-2-hydroxypropanoyl}piperidin-4-yl)tetrahydropyrimidin-2(1H)-one

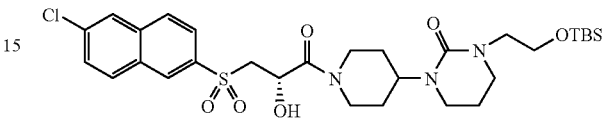

40a) Benzyl 4-[3-(2-{[tert-butyl(dimethyl)silyl]oxy}ethyl)-2-oxotetrahydropyrimidin-1(2H)-yl]piperidin-1-carboxylate tert-Butyl(dimethyl)silyl chloride (0.30 g) was added to a solution of benzyl 4-[3-(2-hydroxyethyl)-2-oxotetrahydropyrimidin-1(2H)-yl]piperidin-1-carboxylate (0.60 g) obtained in Example 39a) and triethylamine (0.28 mL) in dichloromethane (20 mL) and the mixture was stirred at room temperature overnight. The reaction mixture was washed with an aqueous saturated sodium bicarbonate solution and saturated saline solution, dried over anhydrous magnesium sulfate and then concentrated under reduced pressure. The residue was purified by silica gel column chromatography (from hexane/ethyl acetate=1/1 to hexane/ethyl acetate=1/4) to obtain the title compound (0.78 g, 99%) as a colorless oil.

NMR (CDCl$_3$) δ: 0.03 (6H, s), 0.87 (9H, s), 1.54-1.68 (4H, m), 1.83-1.88 (2H, m), 2.78-2.88 (2H, m), 3.09 (2H, t, J=5.7), 3.34-3.51 (4H, m), 3.74 (2H, t, J=5.7), 4.15-4.30 (2H, m), 4.46-4.58 (1H, m), 5.38 (2H, s), 7.28-7.37 (5H, m).

40b) 1-(2-{[tert-Butyl(dimethyl)silyl]oxy}ethyl)-3-(piperidin-4-yl)tetrahydropyrimidin-2(1H)-one According to the manner similar to that in Example 1, the title compound (0.55 g, quantitative) was obtained as a white powder from benzyl 4-[3-(2-{[tert-butyl(dimethyl)silyl]oxy}ethyl)-2-oxotetrahydropyrimidin-1(2H)-yl]piperidin-1-carboxylate (0.78 g) obtained in Example 40a).

NMR (CDCl$_3$) δ: 0.05 (6H, s), 0.89 (9H, s), 1.50-1.60 (4H, m), 1.85-1.95 (2H, m), 2.65-2.75 (2H, t, J=5.7), 3.05-3.20 (4H, m), 3.35-3.45 (4H, m), 3.77 (2H, t, J=5.7), 4.35-4.50 (1H, m).

40c) 1-(2-{[tert-Butyl(dimethyl)silyl]oxy}ethyl)-3-(1-{(2S)-3-[(6-chloronaphthalen-2-yl)sulfonyl]-2-hydroxypropanoyl}piperidin-4-yl)tetrahydropyrimidin-2(1H)-one According to the manner similar to that in Example 1, the title compound (0.45 g, 44%) was obtained as a white powder from 1-(2-{[tert-butyl(dimethyl)silyl]oxy}ethyl)-3-(piperidin-4-yl)tetrahydropyrimidin-2(1H)-one (0.55 g) obtained in Example 40b).

NMR (CDCl$_3$) δ: 0.50 (6H, s), 0.89 (9H, s), 1.49-1.79 (4H, m), 1.82-1.93 (2H, m), 2.65-2.79 (1H, m), 3.08-3.22 (3H, m), 3.37-3.46 (6H, m), 3.74 (2H, t, J=5.4), 3.83-3.95 (1H, m), 4.57-4.65 (2H, m), 4.94-5.01 (1H, m), 7.58 (1H, dd, J=9.0, 2.1), 7.93 (3H, s), 7.95 (1H, d, J=9.0), 8.51 (1H, s).
Elemental analysis for $C_{30}H_{44}N_3O_6SClSi$
Calcd (%): C, 56.45; H, 6.95; N, 6.58
Found (%): C, 56.30; H, 7.12; N, 6.64

EXAMPLE 41

1-(1-{(2S)-3-[(6-Chloronaphthalen-2-yl)sulfonyl]-2-hydroxypropanoyl}piperidin-4-yl)-3-(2-hydroxyethyl)tetrahydropyrimidin-2(1H)-one

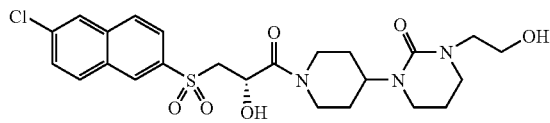

Tetrabutylammonium fluoride (0.12 g) was added to a solution of 1-(2-{[tert-butyl(dimethyl)silyl]oxy}ethyl)-3-(1-{(2S)-3-[(6-chloronaphthalen-2-yl)sulfonyl]-2-hydroxypropanoyl}piperidin-4-yl)tetrahydropyrimidin-2(1H)-one (0.25 g) obtained in Example 40c) in THF (10 mL), and the mixture was stirred at room temperature overnight. The solvent was distilled off under reduced pressure, and the residue was diluted with ethyl acetate. The mixture was washed with an aqueous 5% citric acid solution and saturated saline solution, dried over anhydrous magnesium sulfate and then concentrated under reduced pressure. The residue was purified by basic silica gel column chromatography (ethyl acetate/methanol=95/5 to ethyl acetate/methanol=90/10) to obtain the title compound (0.11 g, 54%) as a white powder.

NMR (CDCl$_3$) δ: 1.53-1.81 (4H, m), 1.94-1.98 (2H, m), 2.65-2.80 (1H, m), 3.12-3.24 (3H, m), 3.31-3.51 (6H, m), 3.73-3.86 (3H, m), 3.94-4.08 (2H, m), 4.55-4.70 (2H, m), 4.93-5.03 (1H, m), 7.59 (1H, dd, J=9.0, 2.1), 7.94 (3H, s), 7.96 (1H, d, J=9.0), 8.51 (1H, s).

Elemental analysis for $C_{24}H_{30}N_3O_6SCl\cdot0.3H_2O$
Calcd (%): C, 54.45; H, 5.83; N, 7.94
Found (%): C, 54.45; H, 5.96; N, 7.75

EXAMPLE 42

(R,S)-1-(1-{3-[(6-Chloronaphthalen-2-yl)sulfonyl]-2-hydroxypropanoyl}piperidin-4-yl)tetrahydropyrimidin-2(1H)-one

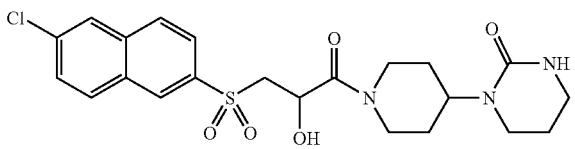

According to the manner similar to that in Example 1, the title compound (0.14 g, 20%) was obtained as a white powder from 1-(piperidin-4-yl)tetrahydropyrimidin-2(1H)-one (0.18 g) and (R,S)-3-[(6-chloronaphthalen-2-yl)sulfonyl]-2-hydroxypropionoic acid (0.31 g).

NMR (CDCl$_3$) δ: 1.53-1.98 (6H, m), 2.66-2.77 (1H, m), 3.11-3.20 (3H, m), 3.26-3.30 (2H, m), 3.40-3.48 (2H, m), 3.94-3.98 (1H, m), 4.54-4.66 (2H, m), 4.75 (1H, brs), 4.94-5.05 (1H, m), 7.57 (1H, dd, J=7.8, 2.1), 7.93 (3H, s), 7.94 (1H, d, J=7.8), 8.50 (1H, s).

Elemental analysis for $C_{22}H_{26}N_3O_5SCl$
Calcd (%): C, 54.04; H, 5.57; N, 8.59
Found (%): C, 54.06; H, 5.80; N, 8.34

EXAMPLE 43

(2S)-3-[(6-Chloronaphthalen-2-yl)sulfonyl]-1-(2-imino-1,4'-bipiperidin-1'-yl)-1-oxopropan-2-ol trifluoroacetate

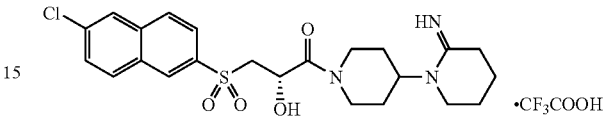

43a) tert-Butyl 2-thioxo-1,4'-bipiperidin-1'-carboxylate

A solution of tert-butyl 2-oxo-1,4'-bipiperidin-1'-carboxylate (2.8 g) and Lawesson's reagent (2.0 g) in toluene (30 mL) was refluxed for one hour. Toluene was distilled off under reduced pressure, and the residue was diluted with dichloromethane, and washed with an aqueous 1N sodium hydroxide solution and saturated saline solution. This dichloromethane solution was dried over anhydrous magnesium sulfate and then concentrated under reduced pressure. The residue was purified by silica gel column chromatography (hexane/ethyl acetate=2/1 to 1/2) to obtain the title compound (1.9 g, 64%) as a white powder.

NMR (CDCl$_3$) δ: 1.49(9H, s), 1.52-1.65 (2H, m), 1.68-1.88 (6H, m), 2.84 (2H, t, J=12.6), 3.04 (2H, t, J=6.6), 3.29 (2H, t, J=6.0), 4.14-4.30 (2H, m), 5.70-5.81 (1H, m).

43b) tert-Butyl 2-imino-1,4'-bipiperidin-1'-carboxylate

A solution of tert-butyl 2-thioxo-1,4'-bipiperidin-1'-carboxylate (0.70 g) obtained in Example 43a) and methyl iodide (0.4 g) in acetone (10 mL) was stirred at room temperature for 15 hours. The reaction mixture was concentrated under reduced pressure. A solution of the resulting residue and ammonium acetate (0.22 g) in ethanol (10 mL) was refluxed for 3 hours. Ethanol was distilled off under reduced pressure, and the residue was purified by silica gel column chromatography to obtain the title compound (0.66 g, quantitative) as a white powder.

NMR (CDCl$_3$) δ: 1.45 (9H, s), 1.55-1.70 (2H, m), 1.75-1.80 (6H, m), 2.87 (2H, t, J=6.3), 3.20-3.40 (4H, m), 4.08-4.28 (2H, m), 4.64-4.75 (1H, m).

43c) (2S)-3-[(6-Chloronaphthalen-2-yl)sulfonyl]-1-(2-imino-1,4'-bipiperidin-1'-yl)-1-oxopropan-2-ol trifluoroacetate A solution of 4N hydrochloric acid in ethyl acetate (10 mL) was added to tert-butyl 2-imino-1,4'-bipiperidin-1'-carboxylate (0.66 g) obtained in Example 43b), and the mixture was stirred at room temperature for 8 hours. The reaction mixture was concentrated under reduced pressure. To a solution of the resulting residue, (2S)-3-[(6-chloronaphthalen-2-yl)sulfonyl]-2-hydroxypropionic acid (0.82 g), HOBt (0.40 g) and triethylamine (0.76 mL) in DMF (40 mL) was added WSC (0.47 g), and the mixture was stirred at room temperature for 15 hours. DMF was distilled off under reduced pressure, and the residue was diluted with chloroform, and washed with an aqueous saturated sodium bicarbonate solution and saturated saline solution. This chloroform solution was dried over anhydrous magnesium sulfate, and then concentrated under reduced pressure. The residue was purified by basic silica gel column chromatography (chloroform to chloroform/methanol=95/5) and further purified with basic silica gel column chromatography (ethyl acetate/methanol=9/1 to 7/3). The crude product obtained was purified with reverse phase preparative HPLC to obtain the title compound (28 mg, 2%) as a white powder.

NMR (CDCl$_3$) δ: 1.50-1.96 (8H, m), 2.54 (2H, t, J=6.2), 2.70-2.90 (1H, m), 3.05-3.15 (2H, m), 3.18-3.46 (3H, m), 3.90-3.97 (2H, m), 4.50-4.84 (3H, m), 4.91-5.01 (1H, m), 7.54 (1H, dd, J=8.8, 2.0), 7.89 (3H, s), 7.90 (1H, d, J=8.8), 8.46 (1H, s).

Elemental analysis for C$_{23}$H$_{28}$N$_3$O$_4$SCl.CF$_3$COOH.1.5H$_2$O
Calcd (%): C, 48.50; H, 5.21; N, 6.79
Found (%): C, 48.42; H, 5.01; N, 6.92

EXAMPLE 44

1'-{3-[(6-Chloronaphthalen-2-yl)sulfonyl]propanoyl}-1,4'-bipiperidin-2-imine trifluoroacetate

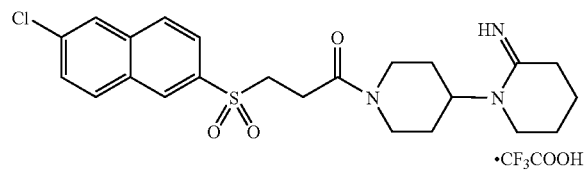

According to the manner similar to that in Example 1, the title compound (0.11 g, 9%) was obtained as a white powder from the tert-butyl 2-imino-1,4'-bipiperidin-1'-carboxylate (0.70 g) obtained in Example 43b) and 3-[(6-chloronaphthalen-2-yl)sulfonyl]propionic acid (0.82 g).

NMR (CDCl$_3$) δ: 1.57-1.93 (8H, m), 2.72 (2H, t, J=6.0), 2.78-3.04 (3H, m), 3.19 (2H, t, J=5.8), 3.31-3.72 (3H, m), 3.86-3.92 (1H, m), 4.60-4.75 (2H, m), 7.59 (1H, dd, J=8.8, 1.8), 7.93 (3H, s), 7.95 (1H, d, J=8.4), 8.48 (1H, s).

Elemental analysis for C$_{23}$H$_{28}$N$_3$O$_3$SClδ.CF$_3$COOH.0.5H$_2$O.0.1EtOAc
Calcd (%): C, 51.37; H, 5.23; N, 7.08
Found (%): C, 51.65; H, 5.50; N, 6.94

EXAMPLE 45

1-(1-{(2S)-3-[(6-Chloronaphthalen-2-yl)sulfonyl]-2-hydroxypropanoyl}piperidin-4-yl)dihydropyrimidin-2,4(1H,3H)-dione

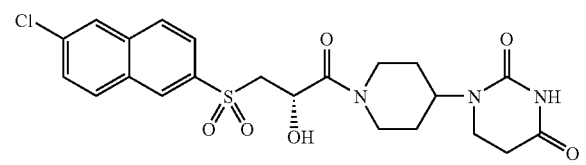

45a) Benzyl 4-[(3-methoxy-3-oxopropyl)amino]piperidin-1-carboxylate

A solution of benzyl 4-oxopiperidin-1-carboxylate (10 g), β-alanine methyl ester monohydrochloride (5.99 g), acetic acid (4 mL) and sodium triacetoxyborohydride (10.9 g) in dichloroethane (400 mL) was stirred overnight. The reaction mixture was washed with aqueous saturated sodium bicarbonate solution and saturated saline solution, dried over anhydrous sodium sulfate, and concentrated under reduced pressure to obtain the title compound (12.0 g, 87%) as a colorless oil.

NMR (CDCl$_3$) δ: 1.26-1.39(2H, m), 1.89 (2H, d, J=11.5), 2.56 (2H, t, J=6.6), 2.65-2.74 (1H, m), 2.85-2.96 (3H, m), 3.69 (3H, s), 3.86-3.92 (2H, m), 4.05-4.18 (2H, m), 5.12 (2H, s), 7.29-7.40 (5H, m).

45b) N-{1-[(Benzyloxy)carbonyl]piperidin-4-yl}-N-(tert-butoxycarbonyl)-β-alanine Di-tert-butyl dicarbonate (8.18 g) was added to a solution of benzyl 4-[(3-methoxy-3-oxopropyl)amino]piperidin-1-carboxylate (12.0 g) obtained in Example 45a) in ethanol (200 mL) at room temperature. The mixture was stirred for 15 hours and ethanol was distilled off under reduced pressure. The residue was diluted with ethyl acetate, washed with a saturated saline solution, dried over anhydrous magnesium sulfate, and concentrated under reduced pressure. To a solution of the resulting residue in ethanol (100 mL) was added an aqueous 1N sodium hydroxide solution at room temperature, and the mixture was stirred for 15 hours. Ethanol was distilled off under reduced pressure, and the resulting aqueous solution was adjusted to pH 3 with 1N hydrochloric acid, followed by extraction with dichloromethane. The organic layer was washed with saturate saline solution, dried over anhydrous sodium sulfate, and concentrated under reduced pressure. The residue was recrystallized from ethyl acetate-hexane to obtain the title compound (8.81 g, 58%) as a white powder.

NMR (CDCl$_3$) δ: 1.39 (9H, s), 1.50-1.70 (4H, m), 2.39 (2H, t, J=7.4), 2.70-2.90 (2H, m), 3.28 (2H, t, J=7.4 ), 3.70-3.90 (1H, m), 4.06 (2H, d, J=13.5), 5.07 (2H, s), 7.34-7.37 (5H, m), 12.2 (1H, brs).

45c) Benzyl 4-[(3-amino-3-oxopropyl)(tert-butoxycarbonyl)amino]piperidin-1-carboxylate A solution of N-{1-[(benzyloxy)carbonyl]piperidin-4-yl}-N-(tert-butoxycarbonyl)-β-alanine (4.06 g) obtained in Example 45b), WSC (1.92 g) and HOBt.NH$_3$ (1.52 g) in DMF (40 mL) was stirred overnight at room temperature, and DMF was distilled off under reduced pressure. The residue was diluted with dichloromethane, washed with an aqueous saturated sodium bicarbonate solution and saturated saline solution, dried over anhydrous magnesium sulfate, and concentrated under reduced pressure. The residue was purified by basic silica gel column chromatography (from ethyl acetate/hexane=1/1 to ethyl acetate) to obtain the title compound (3.38 g, 83%) as a white amorphous powder.

NMR (CDCl$_3$) δ: 1.46 (9H, s), 1.60-1.75 (4H, m), 2.45 (2H, t, J=7.2), 2.70-2.85 (2H, m), 3.35-3.45 (2H, m), 4.20-4.35 (2H, m), 5.11 (2H, s), 5.48-5.84 (1H, m), 7.28-7.35 (5H, m).

45d) Benzyl 4-(2,4-dioxotetrahydropyrimidin-1(2H)-yl)piperidin-1-carboxylate 4N Hydrogen chloride in ethyl acetate (4 mL) was added to a solution of benzyl 4-[(3-amino-3-oxopropyl)(tert-butoxycarbonyl)amino]piperidin-1-carboxylate (3.38 g) obtained in Example 45c) in ethyl acetate (16 mL), and the mixture was stirred at room temperature for 15 hours. The white solid (2.73 g) formed was collected by filtration. A solution of the resulting white solid (1.0 g), CDI (0.47 g) and DBU (0.89 g) in dichloroethane (30 mL) was refluxed for 15 hours. The reaction mixture was washed with an aqueous 5% citric acid solution and saturated saline solution, dried over anhydrous sodium sulfate, and concentrated under reduced pressure. The residue was purified by silica gel column chromatography (ethyl acetate) to obtain the title compound (0.21 g, 21%) as a white powder.

NMR (CDCl$_3$) δ: 1.50-1.63 (4H, m), 2.46 (2H, t, J=6.6), 2.80-2.95 (2H, m), 3.26 (2H, t, J=6.6), 4.09 (2H, d, J=12.6), 4.20-4.25 (1H, m), 5.06 (2H, s), 7.28-7.37 (5H, m), 10.1 (1H, s).

45e) 1-Piperidin-4-yl-dihydropyrimidin-2,4(1H,3H)-dione

A solution of benzyl 4-(2,4-dioxotetrahydropyrimidin-1(2H)-yl)piperidin-1-carboxylate (0.18 g) obtained in Example 45d) and 20% palladium on carbon (containing 60% water, 36 mg) in DMF (10 mL) was stirred at room temperature for 3 hours under a hydrogen atmosphere, and the catalyst was removed by filtration. The filtrate was concentrated under reduced pressure to obtain the title compound (0.11 g, quantitative) as a white powder.

NMR (CDCl$_3$) δ: 1.45-1.63 (4H, m), 2.41-2.55 (4H, m), 2.98 (2H, d, J=12.0), 3.26 (2h, t, J=6.6), 4.01-4.18 (1H, m), 10.0 (1H, brs).

45f) 1-(1-{(2S)-3-[(6-Chloro-2-naphthyl)sulfonyl]-2-hydroxypropanoyl}piperidin-4-yl)dihydropyrimidin-2,4(1H,3H)-dione To a solution of 1-piperidin-4-yl-dihydropyrimidin-2,4(1H,3H)-dione (105 mg) obtained in Example 4 5e), HOBt (83 mg) and (2S)-3-[(6-chloro-2-naphthyl)sulfonyl]-2-hydroxypropionic acid (170 mg) in DMF (10 mL) was added WSC (105 mg) at room temperature. The mixture was stirred at room temperature for 3 days, and DMF was distilled off under reduced pressure. The residue was diluted with chloroform, washed with an aqueous saturated sodium bicarbonate solution and saturated saline solution, dried over anhydrous sodium sulfate, and concentrated under reduced pressure. The residue was purified by basic silica gel column chromatography (ethyl acetate to ethyl acetate/methanol=10/1), and recrystallized from ethanol to obtain the title compound (24 mg, 9%) as a white powder.

NMR (DMSO) δ: 1.31-1.63 (3H, m), 2.43-2.56 (3H, m), 3.00-3.06 (1H, m), 3.19 (2H, t, J=6.6), 3.25-3.39 (1H, m), 3.58-3.66 (1H, m), 3.77-3.86 (1H, m), 3.99 (1H, d, J=14.7), 4.20-4.35 (2H, m), 4.70-4.85 (1H, m), 5.72 (1H, t, J=9.0), 7.72 (1H, d, J=8.7), 7.98 (1H, dd, J=1.5, 8.7), 8.15 (1H, d, J=9.0), 8.25 (1H, d, J=4.2), 8.29 (1H, s), 8.62 (1H, s), 10.1 (1H, d, J=4.2).

Elemental analysis for C$_{22}$H$_{24}$ClN$_3$O$_6$S.0.5H$_2$O

Calcd (%) : C, 52.54 ; H, 5.01 ; N, 8.35

Found (%) : C, 52.85 ; H, 4.95 ; N, 8.49

EXAMPLE 46

1-(1-{(2S)-3-[(6-Chloro-2-naphthyl)sulfonyl]-2-hydroxypropanoyl}piperidin-4-yl)-4-hydroxytetrahydropyrimidin-2(1H)-one

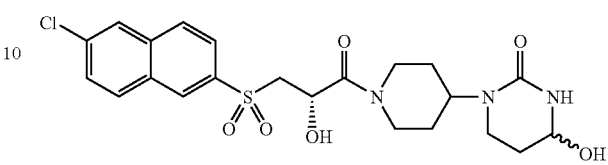

46a) N-(3,3-Diethoxypropyl)-N-piperidin-4-yl urea

A solution of benzyl 4-oxopiperidin-1-carboxylate (11.2 g), 3,3-dietoxypropane-1-amine (7.0 g), acetic acid (3 mL) and sodium triacetoxyborohydride (12.7 g) in dichloroethane (300 mL) was stirred at room temperature overnight. The reaction mixture was washed with an aqueous saturated sodium bicarbonate solution and saturated saline solution, dried over anhydrous sodium sulfate, and concentrated, under reduced pressure. A solution of the resulting residue and potassium isocyanate (3.4 g) in a mixture of methanol/acetic acid (190 mL/10 mL) was refluxed for 3 hours. Potassium isocyanate (3.4 g) was further added thereto and the mixture was refluxed for additional 1 hour. The solvent was distilled off under reduced pressure, and the residue was diluted with ethyl acetate and an aqueous saturated sodium bicarbonate solution, followed by extraction with ethyl acetate. The organic layer was washed with saturated saline solution, dried over anhydrous magnesium sulfate, and concentrated under reduced pressure. The residue was purified by basic silica gel column chromatography (from ethyl acetate/hexane=4/1 to ethyl acetate) to obtain benzyl 4-[(aminocarbonyl)(3,3-diethoxypropyl)amino]piperidin-1-carboxylate (12.1 g, 62%) as a white powder. A solution of the resulting benzyl 4-[(aminocarbonyl)(3,3-diethoxypropyl)amino]piperidin-1-carboxylate (12.1 g) and 20% palladium on carbon (containing 50% water, 0.24 g) in methanol (300 mL) was stirred at room temperature overnight under a hydrogen atmosphere, and the catalyst was removed by filtration. The filtrate was concentrated under reduced pressure to obtain the title compound as a white powder.

NMR (CDCl$_3$) δ: 1.12 (6H, t, J=6.9), 1.39-1.47 (4H, m), 1.66-1.73 (2H, m), 2.41-2.50 (2H, m), 2.93 (2H, d, J=12.3), 3.03 (2H, t, J=7.8), 3.37-3.64 (4H, m), 3.72-3.88 (1H, m), 4.50 (1H, t, J=5.4), 5.72 (2H, brs).

46b) N-(1-{(2S)-3-[6-Chloro-2-naphthyl)sulfonyl]-2-hydroxypropanoyl}piperidin-4-yl)-N-(3,3-diethoxypropyl)urea To a solution of N-(3,3-diethoxypropyl)-N-piperidin-4-yl urea (7.79 g) obtained in Example 46a), HOBt (4.81 g) and (2S)-3-[(6-chloro-2-naphthyl)sulfonyl]-2-hydroxypropionic acid (9.88 g) in DMF (200 mL) was added WSC (6.02 g) at room temperature. The mixture was stirred at room temperature overnight, and DMF was distilled off under reduced pressure. The residue was diluted with chloroform, washed with an aqueous saturated sodium bicarbonate solution and saturated saline solution, dried over anhydrous sodium sulfate, and concentrated under reduced pressure. The residue was purified by basic silica gel column chromatography (from ethyl acetate to ethyl acetate/ethanol=97/3) to obtain the title compound (9.41 g, 52%) as a white powder.

NMR (CDCl$_3$) δ: 1.21 (6H, t, J=8.7), 1.47-1.65 (2H, m), 1.73-1.91 (4H, m), 2.63-2.76 (1H, m), 3.10-3.17 (3H, m), 3.35-3.56 (4H, m), 3.63-3.73 (2H, m), 3.95-4.02 (2H, m), 4.37-4.61 (3H, m), 4.98-5.08 (3H, m), 7.58 (1H, dd, J=2.1 and 8.7), 7.93 (3H, s), 7.95 (1H, d, J=8.7), 8.51 (1H, s).

46c) 1-(1-{(2S)-3-[(6-Chloro-2-naphthyl)sulfonyl]-2-hydroxypropanoyl}piperidin-4-yl)-4-hydroxytetrahydropyrimidin-2(1H)-one N-(1-{(2S)-3-[6-Chloro-2-naphthyl)sulfonyl]-2-hydroxypropanoyl}piperidin-4-yl)-N-(3,3-diethoxypropyl) urea (0.38 g) was injected to reverse preparative HPLC and obtain a fraction containing the main product. The fraction obtained was made basic with sodium bicarbonate, and acetonitrile was distilled off under reduced pressure. The resulting aqueous solution was extracted with ethyl acetate, and the organic layer was dried over anhydrous magnesium sulfate, and concentrated under reduced pressure to obtain the title compound (0.33 g, 99%) as a white powder.

NMR (DMSO) δ: 1.20-1.73 (6H, m), 2.42-2.56 (1H, m), 2.94-3.23 (3H, m), 3.58-3.66 (1H, m), 3.76-4.00 (2H, m), 4.23-4.38 (2H, m), 4.70-4.85 (2H, m), 5.42-5.47 (1H, m), 5.66-5.77 (1H, m), 6.80 (1H, brs), 7.72 (1H, dd, J=2.1 and 8.7), 7.97 (1H, dd, J=1.8 and 8.7), 8.15 (1H, d, J=8.7), 8.23 (1H, s), 8.27 (1H, d, J=9.0), 8.62 (1H, s).

FORMULATION EXAMPLE 1

An FXa inhibitor (for example, a pharmaceutical composition for treating deep vein thrombosis, cardiogenic cerebral infarction and the like) containing, as an active ingredient, the compound represented by the formula (I) or a salt thereof of the present invention can be produced, for example, by the following formulations.

Further, in the following formulations, the ingredients (additives) other than active ingredient may be those described in Japanese Pharmacopoeia, Pharmaceutical Specification out of Japanese Pharmacopoeia, or Pharmaceutical Additive Specification, and the like.

| 1. Capsules | |
|---|---|
| (1) Compound obtained in Example 11 | 120 mg |
| (2) Lactose | 210 mg |
| (3) Microcrystalline cellulose | 27 mg |
| (4) Magnesium stearate | 3 mg |
| One capsule | 360 mg |

(1), (2), (3) and a half of (4) are mixed and then granulated. The remainder of (4) is added to the granules and the whole is encapsulated in a gelatin capsule.

| 2. Capsules | |
|---|---|
| (1) Compound obtained in Example 25 | 120 mg |
| (2) Lactose | 210 mg |
| (3) Microcrystalline cellulose | 27 mg |
| (4) Magnesium stearate | 3 mg |
| One capsule | 360 mg |

(1), (2), (3) and a half of (4) are mixed and then granulated. The remainder of (4) is added to the granules and the whole is encapsulated in a gelatin capsule.

| 3. Tablets | |
|---|---|
| (1) Compound obtained in Example 11 | 120 mg |
| (2) Lactose | 174 mg |
| (3) Cornstarch | 54 mg |
| (4) Microcrystalline cellulose | 10.5 mg |
| (5) Magnesium stearate | 1.5 mg |
| One tablet | 360 mg |

(1), (2), (3), 2/3 of (4) and a half of (5) are mixed and then granulated. The remainders of (4) and (5) are added to the granules, followed by compressing into a tablet.

| 4. Tablets | |
|---|---|
| (1) Compound obtained in Example 25 | 120 mg |
| (2) Lactose | 174 mg |
| (3) Cornstarch | 54 mg |
| (4) Microcrystalline cellulose | 10.5 mg |
| (5) Magnesium stearate | 1.5 mg |
| One tablet | 360 mg |

(1), (2), (3), 2/3 of (4) and a half of (5) are mixed and then granulated. The remainders of (4) and (5) are added to the granules, followed by compressing into a tablet.

FORMULATION EXAMPLE 2

After 50 mg of the compound obtained in Example 11 is dissolved in 50 ml of Japanese Pharmacopoeia distilled water for injection, Japanese Pharmacopoeia distilled water for injection is further added such that the whole volume is 100 mL. This solution is filtered under sterilizing condition. One milliliter aliquot of this solution is filled into a vial for injection, lyophilized, and sealed.

FORMULATION EXAMPLE 3

After 50 mg of the compound obtained in Example 43 is dissolved in 50 ml of Japanese Pharmacopoeia distilled water for injection, Japanese Pharmacopoeia distilled water for injection is further added such that the whole volume is 100 mL. This solution is filtered under sterilizing condition. One milliliter aliquot of this solution is filled into a vial for injection, lyophilized, and sealed.

EXPERIMENTAL EXAMPLE 1

(1) Inhibitory Action of Human Activated Blood Coagulation Factor X (FXa):

Test Method: A solution (225 μL) of 0.05M tris-hydrochloric acid buffers (pH=8.3) containing 0.145 M of sodium chloride and 2 mM of calcium chloride, a test compound (5 μL) dissolved in dimethyl sulfoxide) and human FXa (10 μL, 0.3 unit/ml) were added to a 96-well microplate and reacted at 37° C. for about 10 minutes, and then a substrate (10 μL, 3 mM, S-2765) was added to be reacted at 37° C. for 10 minutes. Then, after aqueous 50% acetic acid (25 μL) was added there to stop the reaction, the change of absorbance at 405 nm was measured by a microplate reader, and a concentration inhibiting FXa activity by 50% ($IC_{50}$) was calculated.

(2) In vitro Coagulation Time Assay (2-1) Prothrombin Time (PT) Assay:

This was measured by an automatic blood coagulation time measuring apparatus (STA compact, DIAGNOSTICA STAGO) using a PT reagent (Roche Diagnostics). A test compound (3 μL) was added to human normal plasma (97 μL, fresh human plasma FFP, Sekisui Chemical Co., Ltd.), and preliminarily heated at 37° C. for 4 minutes. After a thromboplastin solution (100 μL) of rabbit brain originated tissue factor was added to the above-mentioned plasma (50 μL), a time until coagulation was measured. The test compound was used by being dissolved in dimethyl sulfoxide (DMSO). A concentration at which the coagulation time was prolonged by 2-fold was calculated based on the coagulation time when DMSO was added in place of the test drug.

(2-2) Activated Partial Thromboplastin Time (APTT) Assay:

This was measured by an automatic blood coagulation time measuring apparatus using STA-APTT (Roche Diagnostics). A test compound (3 μL) was added to human normal plasma (97 μL). An activated partial thromboplastin solution (50 μL) was added to plasma (50 μL), and preliminarily heated at 37° C. for 4 minutes. After a 25 mmol/L $CaCl_2$ solution (50 μl) was added thereto, a time until coagulation was measured. The test compound was used by being dissolved in DMSO. A concentration at which the coagulation time was prolonged by 2-fold was calculated in like manner as (2-1).

(2-3) Thrombin Time (TT) Assay:

This was measured by an automatic blood coagulation time measuring apparatus using a fibrinogen reagent (Roche Diagnostics). After the fibrinogen reagent (containing thrombin) was dissolved with distilled water (5 mL), it was adjusted by being diluted by 20-fold with physiological saline in which 0.5% bovine serum albumin was added. A test compound (3 μL) was added to human normal plasma (97 μL, fresh human plasma FFP, Sekisui Chemical Co., Ltd.), and preliminarily heated at 37° C. for 4 minutes. After the thromboplastin solution (100 μL) was added to the above-mentioned plasma (50 μL), a time until coagulation was measured. The test compound was used by being dissolved in dimethyl sulfoxide (DMSO). A concentration at which the coagulation time was elongated by 2-fold was calculated in like manner as (2-1).

(3) Methods on Ex vivo Anti-FXa Effect and in Vivo Antithrombotic and Bleeding Time Prolonging Effects (3-1) Ex vivo Plasma Anti-Factor Xa (FXa) Activity in Monkeys Male Cynomolgus monkeys (3.6-5.5 kg, Keari Co., Japan) were used. Test compounds were suspended in 0.5% methyl cellulose and orally administered under fasting or feeding condition. Blood samplings were performed before and 1, 2, 4, 8 and 24 hr after the administration. Plasma samples were prepared by centrifugation (20,600×g) for 10 min at 4° C. Anti-FXa activity was measured with clinical assay kit (Testzym Heparin S) using 96-well microplates. Buffer solution (80 μL) and plasma (10 μL) was mixed with 1 U/mL antithrombin III (10 μL) at 37° C. for 5 min. After the addition of 7.1 nkat/mL FXa solution (50 μL), the reaction was started with addition of 0.75 mg/mL chromogenic substrate (100 μL). Three minutes after starting the reaction, 50% acetic acid solution (50 μL) was added and then the optical density (O.D.) at 405 nm was measured with a microplate reader (Multiskan Ascent, Dainippon pharmaceuticals Co., Japan). The anti-FXa activity (% inhibition) was calculated as follows; % inhibition=(1−O.D. of plasma sample/O.D. of normal monkey plasma)×100.

(3-2) Venous Thrombosis Model in Rats

Male Sprague-Dawley rats (7 weeks old, CLEA Japan Inc., Japan) were anaesthetized with sodium pentobarbital. Ten-millimeter length of inferior vena cava from the distal region staring the left renal vein was isolated and all side branches were ligated. A balloon catheter was introduced from the left femoral vein to inferior vena cava to injure the endothelium. Denudation of the endothelium was performed by three passes of the inflated balloon catheter (200 μL). In order to trigger the thrombus formation at the injured region, a silk thread was tied around the vena cava caudal to the left renal vein with a blunt needle (26G, Terumo), followed by the removal of the needle. Thirty minutes after the starting of partial stasis, the thrombus formed in the vena cava was removed and its wet weight was measured. And then blood samples were collected in a plastic syringe containing 3.8% sodium citrate (1:9 citrate/blood, v/v) for the measurement of prothrombin time (PT) and activated partial thromboplastin time (APTT). The test compounds were suspended in 0.5% methyl cellulose and orally administered 30 min before inducing the thrombus formation.

(3-3) Tail Transection Model in Rats

Male Sprague-Dawley rats (7 weeks old, CLEA Japan Inc., Japan) were anesthetized with sodium pentobarbital. The tail was transected at 2-3 mm proximal site from the tip. Blood was blotted every 30 sec with filter paper until either bleeding had stopped or 1800 sec had elapsed. If a bleeding does not stopped during the measurement, the BT is expressed as 1800 sec. The test compounds were suspended in 0.5% methyl cellulose and orally administered 30 min before starting the measurement of bleeding time.

(3-4) Venous Thrombosis Model in Rabbits

Male Japan White rabbits (2.3-3.0 kg, KITAYAMA LABES Ltd., Japan) were anaesthetized with ketamine and xylazine. Fifteen-millimeter length of the right jugular vein from the proximal region staring the maxillary vein was isolated and all side branches draining into the isolated jugular vein were ligated. The left femoral vein was cannulated for blood sampling. A balloon catheter (3F, Edwards Lifesciences) was introduced from the right external jugular vein to the right jugular vein to injure the endothelium. Denudation of the endothelium was performed by five passes of the inflated balloon catheter. In order to trigger the thrombus formation at the injured region, a silk thread was tied around the jugular vein at the 15 mm length from the proximal region starting the maxillary vein with a blunt needle (24G, Terumo), followed by the removal of the needle. Thirty minutes after the starting of partial stasis, the thrombus formed in the jugular vein was removed and its wet weight was measured. Before the initiation of thrombosis, the test compounds were given as a bolus (1 mL/kg) followed by a constant intravenous infusion (1 mL/kg/hr) for 1 hr. Thirty minutes after the start of administration, the thrombus formation was induced by the combination of endothelial damage and blood stagnation as described above. Blood samples were collected in a plastic syringe containing 3.8% sodium citrate (1:9 citrate/blood, v/v) before and 5, 30 and 60 min after the start of treatment for the measurement of blood coagulation parameters.

(3-5) Ex vivo Coagulation Time Measuring Method (Mouse)

(1) Intravenous Administration:

A male ICR mouse (25-35 g, CLEA Japan Inc.) was used. To a mouse anesthetized with pentobarbital (50 mg/kg, i.p.), 5 ml/kg of a drug was administered once via a tail vein. After 5 minutes from administration, 0.8 ml of blood was taken from an abdominal aorta or heart using 1/10 volume of 3.8% sodium citrate (Citral, Yamanouchi Seiyaku) and then centrifuged at 3000 rpm for 15 minutes to obtain plasma. To 50 μl of the said plasma, 100 μl of a rabbit brain-derived tissue thromboplastin solution was added, and a time required for coagulation was measured. A coagulation time was measured with an automatic coagulation time measuring apparatus (STA compact) using a PT reagent (DIAGNOSTICA ATAGO). A drug dissolved in a mixed solution of dimethylacetamide and 1/10 N hydrochloric acid was used. A mixed solution of dimethylacetamide and 1/10 N hydrochloric acid was administered to a control group in place of the drug. The activity of the drug was expressed as the ratio (%) of a coagulation time of a drug-administered group to a coagulation time of a control group.

(2) Oral Administration:

A male ICR mouse (25-35 g, Nippon Crea) was used. To a mouse which had been fasted for 12 hours or longer, 5 ml/kg of a drug was forced to be orally administered. After an hour from administration, blood was taken from an abdominal aorta under pentobarbital (50 mg/kg, i.p.) anesthesia. A drug suspended in 0.5% methylcellulose was used, and 0.5% methylcellulose in place of a drug was administered to a control group. Others were as described in (1).

(3-6) In vivo Antithrombotic Activity Measuring Method (1) Rat Arteriovenous Shunt Method:

The method was according to the method of Umetsu et al. (Thromb. Haemostas., 39, 74-73, (1978)). A male SD rat (200-350 g, Nippon Crea) was used. An extracorporeal circulation path made of a polyethylene tube provided with a silk thread was placed between the left jugular and right jugular vein of a mouse anesthetized with pentobarbital (50 mg/kg, i.p.). In order to prevent blood coagulation, the tube was previously filled with a physiological saline containing heparin (50 U/ml). Blood was circulated for 15 minutes, during which the wet weight of a thrombus attached to the silk thread was measured. A drug was administered orally or intravenously. In the case of oral administration, a drug (2 ml/kg) suspended in 0.5% methylcellulose was administered under fasting and 0.5% methylcellulose was administered to a control group instead of a drug. In the case of intravenously administration, a drug (1 ml/kg) dissolved in a physiological saline was administered via a tail vein, and a physiological saline was administered to a control group instead of a drug. The activity of the drug was calculated as the ratio (%) of a thrombus wet weight of a drug-administered group to a thrombus wet weight of a control group.

(2) Rat Abdominal Vena Cava Partial Ligation Model

A male SD rat (200-400 g, Nippon Crea) was used. After the abdominal vena cava of a mouse anesthetized with pentobarbital (50 mg/kg, i.p.) was carefully peeled, two ligatures were put round a renal vein branched part of the abdominal vena cava and a place 1 cm downstream therefrom respectively so that all branches between them were ligated. A balloon catheter (Fogarty 2F, Baxter) was inserted via the left femoral vein and the balloon was then dilated with a 200-300 ml air to damage three times between the two ligatures. The balloon catheter was taken out. The ligature put round the renal vein branched part was tied with a 26G needle and the needle was then taken out, thereby a partial ligation was made. After 30 minutes, the other ligature was tied, and a thrombus formed between the two ligatures was carefully isolated. The wet weight of the thrombus was measured using an analysis balance equipped with a windscreen (BP11OS, Satorius). A drug was administered orally or intravenously as described in (1). The activity of the drug was calculated as described in (1).

(3) Rat Deep Vein Thrombosis (DVT) Model

A male SD rat (200-350 g, Nippon Crea) was used. A polyethylene tube was inserted into the left femoral vein of a mouse anesthetized with pentobarbital (50 mg/kg, i.p.). A silk thread (length 5 cm) connected to a guide wire was inserted into the polyethylene tube and the tube was filled with a physiological saline containing heparin (50 U/ml) in order to prevent blood coagulation. After the polyethylene tube was inserted to reach the abdominal vena cava, the silk thread was allowed to be stood in the abdominal vena cava using the guide wire. After 30 minutes, heparin (200 U/kg) was intravenously administered via a tail vein. After exsanguinations by cutting of an upper arm artery, the abdominal part was opened to take out the silk thread and the wet weight of thrombus attached thereto (including weight of silk thread) was measured. A drug was administered orally or intravenously as described in (1). The wet weight of only thrombus was calculated using the equation: (wet weight of thrombus attached to silk thread)-(wet weight measured of silk thread immersed in a venous blood sample collected using heparin). The activity of the drug was calculated as described in (1).

$IC_{50}$ determined in Test Example 1 (1) is shown in Table 1. It is clear that the compound of the present invention exerts excellent FXa inhibiting effect.

TABLE 1

| Example No. | $IC_{50}$ (nM) | Example No. | $IC_{50}$ (nM) |
| --- | --- | --- | --- |
| 1 | 8.9 | 5 | 2.3 |
| 7 | 3.7 | 8 | 6.6 |
| 11 | 3.6 | 25 | 4.2 |
| 33 | 9.9 | 43 | 4.8 |

INDUSTRIAL APPLICABILITY

The compound (I) or its salt of the present invention has excellent FXa inhibiting activity and high safety as a medicament, is useful as an anticoagulant which can be orally absorbed, and is advantageously used for preventing and treating of various disorders based on thrombus and infarction.

The invention claimed is:

1. The compound 1-(1-{(2S)-3-[(6-chloronaphthalen-2-yl)sulfonyl]-2-hydroxypropanoyl}piperidin-4-yl)tetrahydropyrimidin-2(1H)-one with structural formula

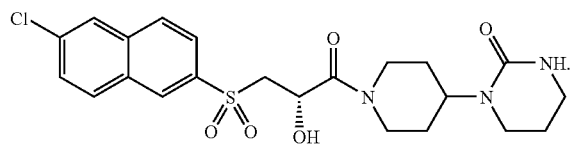

2. The compound 1-(1-{3-[(6-chloronaphthalen-2-yl)sulfonyl]-2-hydroxypropanoyl}piperidin-4-yl)tetrahydropyrimidin-2(1H)-one with structural formula

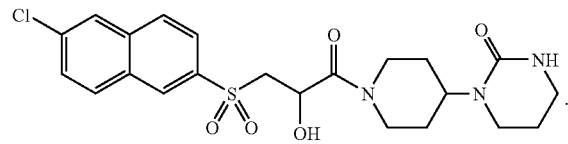

* * * * *